United States Patent
Dacey, Jr. et al.

(10) Patent No.: US 8,180,446 B2
(45) Date of Patent: May 15, 2012

(54) METHOD AND SYSTEM FOR CYCLICAL NEURAL MODULATION BASED ON ACTIVITY STATE

(75) Inventors: Ralph G. Dacey, Jr., St. Louis, MO (US); Gregory J. Della Rocca, Columbia, MO (US); Colin P. Derdeyn, St. Louis, MO (US); Joshua L. Dowling, Webster Groves, MO (US); Eleanor V. Goodall, Seattle, WA (US); Roderick A. Hyde, Redmond, WA (US); Muriel Y. Ishikawa, Livermore, CA (US); Jordin T. Kare, Seattle, WA (US); Eric C. Leuthardt, St. Louis, MO (US); Nathan P. Myhrvold, Medina, WA (US); Michael A. Smith, Phoenix, AZ (US); Lowell L. Wood, Jr., Bellevue, WA (US); Victoria Y. H. Wood, Livermore, CA (US); Gregory J. Zipfel, St. Louis, MO (US)

(73) Assignee: The Invention Science Fund I, LLC

( * ) Notice: Subject to any disclaimer, the term of this patent is extended or adjusted under 35 U.S.C. 154(b) by 1115 days.

(21) Appl. No.: 11/999,721

(22) Filed: Dec. 5, 2007

(65) Prior Publication Data
US 2009/0149895 A1 Jun. 11, 2009

(51) Int. Cl.
*A61N 1/18* (2006.01)
(52) U.S. Cl. ............................................ 607/2; 607/46
(58) Field of Classification Search .............. 607/2, 46, 607/117, 118
See application file for complete search history.

(56) References Cited

U.S. PATENT DOCUMENTS

| | | | |
|---|---|---|---|
| 3,841,306 A | 10/1974 | Hallgren | |
| 4,487,603 A | 12/1984 | Harris | |
| 4,570,640 A | 2/1986 | Barsa | |
| 4,608,985 A * | 9/1986 | Crish et al. | 607/74 |
| 4,719,919 A | 1/1988 | Marchosky et al. | |
| 4,817,628 A | 4/1989 | Zealear et al. | |
| 4,889,526 A | 12/1989 | Rauscher et al. | |
| 4,939,149 A | 7/1990 | Blumberg | |
| 5,031,618 A | 7/1991 | Mullett | |
| 5,035,891 A | 7/1991 | Runkel et al. | |
| 5,057,104 A | 10/1991 | Chess | |
| 5,061,234 A | 10/1991 | Chaney | |
| 5,092,835 A | 3/1992 | Schurig et al. | |
| 5,188,104 A | 2/1993 | Wernicke et al. | |
| 5,192,527 A | 3/1993 | Abrahmsohn | |
| 5,215,089 A | 6/1993 | Baker, Jr. | |
| 5,224,927 A | 7/1993 | Tapper | |

(Continued)

FOREIGN PATENT DOCUMENTS

WO  WO 2009/073208 A1  6/2009

(Continued)

OTHER PUBLICATIONS

U.S. Appl. No. 12/070,369, Ralph G. Dacey, Jr. et al.

(Continued)

*Primary Examiner* — Brian T Gedeon

(57) ABSTRACT

Methods and related systems for modulating neural activity by repetitively or cyclically blocking conduction in a peripheral neural structure are disclosed. Timing of delivery of blocking stimuli may be based upon overall activity level of the subject or use/activity of a portion of the body of a subject.

53 Claims, 22 Drawing Sheets

U.S. PATENT DOCUMENTS

| | | |
|---|---|---|
| 5,224,928 A | 7/1993 | Sibalis et al. |
| 5,231,988 A | 8/1993 | Wernicke et al. |
| 5,251,634 A | 10/1993 | Weinberg |
| 5,330,515 A | 7/1994 | Rutecki et al. |
| 5,335,657 A | 8/1994 | Terry, Jr. et al. |
| 5,351,394 A | 10/1994 | Weinberg |
| 5,354,320 A | 10/1994 | Schaldach et al. |
| 5,395,398 A | 3/1995 | Rogozinski |
| 5,458,625 A | 10/1995 | Kendall |
| 5,499,967 A | 3/1996 | Teillaud et al. |
| 5,527,797 A | 6/1996 | Eisenberg et al. |
| 5,531,778 A | 7/1996 | Maschino et al. |
| 5,540,730 A | 7/1996 | Terry, Jr. et al. |
| 5,558,633 A | 9/1996 | Phipps et al. |
| 5,571,150 A | 11/1996 | Wernicke et al. |
| 5,628,769 A | 5/1997 | Saringer |
| 5,683,422 A | 11/1997 | Rise |
| 5,707,400 A | 1/1998 | Terry, Jr. et al. |
| 5,755,750 A | 5/1998 | Petruska et al. |
| 5,797,898 A | 8/1998 | Santini, Jr. et al. |
| 5,814,019 A | 9/1998 | Steinbach et al. |
| 5,817,139 A | 10/1998 | Kasano |
| 5,830,207 A | 11/1998 | Leeb et al. |
| 5,830,208 A | 11/1998 | Muller |
| 5,861,022 A | 1/1999 | Hipskind |
| 5,876,422 A | 3/1999 | van Groeningen |
| 5,928,195 A | 7/1999 | Malamud et al. |
| 5,993,414 A | 11/1999 | Haller |
| 5,997,501 A | 12/1999 | Gross et al. |
| 6,012,457 A | 1/2000 | Lesh |
| 6,058,331 A | 5/2000 | King |
| 6,066,163 A | 5/2000 | John |
| 6,164,283 A | 12/2000 | Lesh |
| 6,185,455 B1 | 2/2001 | Loeb et al. |
| 6,208,894 B1 | 3/2001 | Schulman et al. |
| 6,238,421 B1 | 5/2001 | Günther et al. |
| 6,246,912 B1 | 6/2001 | Sluijter et al. |
| 6,248,126 B1 | 6/2001 | Lesser et al. |
| 6,314,325 B1 | 11/2001 | Fitz |
| 6,326,020 B1 | 12/2001 | Kohane et al. |
| 6,364,899 B1 | 4/2002 | Dobak, III |
| 6,405,732 B1 | 6/2002 | Edwards et al. |
| 6,416,495 B1 | 7/2002 | Kriesel et al. |
| 6,453,195 B1 | 9/2002 | Thompson |
| 6,454,759 B2 | 9/2002 | Krulevitch et al. |
| 6,464,687 B1 | 10/2002 | Ishikawa et al. |
| 6,527,695 B1 | 3/2003 | Davey et al. |
| 6,539,250 B1 | 3/2003 | Bettinger |
| 6,551,235 B2 | 4/2003 | Forsell |
| 6,554,822 B1 | 4/2003 | Holschneider et al. |
| 6,571,123 B2 | 5/2003 | Ives et al. |
| 6,571,125 B2 | 5/2003 | Thompson |
| 6,589,271 B1 | 7/2003 | Tzeng et al. |
| 6,600,956 B2 | 7/2003 | Maschino et al. |
| 6,622,048 B1 | 9/2003 | Mann et al. |
| 6,666,845 B2 | 12/2003 | Hooper et al. |
| 6,669,683 B2 | 12/2003 | Santini, Jr. et al. |
| 6,684,105 B2 | 1/2004 | Cohen et al. |
| 6,720,402 B2 | 4/2004 | Langer et al. |
| 6,745,078 B1 | 6/2004 | Buchner |
| 6,746,474 B2 | 6/2004 | Saadat |
| 6,755,621 B2 | 6/2004 | Lopez et al. |
| 6,761,715 B2 | 7/2004 | Carroll |
| 6,764,678 B2 | 7/2004 | Weber et al. |
| 6,770,022 B2 | 8/2004 | Mechlenburg et al. |
| 6,796,956 B2 | 9/2004 | Hartlaub et al. |
| 6,802,811 B1 | 10/2004 | Slepian |
| 6,808,522 B2 | 10/2004 | Richards et al. |
| 6,832,114 B1 | 12/2004 | Whitehurst et al. |
| 6,835,184 B1 | 12/2004 | Sage et al. |
| 6,860,852 B2 | 3/2005 | Schönenberger et al. |
| 6,871,092 B2 | 3/2005 | Piccone |
| 6,871,099 B1 | 3/2005 | Whitehurst et al. |
| 6,885,888 B2 | 4/2005 | Rezai |
| 6,921,413 B2 | 7/2005 | Mahadevan-Jansen et al. |
| 6,928,320 B2 | 8/2005 | King |
| 6,941,171 B2 | 9/2005 | Mann et al. |
| 6,976,982 B2 | 12/2005 | Santini, Jr. et al. |
| 6,978,174 B2 | 12/2005 | Gelfand et al. |
| 7,016,723 B2 | 3/2006 | Morris et al. |
| 7,031,768 B2 | 4/2006 | Anderson et al. |
| 7,033,571 B2 | 4/2006 | Gutowska et al. |
| 7,072,802 B2 | 7/2006 | Hartlaub |
| 7,076,307 B2 | 7/2006 | Boveja et al. |
| 7,108,680 B2 | 9/2006 | Rohr et al. |
| 7,113,821 B1 | 9/2006 | Sun et al. |
| 7,155,279 B2 | 12/2006 | Whitehurst et al. |
| 7,155,281 B1 | 12/2006 | Fayram |
| 7,162,303 B2 | 1/2007 | Levin et al. |
| 7,167,743 B2 | 1/2007 | Heruth et al. |
| 7,204,832 B2 | 4/2007 | Altshuler et al. |
| 7,204,833 B1 | 4/2007 | Osorio et al. |
| 7,209,787 B2 | 4/2007 | DiLorenzo |
| 7,209,788 B2 | 4/2007 | Nicolelis et al. |
| 7,226,426 B2 | 6/2007 | Thomson |
| 7,231,254 B2 | 6/2007 | DiLorenzo |
| 7,236,822 B2 | 6/2007 | Dobak, III |
| 7,242,983 B2 | 7/2007 | Frei et al. |
| 7,244,253 B2 | 7/2007 | Neev |
| 7,263,405 B2 | 8/2007 | Boveja et al. |
| 7,277,758 B2 | 10/2007 | DiLorenzo |
| 7,286,880 B2 | 10/2007 | Olson et al. |
| 7,315,761 B2 | 1/2008 | De Ridder |
| 7,319,899 B2 | 1/2008 | Keizer |
| 7,324,851 B1 | 1/2008 | DiLorenzo |
| 7,337,005 B2 * | 2/2008 | Kim et al. ........................ 607/46 |
| 7,337,006 B2 | 2/2008 | Kim et al. |
| 7,340,304 B2 | 3/2008 | MacDonald |
| 7,389,145 B2 | 6/2008 | Kilgore et al. |
| 7,613,515 B2 | 11/2009 | Knudson et al. |
| 7,620,455 B2 * | 11/2009 | Maschino ........................ 607/40 |
| 8,060,208 B2 | 11/2011 | Kilgore et al. |
| 2002/0019652 A1 | 2/2002 | Da Silva et al. |
| 2002/0058972 A1 | 5/2002 | Minogue et al. |
| 2002/0068964 A1 | 6/2002 | Dobak, III |
| 2002/0173827 A1 | 11/2002 | Jones et al. |
| 2003/0014097 A1 | 1/2003 | Putz et al. |
| 2003/0045914 A1 | 3/2003 | Cohen et al. |
| 2003/0050677 A1 | 3/2003 | Gross et al. |
| 2003/0060860 A1 | 3/2003 | Foster et al. |
| 2003/0097161 A1 | 5/2003 | Firlik et al. |
| 2003/0176901 A1 | 9/2003 | May |
| 2003/0219470 A1 | 11/2003 | Zhang et al. |
| 2004/0013716 A1 | 1/2004 | Gale et al. |
| 2004/0049134 A1 | 3/2004 | Tosaya et al. |
| 2004/0127886 A1 | 7/2004 | Daum |
| 2004/0127953 A1 | 7/2004 | Kilgore et al. |
| 2004/0172086 A1 | 9/2004 | Knudson et al. |
| 2004/0176812 A1 | 9/2004 | Knudson et al. |
| 2004/0220621 A1 | 11/2004 | Zhou et al. |
| 2005/0021103 A1 | 1/2005 | DiLorenzo |
| 2005/0021104 A1 | 1/2005 | DiLorenzo |
| 2005/0070974 A1 | 3/2005 | Knudson et al. |
| 2005/0075669 A1 | 4/2005 | King |
| 2005/0075701 A1 | 4/2005 | Shafer |
| 2005/0075702 A1 | 4/2005 | Shafer |
| 2005/0076908 A1 | 4/2005 | Lee et al. |
| 2005/0080463 A1 | 4/2005 | Stahmann et al. |
| 2005/0119713 A1 | 6/2005 | Whitehurst et al. |
| 2005/0137648 A1 | 6/2005 | Cosendai et al. |
| 2005/0138934 A1 | 6/2005 | Weigert et al. |
| 2005/0149123 A1 | 7/2005 | Lesser et al. |
| 2005/0149148 A1 | 7/2005 | King |
| 2005/0203501 A1 | 9/2005 | Aldrich et al. |
| 2005/0215947 A1 | 9/2005 | Heruth et al. |
| 2005/0216072 A1 | 9/2005 | Mahadevan-Jansen et al. |
| 2005/0234523 A1 | 10/2005 | Levin et al. |
| 2005/0277912 A1 | 12/2005 | John |
| 2005/0278001 A1 | 12/2005 | Qin et al. |
| 2005/0288730 A1 | 12/2005 | Deem et al. |
| 2006/0004417 A1 | 1/2006 | Rossing et al. |
| 2006/0036209 A1 | 2/2006 | Subramony et al. |
| 2006/0058694 A1 | 3/2006 | Clark et al. |
| 2006/0100668 A1 | 5/2006 | Ben-David et al. |
| 2006/0122454 A1 | 6/2006 | Riehl et al. |
| 2006/0122663 A1 | 6/2006 | Mandell |
| 2006/0122675 A1 | 6/2006 | Libbus et al. |

| | | |
|---|---|---|
| 2006/0155348 A1 | 7/2006 | deCharms |
| 2006/0173493 A1 | 8/2006 | Armstrong et al. |
| 2006/0190053 A1 | 8/2006 | Dobak, III |
| 2006/0247721 A1 | 11/2006 | Maschino et al. |
| 2006/0247722 A1 | 11/2006 | Maschino et al. |
| 2006/0247739 A1 | 11/2006 | Wahlstrand et al. |
| 2006/0259077 A1 | 11/2006 | Pardo et al. |
| 2006/0270944 A1 | 11/2006 | King |
| 2006/0282134 A1 | 12/2006 | Shapiro et al. |
| 2006/0293721 A1 | 12/2006 | Tarver et al. |
| 2007/0027484 A1 | 2/2007 | Guzman et al. |
| 2007/0027496 A1 | 2/2007 | Parnis et al. |
| 2007/0027497 A1 | 2/2007 | Parnis |
| 2007/0055316 A1 | 3/2007 | Godara et al. |
| 2007/0060984 A1 | 3/2007 | Webb et al. |
| 2007/0093870 A1 | 4/2007 | Maschino |
| 2007/0129760 A1 | 6/2007 | Demarais et al. |
| 2007/0129774 A1 | 6/2007 | Bourget et al. |
| 2007/0135875 A1 | 6/2007 | Demarais et al. |
| 2007/0142875 A1 | 6/2007 | Shalev et al. |
| 2007/0150025 A1 | 6/2007 | Dilorenzo et al. |
| 2007/0150029 A1 | 6/2007 | Bourget et al. |
| 2007/0156032 A1 | 7/2007 | Gordon et al. |
| 2007/0156206 A1 | 7/2007 | Wahlstrand et al. |
| 2007/0167984 A1 | 7/2007 | Kieval et al. |
| 2007/0173899 A1 | 7/2007 | Levin et al. |
| 2007/0179557 A1 | 8/2007 | Maschino et al. |
| 2007/0191906 A1 | 8/2007 | Iyer et al. |
| 2007/0225781 A1 | 9/2007 | Saadat et al. |
| 2007/0255374 A1 | 11/2007 | Kolafa et al. |
| 2008/0045879 A1 | 2/2008 | Prausnitz et al. |
| 2008/0077198 A1 | 3/2008 | Webb et al. |
| 2008/0300657 A1* | 12/2008 | Stultz .............................. 607/60 |

FOREIGN PATENT DOCUMENTS

| | | |
|---|---|---|
| WO | WO 2009/073223 A1 | 6/2009 |
| WO | WO 2009/075783 A1 | 6/2009 |

OTHER PUBLICATIONS

U.S. Appl. No. 12/070,361, Ralph G. Dacey, Jr. et al.
U.S. Appl. No. 12/070,332, Ralph G. Dacey, Jr. et al.
U.S. Appl. No. 12/070,331, Ralph G. Dacey, Jr. et al.
Binshtok, Alexander M.; Bean, Bruce P.; Woolf, Clifford J.; "Inhibition of Nociceptors by TRPV1-Mediated Entry of Impermeant Sodium Channel Blockers"; Nature, Letters; bearing a date of Oct. 4, 2007; pp. 607-611; vol. 449; Nature Publishing Group.
Fang, Zi-Ping; Mortimer, J. Thomas; "Selective Activation of Small Motor Axons by Quasitrapezoidal Current Pulses"; IEEE Transactions on Biomedical Engineering; bearing a date of Feb. 1991; pp. 168-174; vol. 38, No. 2; IEEE.
Harland, C.J.; Clark, T.D.; Prance, R.J.; "Remote Detection of Human Electroencephalograms Using Ultrahigh Input Impedance Electric Potential Sensors"; Applied Physics Letters; bearing a date of Oct. 21, 2002; pp. 3284-3286; vol. 81, No. 17; American Institute of Physics.
Hodgkin, A.L.; Huxley, A.F.; "A Quantitative Description of Membrane Current and its Application to Conduction and Excitation in Nerve"; Journal of Physiology; bearing a date of 1952; pp. 500-544; vol. 117.
Howarth, Peter H.; Persson, Carl G.A.; Meltzer, Eli O.; Jacobson, Mikila R.; Durham, Stephen R.; Silkoff, Philip E.; "Objective Monitoring of Nasal Airway Inflammation in Rhinitis"; Journal of Allergy Clin Immunol; Mar. 2005; pp. S414-S441; American Academy of Allergy, Asthma and Immunology.
Hsu, Kai-Hsiung; Durand, Dominique M.; "A 3-D Differential Coil Design for Localized Magnetic Stimulation"; IEEE Transactions on Biomedical Engineering; Oct. 2001; pp. 1162-1168; vol. 48, No. 10; IEEE.
Hsu, Kai-Hsiung; Durand, Dominique M.; "Prediction of Neural Excitation During Magnetic Stimulation Using Passive Cable Models"; IEEE Transactions on Biomedical Engineering; Apr. 2000; pp. 463-471; vol. 47, No. 4; IEEE.
Hsu, Kai-Hsiung; Nagarajan, Srikantan S.; Durand, Dominique M.; "Analysis of Efficiency of Magnetic Stimulation"; IEEE Transactions on Biomedical Engineering; Nov. 2003; pp. 1276-1285; vol. 50, No. 11; IEEE.
Kilani, Ruhangiz T.; Maksymowych, Walter P.; Aitken, Alastair; Boire, Gilles; St. Pierre, Yves; Li, Yunyuan; Ghahary, Aziz; "Detection of High Levels of 2 Specific Isoforms of 14-3-3 Proteins in Synovial Fluid from Patients with Joint Inflammation"; The Journal of Rheumatology; 2007; pp. 1650-1657; vol. 34, No. 8.
Ma, Qing-Ping; "Vanilloid Receptor Homologue, VRLI, is Expressed by Both A- and C- Fiber Sensory Neurons" NeuroReport, Somatosensory Systems, Pain; bearing a date of Dec. 4, 2001; pp. 3693-3695; vol. 12, No. 17; Lippincott Williams & Wilkins.
"Makers of ActiPatch™ a Drug-Free, Anti-Inflammatory Patch that Resolves Swellin"; BioElectronics; 2004; pp. 1-4; BioElectronics Corp.
Marks, William B.; Loeb, Gerald E.; "Action Currents, Internodal Potentials, and Extracellular Records of Myelinated Mammalian Nerve Fibers Derived from Node Potentials"; Biophysical Journal; 1976; pp. 655-668; vol. 16.
McCleskey, Edwin W.; "Neuroscience: A Local Route to Pain Relief"; Nature—News & Views; bearing a date of Oct. 4, 2007; pp. 545-546; vol. 449; Nature Publishing Group.
McNeal, Donald R.; "Analysis of a Model for Excitation of Myelinated Nerve"; IEEE Transactions on Biomedical Engineering; bearing a date of Jul. 1976; pp. 329-337; vol. BME-23, No. 4.
Pareek, Tej K.; Keller, Jason; Kesavapany, Sashi; Pant, Harish C.; Ladarola, Michael J.; Brady, Roscoe O.; Kulkarni, Ashok B.; "Cyclin-Dependent Kinase 5 Activity Regulates Pain Signaling"; PNAS; bearing a date of Jan. 17, 2006; pp. 791-796; vol. 103, No. 3.
Poole, A R; "Immunochemical Markers of Joint Inflammation, Skeletal Damage and Repair: Where are we now?"; Annals of the Rheumatic Diseases; 1994; pp. 3-5; vol. 53.
"Product Information: Actipatch"; BioElectronics, Medical Professionals Info Center; 2004; pp. 1-3; BioElectronics Corp.
Rattay, Frank; "Analysis of Models for Extracellular Fiber Stimulation"; IEEE Transactions on Biomedical Engineering; bearing a date of Jul. 1989; pp. 676-682; vol. 36, No. 7; IEEE.
Rattay, Frank; "Modeling the Excitation of Fibers Under Surface Electrodes"; IEEE Transactions on Biomedical Engineering; Mar. 1988; pp. 199-202; vol. 35, No. 3; IEEE.
Rattay, Frank, Aberham, Matthias; "Modeling Axon Membranes from Functional Electrical Stimulation"; IEEE Transactions on Biomedical Engineering; bearing a date of Dec. 1993; pp. 1201-1209; vol. 40, No. 12; IEEE.
Rooney, Terence; Bresnihan, Barry; Andersson, Ulf; Gogarty, Martina; Kraan, Maarten; Schumacher, H. Ralph; Ulfgren, Ann-Kristin; Veale, Douglas J.; Youssef, Peter P.; Tak, Paul P.; "Microscopic Measurement of Inflammation in Synovial Tissue: Inter-Observer Agreement for Manual Quantitative, Semiquantitative and Computerised Digital Image Analysis"; Ann Rheum Dis; 2007; pp. 1656-1660; vol. 66.
Struijk, Johannes Jan; "The Extracellular Potential of a Myelinated Nerve Fiber in an Unbounded Medium and in Nerve Cuff Models"; Biophysical Journal; bearing a date of Jun. 1997; pp. 2457-2469; vol. 72; Biophysical Society.
Tokushige, Natsuko; Markham, Robert; Russell, Peter; Fraser, Ian S.; "Nerve Fibers in Peritoneal Endometriosis"; Human Reproduction; 2006; pp. 3001-3007; vol. 21, No. 11.
"Treatment Blocks Pain Without Disrupting Other Functions"; published: Oct. 3, 2007; 3 pages; located at: http://www.physorg.com/news110637008.html.
Voloshin, Ilya; Gelinas, Jill; Maloney, Michael D.; O'Keefe, Regis J.; Bigliani, Louis U.; Blaine, Theodore A.; "Proinflammatory Cytokines and Metalloproteases are Expressed in the Subacromial Bursa in Patients with Rotator Cuff Disease"; The Journal of Arthroscopic and Related Surgery; 2005; pp. 1076e1-1076e9; vol. 21, No. 9.
PCT International Search Report; International App. No. PCT/US 08/13443; Feb. 20, 2009; pp. 1-2.
PCT International Search Report; International App. No. PCT/US 08/13442; Feb. 20, 2009; pp. 1-3.
PCT International Search Report; International App. No. PCT/US 08/13407; Feb. 20, 2009; pp. 1-2.
PCT International Search Report; International App. No. PCT/US2008/013406; Feb. 9, 2009; pp. 1-2.

Douglas, W.W.; Malcom, J.L.; "The Effect of Localized Cooling on Conduction in Cat Nerves"; Journal of Physiology; 1955; pp. 53-71; vol. 130; located at: jp.physoc.org.

Franz, D.N.; Iggo, A.; "Conduction Failure in Myelinated and Non-Myelinated Axons at Low Temperatures"; Journal of Physiology; 1968; pp. 319-345; vol. 199.

Belverud, Shawn; Mogilner, Alon; Schulder, Michael; "Intrathecal Pumps"; Neurotherapeutics: The Journal of the American Society for Experimental NeuroTherapeutics; Jan. 2008; pp. 114-122; vol. 5, No. 1.

Burdakov, Denis; Gerasimenko, Oleg; Verkhratsky, Alexei; "Brief Communication: Physiological Changes in Glucose Differentially Modulate the Excitability of Hypothalamic Melanin-Concentrating Hormone and Orexin Neurons In Situ"; The Journal of Neuroscience; bearing a date of Mar. 2, 2005; pp. 2429-2433; vol. 25, No. 9.

U.S. Appl. No. 12/214,758, filed Jun. 18, 2008, Dacey, Jr. et al.
U.S. Appl. No. 12/214,559, filed Jun. 18, 2008, Dacey, Jr. et al.
U.S. Appl. No. 12/214,558, filed Jun. 18, 2008, Dacey, Jr. et al.
U.S. Appl. No. 12/214,557, filed Jun. 18, 2008, Dacey, Jr. et al.
U.S. Appl. No. 12/214,545, filed Jun. 18, 2008, Dacey, Jr. et al.
U.S. Appl. No. 12/214,533, filed Jun. 18, 2008, Dacey, Jr. et al.

"Device blocking stomach nerve signals shows promise in obesity", PHYSORG.COM, Mayo Clinic, bearing a date of Jun. 26, 2008, pp. 1-2, located at http://www.physorg.com/news133701913.html.

Gordon, Ryan D.; Peterson, Tim A.; "4 Myths About Transdermal Drug Delivery"; Drug Delivery Technology; bearing a date of Jun. 4, 2003 and posted on Mar. 28, 2008; pp. 1-9; vol. 3, No. 4.

Grayson, Amy C. Richards; Shawgo, Rebecca S.; Johnson, Audrey M.; Flynn, Nolan T.; Li, Yawen; Cima, Michael J.; Langer, Robert; "A BioMEMS Review: MEMS Technology for Physiologically Integrated Devices"; Proceedings of the IEEE; bearing a date of Jan. 2004; pp. 6-21; vol. 92, No. 1.

Hsieh, Dean S. T.; Langer Robert; Folkman, Judah; "Magnetic Modulation of Release of Macromolecules from Polymers"; Proc. Natl. Acad. Sci. USA; bearing a date of Mar. 1981; pp. 1863-1867; vol. 78. No. 3.

Power, I.; "Review Article: Fentanyl HCI Iontophoretic Transdermal System (ITS): Clinical Application of Iontophoretic Technology in the Management of Acute Postoperative Pain"; British Journal of Anaesthesia; bearing a date of 2007; pp. 4-11; vol. 98, No. 1.

Prescott, James H.; Lipka, Sara; Baldwin, Samuel; Sheppard, Jr., Norman F.; Maloney, John M.; Coppeta, Jonathan; Yomtov, Barry; Staples, Mark A.; Santini, Jr., John T.; "Brief Communications: Chronic, Programmed Polypeptide Delivery from an Implanted, Multireservoir Microchip Device"; Nature Biotechnology; bearing a date of Apr. 2006; pp. 437-438; vol. 24, No. 4; located at: www.nature.com/naturebiotechnology.

"Robot Anaesthetist Developed in France: Doctor"; Yahoo!; Agence France Press; bearing a date of Apr. 12, 2008; pp. 1-2.

Roxhed, Niclas; Samel, Bjorn; Nordquist, Lina; Griss, Patrick; Stemme, Goran; "Painless Drug Delivery Through Microneedle-Based Transdermal Patches Featuring Active Infusion"; IEEE Transactions on Biomedical Engineering; bearing a date of Mar. 2008; pp. 1063-1071; vol. 55, No. 3.

Saliba, Susan; Mistry, Dilaawar J.; Perrin, David H.; Gieck, Joe; Weltman, Arthur; "Original Research: Phonophoresis and the Absorption of Dexamethasone in the Presence of an Occlusive Dressing"; Journal of Athletic Training; 2007; pp. 349-354; National Athletic Trainers' Association, Inc; located at: www.journalofathletictraining.org.

Singer, Emily; "A New Way to Treat Obesity"; Technology Review; bearing a date of May 15, 2008; pp. 1-3; MIT.

Stubbe, Barbara G.; De Smedt, Stefaan C.; Demeester, Joseph; "Review "Programmed Polymeric Devices" for Pulsed Drug Delivery"; Pharmaceutical Research; bearing a date of Oct. 2004; pp. 1732-1740; vol. 21, No. 10.

Singer, Emily; "Neural Stimulation for Autoimmune Diseases"; Technology Review; bearing a date of Jun. 1, 2010; pp. 1-2; MIT.

"Application Note—Rat Sciatic Nerve"; Aculight Corporation; bearing a date of Dec. 6, 2006; pp. 1-2 (front and back).

Bjordal, Jan M.; Johnson, Mark I.; Lopes-Martins, Rodrigo AB; Bogen, Bard; Chow, Roberta; Ljunggren, Anne E.; "Short-Term Efficacy of Physical Interventions in Osteoarthritic Knee Pain. A Systematic Review and Meta-Analysis of Randomised Placebo-Controlled Trials."; BMC Musculoskeletal Disorders, BioMed Central; 2007; pp. 1-34, plus cover page and Figs.1-8; vol. 8, No. 51; BioMed Central Ltd.; located at: http://www.biomedcentral.com/1471-2474/8/51.

Boggs, Will; "Physical Interventions can be Effective for Osteoarthritic Knee Pain"; WebMD; 1994-2007; pp. 1-2; Medscape; located at: http://www.medscape.com/viewarticle/559501; printed on Jul. 12, 2007.

Bostock, Hugh; Cikurel, Katia; Burke, David; "Invited Review: Threshold Tracking Techniques in the Study of Human Peripheral Nerve"; Muscle & Nerve; Feb. 1998; pp. 137-158; John Wiley & Sons, Inc.

Brooks, Jonathan; Tracey, Irene; "Review: From Nociception to Pain Perception: Imaging the Spinal and Supraspinal Pathways"; Journal of Anatomy; 2005; pp. 19-33; vol. 207; Anatomical Society of Great Britain and Ireland.

"Could Nerve-Snip Spur Weight Loss?"; CNN.com; 2007; pp. 1-2; Cable News Network; located at: http://www.cnn.com/2007/HEALTH/conditions/07/09/obesity.nerve.ap/index.html; printed on Jul. 12, 2007.

Han, Xue; Boyden, Edward S.; "Multiple-Color Optical Activation, Silencing, and Desynchronization of Neural Activity, with Single-Spike Temporal Resolution"; PLoS ONE; Mar. 2007; pp. 1-12; Issue 3, No. e299; located at: www.plosone.org.

Hinrikus, H.; Lass, J.; Tuulik, V.; "Low-Level Microwave Effect on Nerve Pulse Propagation Velocity"; Proceedings of the $25^{th}$ Annual International Conference of the IEEE EMBS; bearing dates of Sep. 17-21, 2003; pp. 3253-3256; IEEE.

Hong, CZ; "Reversible Nerve Conduction Block in Patients with Polyneuropathy After Ultrasound Thermotherapy at Therapeutic Dosage."; Archives of Physical Medicine and Rehabilitation; Feb. 1991; pp. 132-137, only the abstract is being provided; vol. 72, No. 2; located at: http://www.ncbi.nlm.nih.gov/sites/entrez?cmd=Retrieve&db=PubMed&list_uids=1846738&dopt=AbstractPlus; printed on May 9, 2007.

Kane, D.; Lockhart, JC; Balint, PV; Mann, C.; Ferrell, WR; McInnes, IB; "Protective Effect of Sensory Denervation in Inflammatory Arthritis (evidence of regulatory neuroimmune pathways in the arthritic joint)"; ARD Online, Ann. Rheum. Dis.; 2005; pp. 325-327 plus cover page; vol. 64; located at: www.annrheumdis.com.

Kilgore, K.L.; Bhadra, N.; "Nerve Conduction Block Utilising High-Frequency Alternating Current"; Medical & Biological Engineering & Computing; 2004; pp. 394-406; vol. 42; IFMBE.

Krasteva, Vessela TZ; Papazov, Sava P.; Daskalov, Ivan K.; "Peripheral Nerve Magnetic Stimulation: Influence of Tissue Non-Homogeneity"; BioMedical Engineering online; 2003; pp. 1-14; located at: http://www.biomedical-engineering-online.com/content/2/1/19.

Krauthamer, V.; Crosheck, T.; "Effects of High-Rate Electrical Stimulation Upon Firing in Modelled and Real Neurons"; Medical & Biological Engineering & Computing; 2002; pp. 360-366; vol. 40; IFMBE.

Kuwabara, Satoshi; Cappelen-Smith, Cecilia; Lin, Cindy S.-Y.; Mogyoros, Ilona; Bostock, Hugh; Burke, David; "Excitability Properties of Median and Perneal Motor Axons"; Muscle and Nerve; Sep., 2000; pp. 1365-1373; vol. 23.

Lam, FY; Ferrell, WR; "Neurogenic Component of Different Models of Acute Inflammation in the Rat Knee Joint."; PubMed, NCBI, Ann. Rheum. Dis.; Nov. 1991; pp. 747-751, only the abstract is enclosed; vol. 50, No. 11; printed on May 17, 2007.

Lele, P.P.; "Effects of Focused Ultrasonic Radiation on Peripheral Nerve, with Observations on Local Heating"; Experimental Neurology; 1963; pp. 47-83; vol. 8.

Lin, Cindy S.-Y.; Mogyoros, Ilona; Kuwabara, Satoshi; Cappelen-Smith, Cecilia; Burke, David; "Accommodation to Depolarizing and Hyperpolarizing Currents in Cutaneous Afferents of the Human Median and Sural Nerves"; The Journal of Physiology Online; J. Physiol. 2000; pp. 483-492; vol. 529; located at: http://www.jp.physoc.org/cgi/content/full/529/2/483 ; printed on Oct. 5, 2007.

"Local Anaesthetics and Nerve Conduction"; The Virtual Anaesthesia Textbook; pp. 1-2; located at: http://www.virtual-anaesthesia-textbook.com.

Norton, Stephen J.; "Research: Can Ultrasound be Used to Stimulate Nerve Tissue?"; BioMedical Engineering OnLine; 2003; pp. 1-9; vol. 2, No. 6; BioMed Central Ltd.; located at: http://www.biomedical-engineering-online.com/content/2/1/6.

Orlee, Kenneth S., Horch, Kenneth W.; "Differential Activiation and Block of Peripheral Nerve Fibers by Magnetic Fields"; Muscle and Nerve; 2006; pp. 189-196; vol. 34; located at: www.interscience.wiley.com.

Pavlov, V.A.; Tracey, K.J.; "Review: Neural Regulators of Innate Immune Responses and Inflammation"; CMLS—Cellular and Molecular Life Sciences; 2004; pp. 2322-2331; vol. 61; Birkhäuser Verlag, Basel.

Peckham, P. Hunter; Knutson, Jayme S.; "Functional Electrical Stimulation for Neuromuscular Applications"; Annual Reviews; 2005; pp. 327-360; located at: http://www.arjournals.annualreviews.org ; printed on Feb. 13, 2007.

Pham-Marcou, T.A.; Gentili, M.; Asehnoune, K.; Fletcher, D.; Mazoit, J.-X.; "Pain: Effect of Neurolytic Nerve Block on Systemic Carrageenan-Induced Inflammatory Response in Mice"; British Journal of Anaesthesia; 2005; pp. 243-246; vol. 95, No. 2; The Board of Management and Trustees of the British Journal of Anaesthesia.

Razavi, Rozita; Chan, Yin; Afifiyan, F. Nikoo; Liu, Xue Jun; Wan, Xiang; Yantha, Jason; Tsui, Hubert; Tang, Lan; Tsai, Sue; Santamaria, Pere; Driver, John P.; Serreze, David; Salter, Michael W.; Dosch, H.-Michael; "TRPV1+ Sensory Neurons Control β Cell Stress and Islet Inflammation in Autoimmune Diabetes"; Cell; bearing a date of Dec. 15, 2006; pp. 1123-1135; vol. 127; Elsevier Inc.

Sternberg, Esther M.; "Neural Regulation of Innate Immunity: A Coordinated Nonspecific Host Response to Pathogens"; NIH Public Access, Author Manuscript—Nat. Rev. Immunol.; Apr. 2006; pp. 318-328 (pp. 1-26); vol. 6, No. 4.

"Study Finds Nerve Damage in Previously Mysterious Chronic Pain Syndrome"; Doctor's Guide, Personal Edition; 2007; pp. 1-2 (front and back); located at: http://www.docguide.com/news/content.nsf/NewsPrint/852571020057CCF685257107005273F6; printed on May 9, 2007.

Tai, Changfeng; De Groat, William C.; Roppolo, James R.; "Simulation Analysis of Conduction Block in Unmyelinated Axons Induced by High-Frequency Biphasic Electrical Currents"; IEEE Transactions on Biomedical Engineering; Jul. 2005; pp. 1323-1332; vol. 52, No. 7.

Tracey, Kevin J.; "Review: Physiology and Immunology of the Cholinergic Antiinflammatory Pathway"; The Journal of Clinical Investigation; Feb. 2007; pp. 289-296; vol. 117, No. 2; located at: http://www.jci.org.

Tsui, Po-Hsiang; Wang, Shyh-Hau; Huang, Chih-Chung; "In Vitro Effects of Ultrasound with Different Energies on the Conduction Properties of Neural Tissue"; ScienceDirect—Ultrasonics; 2005; pp. 560-565; vol. 43; Elsevier B.V.; located at: www.elsevier.com/locate/ultras.

Van Den Honert, Christopher; Mortimer, J. Thomas; "A Technique for Collision Block of Peripheral Nerve: Single Stimulus Analysis"; IEEE Transactions on Biomedical Engineering; May 1981; pp. 373-378; vol. BME-28, No. 5.

Walsh, Raymond R.; Deal, Stanley E.; "Reversible Conduction Block Produced by Lipid-Insoluble Quarternary Ammonium Ions in Cetyltrimethylammonium Bromide-Treated Nerves"; Am J Physiol; 1959; pp. 547-550; Only the abstract is being provided; vol. 197; located at: http://ajplegacy.physiology.org.

Wells, Jonathan; Kao, Chris; Konrad, Peter; Milner, Tom; Kim, Jihoon; Mahadevan-Jansen, Anita; Jansen, E. Duco; "Application of Infared Light for In Vivo Neural Stimulation"; The Journal of Biomedical Optics; Nov./Dec. 2005; pp. 064003-1-064003-12; vol. 10(6).

Wells, Jonathan; Kao, Chris; Konrad, Peter; Milner, Tom; Kim, Jihoon; Mahadevan-Jansen, Anita; Jansen, E. Duco; "Biophysical Mechanisms of Transient Optical Stimulation of Peripheral Nerve"; Biophysical Journal; Oct. 2007; pp. 2567-2580; vol. 93.

Wells, Jonathan; Konrad, Peter; Kao, Chris; Jansen, E. Duco; Mahadevan-Jansen, Anita; "Pulsed Laser Versus Electrical Energy for Peripheral Nerve Stimulation"; Journal of Neuroscience Methods; 2007; pp. 326-337; located at: www.elsevier.com/locate/jneumeth.

Windle, Mary L.; "Anesthesia, Topical"; E-Medicine from WebMD; Mar. 14, 2007; pp. 1-4; located at: www.webmd.com.

Zhang, Xu; Roppolo, James R.; De Groat, William C.; Tai, Changfeng; "Mechanism of Nerve Conduction Block Induced by High-Frequency Biphasic Electrical Currents"; IEEE Transactions on Biomedical Engineering; Dec. 2006; pp. 2445-2454; vol. 53, No. 12.

Zhang, Xu; Roppolo, James R.; De Groat, William C.; Tai, Changfeng; "Simulation Analysis of Conduction Block in Myelinated Axons Induced by High-Frequency Biphasic Rectangular Pulses"; IEEE Transactions on Biomedical Engineering; Jul. 2006; pp. 1433-1436; ; vol. 53, No. 7.

UK Intellectual Property Office Examination Report under Section 18(3); Application No. GB1010163.2; Jan. 26, 2012; pp. 1-2.

* cited by examiner

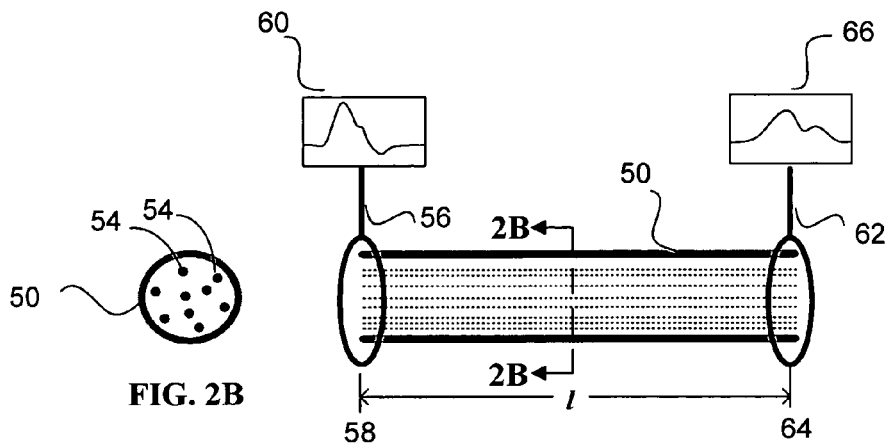
FIG. 2A
FIG. 2B
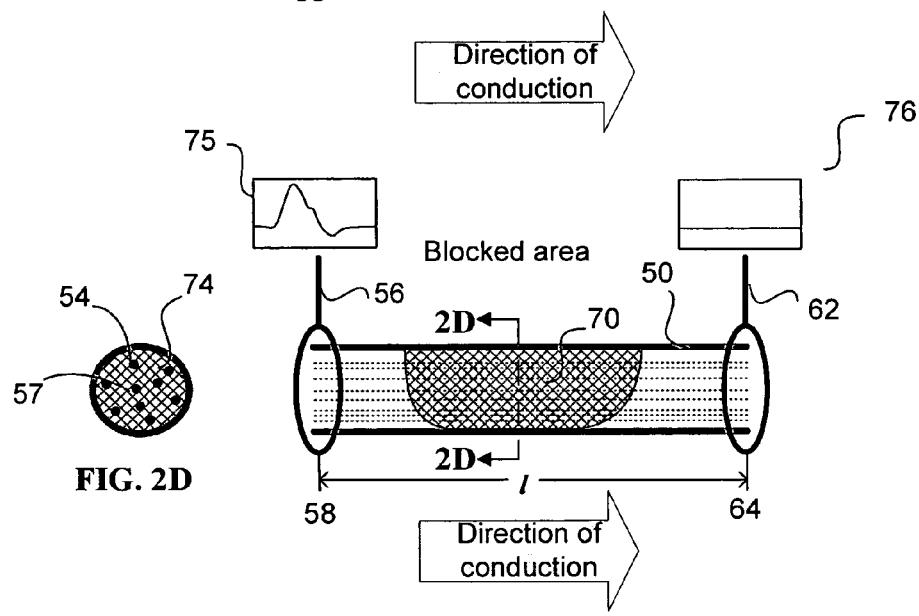
FIG. 2C
FIG. 2D
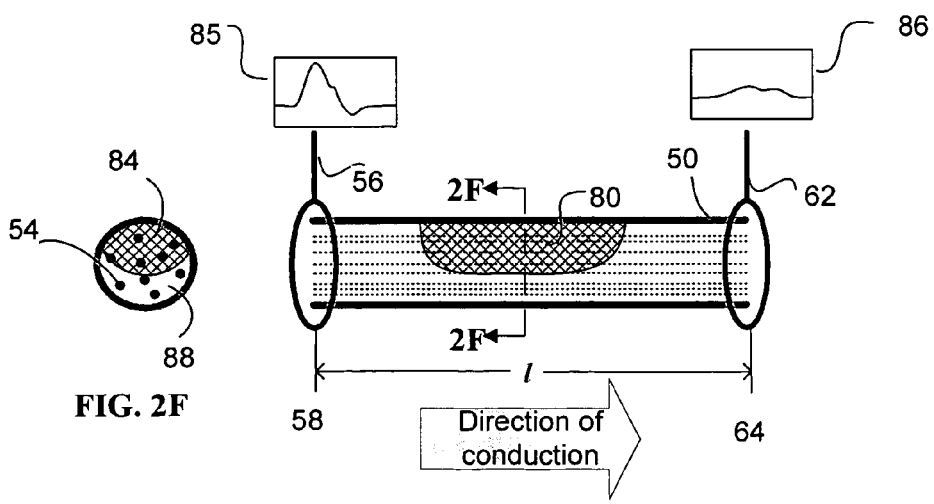
FIG. 2E
FIG. 2F

applying a blocking stimulus sufficient to produce a reversible
   conduction block of at least a portion of a peripheral neural
   structure of a subject with a cyclical application pattern, the
   cyclical application pattern including:
   a blocking period during which the blocking stimulus sufficient
       to produce a reversible conduction block of at least a
       portion of the peripheral neural structure of the subject is
       applied at least intermittently, the blocking period
       coinciding at least in part with a first activity state in the
       subject; and
   a release period during which no blocking stimulus is applied, the
       release period coinciding at least in part with a second
       activity state in the subject.

200

---
Signal bearing medium
1252

---
one or more instructions related to applying a blocking stimulus sufficient to produce a reversible conduction block of at least a portion of a peripheral neural structure of a subject with a cyclical application pattern, the application pattern including:

a blocking period during which the blocking stimulus sufficient produce a reversible conduction block of at least a portion of the peripheral neural structure of the subject is applied at least intermittently, the blocking period coinciding at least in part with a first activity state in the subject; and a release period during which no blocking stimulus is applied, the release period coinciding at least in part with a second activity state in the subject

1254

---
one or more instructions related to detecting the onset of the first activity state in the subject 1256

---
one or more instructions related to initiating a blocking period during which a blocking stimulus sufficient produce to reversible conduction block of at least a portion of the peripheral neural structure of the subject is applied at least intermittently responsive to detecting the onset of the first activity state in the subject 1258

FIG. 21

METHOD AND SYSTEM FOR CYCLICAL NEURAL MODULATION BASED ON ACTIVITY STATE

SUMMARY

In one aspect, a method of modulating neural activity includes but is not limited to applying a blocking stimulus sufficient to produce a reversible conduction block of at least a portion of a peripheral neural structure of a subject with a cyclical application pattern, a cycle of the cyclical application pattern including a blocking period during which the blocking stimulus sufficient to produce a reversible conduction block of at least a portion of the peripheral neural structure of the subject is applied at least intermittently, the blocking period coinciding at least in part with a first activity state in the subject; and a release period during which no blocking stimulus is applied, the release period coinciding at least in part with a second activity state in the subject.

In another aspect, a method of modulating neural activity includes but is not limited to detecting the onset of a first activity state in the subject; initiating a blocking period during which a blocking stimulus sufficient to produce a reversible conduction block of at least a portion of the peripheral neural structure of the subject is applied at least intermittently responsive to detecting the onset of a first activity state in the subject; and applying the blocking stimulus sufficient to produce a reversible conduction block of at least a portion of a peripheral neural structure of a subject with a cyclical application pattern, a cycle of the cyclical application pattern including a blocking period during which the blocking stimulus sufficient to produce a reversible conduction block of at least a portion of the peripheral neural structure of the subject is applied at least intermittently, the blocking period coinciding at least in part with a first activity state in the subject; and a release period during which no blocking stimulus is applied, the release period coinciding at least in part with a second activity state in the subject.

In yet another aspect, a method of modulating neural activity may include applying a blocking stimulus sufficient to produce a reversible conduction block of at least a portion of a peripheral neural structure of a subject with a cyclical application pattern, a cycle of the cyclical application pattern including a blocking period during which the blocking stimulus sufficient to produce a reversible conduction block of at least a portion of the peripheral neural structure of the subject is applied at least intermittently, the blocking period coinciding at least in part with a first activity state in the subject; a release period during which no blocking stimulus is applied, the release period coinciding at least in part with a second activity state in the subject; detecting the onset of a second activity state in the subject; and initiating a release period during which no blocking stimulus is applied responsive to detecting second activity state in the subject.

In addition to the foregoing, other method aspects are described in the claims, drawings, and text forming a part of the present disclosure.

In one aspect, a neural modulation system includes but is not limited to a signal input structure configured to receive a signal indicative of an activity state of at least a portion of a body of a subject innervated by a peripheral neural structure; a sensor operatively connected to the signal input structure and configured to generate the signal indicative of an activity state of the at least a portion of the body of the subject innervated by the peripheral neural structure responsive to an activity of the at least a portion of the body of the subject; and a signal processing portion configured to distinguish a first activity state of the at least a portion of the body of the subject innervated by the peripheral neural structure from a second activity state of the at least a portion of the body of the subject innervated by the peripheral neural structure from the signal received at the signal input structure and generate a blocking stimulus control signal for driving production of a blocking stimulus configured to reversibly block conduction in the peripheral neural structure of the subject during at least a portion of the first activity state. The sensor may be a physiological sensor or a physical activity sensor, for example.

In another aspect, a neural modulation system may include a signal input structure configured to receive a signal indicative of an activity state of at least a portion of a body of a subject innervated by a peripheral neural structure; a user input device operatively connected to the signal input structure and configured to generate a signal responsive to a user input indicative of an activity state of at least a portion of a body portion innervated by the peripheral neural structure; and a signal processing portion configured to distinguish a first activity state of the at least a portion of the body of the subject innervated by the peripheral neural structure from a second activity state of the at least a portion of the body of the subject innervated by the peripheral neural structure from the signal received at the signal input structure; and generate a blocking stimulus control signal for driving production of a blocking stimulus configured to reversibly block conduction in the peripheral neural structure of the subject during at least a portion of the first activity state.

In addition to the foregoing, other system aspects are described in the claims, drawings, and text forming a part of the present disclosure.

In one or more various aspects, related systems include but are not limited to circuitry and/or programming, including instructions carried on signal bearing media, for effecting the herein-referenced method aspects.

In one aspect, a system may include a signal-bearing medium bearing one or more instructions related to producing a reversible conduction block in a peripheral neural structure of a subject while the subject is in a first activity state, one or more instructions related to reversing the reversible conduction block in the peripheral neural structure of the subject to permit conduction in the peripheral neural structure when the subject is in a second activity state, and one or more instructions related to repeating the steps of producing a reversible conduction block in a peripheral neural structure of a subject while the subject is in a first activity state and reversing the reversible conduction block in the peripheral neural structure of the subject to permit conduction in the peripheral neural structure when the subject is in a second activity state.

In another aspect, a system may include a signal-bearing medium bearing one or more instructions related to receiving an input indicative of an activity state of the subject, one or more instructions related to producing a reversible conduction block in a peripheral neural structure of a subject while the subject is in a first activity state; one or more instructions related to reversing the reversible conduction block in the peripheral neural structure of the subject to permit conduction in the peripheral neural structure when the subject is in a second activity state, and one or more instructions related to repeating the steps of producing a reversible conduction block in a peripheral neural structure of a subject while the subject is in a first activity state and reversing the reversible conduction block in the peripheral neural structure of the subject to permit conduction in the peripheral neural structure when the subject is in a second activity state.

In yet another aspect, a system may include a signal-bearing medium bearing one or more instructions related to producing a reversible conduction block in a peripheral neural structure of a subject while the subject is in a first activity state; one or more instructions related to receiving an input indicative of a user instruction; one or more instructions related to reversing the reversible conduction block in the peripheral neural structure of the subject to permit conduction in the peripheral neural structure when the subject is in a second activity state; and one or more instructions related to repeating the steps of producing a reversible conduction block in a peripheral neural structure of a subject while the subject is in a first activity state and reversing the reversible conduction block in the peripheral neural structure of the subject to permit conduction in the peripheral neural structure when the subject is in a second activity state.

In still another aspect, a system may include a signal bearing medium bearing: one or more instructions related to applying a blocking stimulus sufficient to produce a reversible conduction block of at least a portion of a peripheral neural structure of a subject with a cyclical application pattern, a cycle of the cyclical application pattern including a blocking period during which the blocking stimulus sufficient produce a reversible conduction block of at least a portion of the peripheral neural structure of the subject is applied at least intermittently, the blocking period coinciding at least in part with a first activity state in the subject; and a release period during which no blocking stimulus is applied, the release period coinciding at least in part with a second activity state in the subject.

In still another aspect, a system may include a signal bearing medium bearing one or more instructions related to applying a blocking stimulus sufficient to produce a reversible conduction block of at least a portion of a peripheral neural structure of a subject with a cyclical application pattern, a cycle of the cyclical application pattern including a blocking period during which the blocking stimulus sufficient produce a reversible conduction block of at least a portion of the peripheral neural structure of the subject is applied at least intermittently, the blocking period coinciding at least in part with a first activity state in the subject; and a release period during which no blocking stimulus is applied, the release period coinciding at least in part with a second activity state in the subject; one or more instructions related to detecting the onset of the first activity state in the subject; and one or more instructions related to initiating a blocking period during which a blocking stimulus sufficient produce to reversible conduction block of at least a portion of the peripheral neural structure of the subject is applied at least intermittently responsive to detecting the onset of the first activity state in the subject.

In another aspect, a system may include a signal bearing medium bearing one or more instructions related to applying a blocking stimulus sufficient to produce a reversible conduction block of at least a portion of a peripheral neural structure of a subject with a cyclical application pattern, a cycle of the cyclical application pattern including a blocking period during which the blocking stimulus sufficient produce a reversible conduction block of at least a portion of the peripheral neural structure of the subject is applied at least intermittently, the blocking period coinciding at least in part with a first activity state in the subject; and a release period during which no blocking stimulus is applied, the release period coinciding at least in part with a second activity state in the subject; one or more instructions related to detecting the onset of the second activity state in the subject; and one or more instructions related to initiating a release period during which no blocking stimulus is applied responsive to detecting the onset of the second activity state in the subject.

In addition to the foregoing, various other method and/or system and/or signal bearing medium/program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2A is an illustration of conduction in nerve;

FIG. 2B is a cross-sectional view of the nerve illustrated in FIG. 2A;

FIG. 2C is an illustration of the effect of a complete conduction block in a nerve;

FIG. 2D is a cross-sectional view of the nerve illustrated in FIG. 2C;

FIG. 2E is an illustration of the effect of a partial conduction block in a nerve;

FIG. 2F is a cross-sectional view of the nerve illustrated in FIG. 2E;

FIG. 4 is a flow diagram of method of modulating neural activity;

FIG. 21 is a block diagram of a system including a signal-bearing medium bearing instructions related to operation of a neural modulation system.

DETAILED DESCRIPTION

Figure 1A:
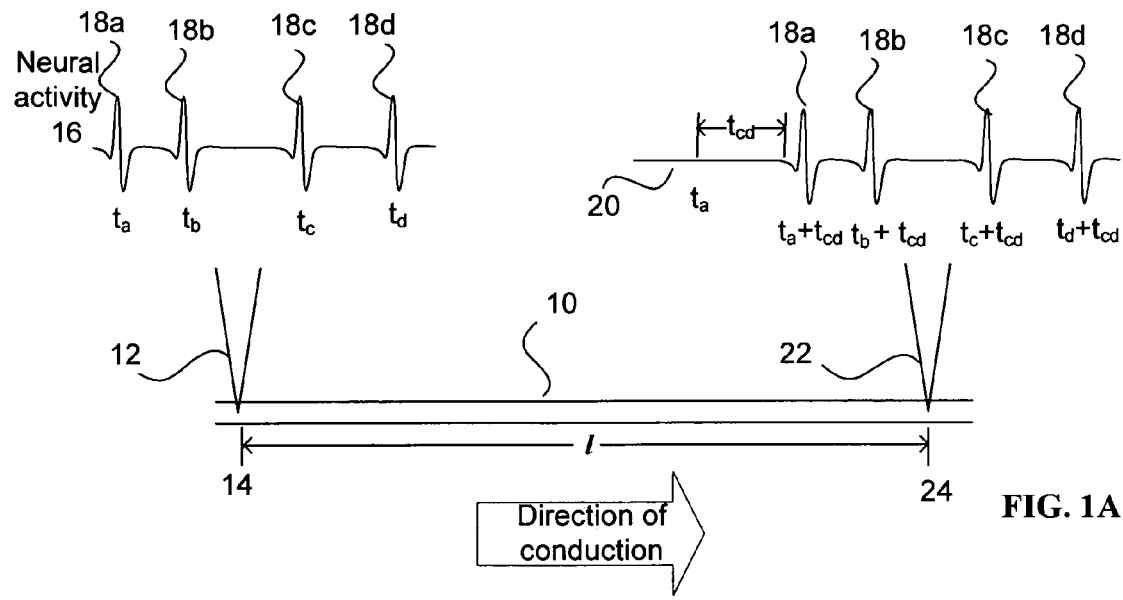
FIG. 1A is an illustration of conduction in a single nerve fiber.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Although the following terms are known in the art, they are generally defined below for the convenience of the reader:

Definitions

Central Nervous System (CNS)—the brain, spinal cord, optic nerves and retina.

Peripheral Nervous System (PNS)—all the nerves in the body that lie outside of the brain and spinal cord, i.e., the cranial nerves, spinal nerves, nerve plexuses, and their associated spinal and autonomic ganglia.

Autonomic Nervous System (ANS)—the portion of the nervous system that regulates involuntary body functions, including heart and circulation, respiration, digestion, temperature regulation, etc. The Autonomic nervous system includes two divisions, the sympathetic nervous system and the parasympathetic nervous system.

Sympathetic nervous system—the division of the autonomic nervous system, which, broadly speaking, functions to mobilize the body's energy and resources during times of stress and arousal to prepare for "fight or flight", e.g., it accelerates heart rate, constricts blood vessels, elevates blood pressure, etc.

Parasympathetic nervous system—the division of the autonomic nervous system that regulates body functions during relaxed states.

Neuron—a nerve cell, the basic functional unit of the nervous system. A neuron typically includes a cell body, and one or more processes called axons and dendrites.

Axon—An axon is a long slender process of a nerve cell that conducts electrical impulses away from the cell body.

Action Potential—a brief, regenerative change in membrane potential that propagates actively along membrane of neuron or other excitable cells.

Dendrite—A dendrite is a process of a nerve cell that conducts electrical impulses toward the cell body. Often, a neuron may have multiple, relatively short dendrites.

Nerve Fiber—The term "nerve fiber" may be used in connection with peripheral neurons to describe long slender processes (either axons or dendrites) that may conduct electrical impulses away from or toward the cell body.

Nerve—a cable-like bundle of multiple nerve fibers, capable of carrying signals between the central nervous system and other organs and tissues of the body. Cranial nerves may connect directly to parts of the brain.

Fascicle—a bundle of nerve fibers within a nerve. Each fascicle is surrounded by a dense sheath of tissue called perineurium, while a group of fascicles that make up a nerve are surrounded and held together by looser connective tissue called epineurium.

Nerve Plexus—a region of crossover and regrouping of nerve fibers from multiple nerves Ganglion—in the peripheral nervous system, a cluster of nerve cell bodies; sensory (afferent) ganglia lie along spinal column on the dorsal roots. Autonomic ganglia (containing the cell bodies of autonomic neurons) may lie parallel to the spinal column or in or near their target organs.

Spinal Root—root portion of spinal nerve, as it branches off of spinal cord and passes through bony canal through vertebra.

FIG. 1A depicts conduction of action potentials (referred to collectively as "neural activity") in a single nerve fiber 10 (an elongated nerve process, or axon or dendrite) when no conduction block is present. Neural activity may be sensed from nerve fiber 10 with an electrode 12 located at a first position 14 on nerve fiber 10. Sensed neural activity may be represented by trace 16, which includes action potentials 18*a*, 18*b*, 18*c* and 18*d* occurring at times $t_a$, $t_b$, $t_c$ and $t_d$. The direction of conduction of action potentials along nerve fiber 10 is indicated by the arrow. Trace 20, sensed with electrode 22 at a second position 24 located at a distance l from first position 14 on nerve fiber 10, includes action potentials 18*a*, 18*b*, 18*c* and 18*d* occurring at times $t_a+t_{cd}$, $t_b+t_{cd}$, $t_c+t_{cd}$ and $t_d+t_{cd}$, where $t_{cd}$ is the conduction delay time, or the time for the action potentials to conduct down nerve fiber 10 from first position 14 to second position 24. Conduction delay time $t_{cd}$ is equal to l/v, where l is the distance between first position 14 and second position 24 and v is the conduction velocity.

Figure 1B:
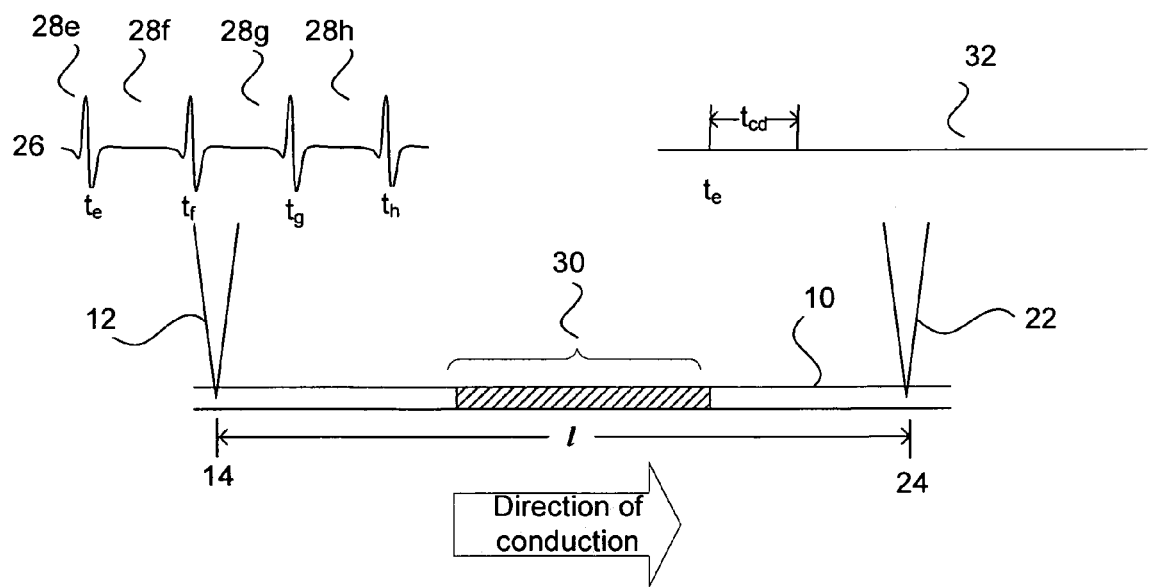
FIG. 1B is an illustration of conduction block in the single nerve fiber depicted in FIG. 1A.

FIG. 1B depicts the effect of a conduction block in nerve fiber 10, indicated by cross-hatching in blocked region 30. When conduction is blocked at region 30, action potentials 28*e*, 28*f*, 28*g* and 28*h* occurring at times $t_e$, $t_f$, $t_g$ and $t_h$ in trace 26 may be sensed with electrode 12 at first position 14. However, conduction of the action potentials in the direction indicated by the arrow is blocked so they cannot travel past region 30 to second position 24. Accordingly, trace 32, sensed with electrode 22 at second position 24, will not contain any action potentials.

FIGS. 2A-2F illustrate the effects of complete and partial conduction block on a nerve made up of multiple nerve fibers. A nerve 50 is shown in longitudinal section in FIG. 2A, and in cross section (taken at section line 2B-2B) in FIG. 2B. Nerve 50 contains multiple nerve fibers 54. An electrode 56 at first position 58 may record a compound signal 60 from nerve 50. Compound signal 60 is made up of the summation of action potentials produced by multiple individual nerve fibers. If the direction of conduction is as indicated by the arrow, an electrode 62 at second position 64 may record compound signal 66. Because action potentials on individual nerve fibers may travel at different conduction velocities, action potentials that sum to form compound signal 60 at first position 58 may not arrive at second position 64 at the same delays relative to each other. Accordingly, compound signal 66 may represent the summation of the same action potentials that made up compound signal 60, but because they arrive at position 64 at different relative delays, compound signal 66 may have a different shape than compound signal 60.

FIG. 2C depicts nerve 50 in longitudinal section, with a complete conduction block in region 70, as indicated by cross-hatching. Conduction block is indicated in region 74 in the cross-section of the same nerve, taken at section line 2D-2D and shown in FIG. 2D. Compound signal 75 sensed at position 58 is unchanged relative to compound signal 60 shown in FIG. 1A, but compound signal 76, sensed at position 64 with electrode 62, includes no activity, because conduction of action potentials was blocked in all fibers at the blocked region as indicated at 70 and 74.

FIG. 2E depicts nerve 50 with a partial conduction block in area 80 in longitudinal view, as indicated by cross-hatching. Conduction block is indicated by area 84 in the cross-section shown in FIG. 2F, taken along section line 2F-2F in FIG. 2E. Compound signal 85 sensed at position 58 is unchanged relative to compound signal 60 as shown in FIG. 2A, but compound signal 86, sensed at position 64 with electrode 62, is of lower amplitude because conduction of action potentials was blocked in the subset of fibers passing through the blocked region as indicated at areas 80 and 84. Accordingly, compound signal 86 is formed by the summation of action potentials from those fibers lying outside of area 80, i.e. fibers lying within region 88 in cross-section 82. As seen in cross-section 82, in "partial conduction" block of a nerve, a subset of the nerve fibers (lying within area 84) may be blocked, and another subset of the nerve fibers (lying within region 88) may conduct as usual. In the example shown in FIG. 2C, the blocked subset of nerve fibers falls within a particular spatial distribution. In some cases, a subset of nerve fibers within a nerve may be blocked based on fiber diameter, fiber type, presence of a biomarker, or other parameter instead of or in addition to the location of the nerve fiber with the nerve.

Blockage of conduction in peripheral nerves may be produced by application of appropriately configured electrical stimuli as just described, or by various other approaches as described elsewhere herein or as known to those of skill in the art.

Effects of peripheral nerve block depend at least in part on the type of nerve or nerve fibers blocked and the target organ or tissue innervated by the blocked nerve or nerve fibers. Modulation of peripheral neural activity may be used for various purposes, including, for example, modulating blood pressure and metabolic activity, controlling pain, and controlling activation of smooth and skeletal muscles (e.g. in micturation, FES, etc.). Elimination of activity from sensory neurons innervating the pancreas may prevent development of diabetes (see Razavi et al., "TRPV1+ sensory neurons control β cell stress and islet inflammation in autoimmune diabetes"; Cell; Dec. 15, 2006; pp. 1123-1135; Vol. 127, which is incorporated herein by reference in its entirety), and elimination of activity from sensory neurons innervating a limb or digit may prevent development of arthritis in the area innervated by the nerve (as described in Kane et al.; "Protective effect of sensory denervation in inflammatory arthritis: evidence of regulatory neuroimmune pathways in the arthritic joint; Ann. Rheum. Dis.; 2005; pp. 325-327; Vol. 64; originally published online 21 May 2004, which is incorporated herein by reference in its entirety).

While blocking of neural activity in some contexts may produce desirable and/or therapeutic effects, for example as described herein above, in some contexts blockage of nerve conduction may produce undesirable effects. For example, blockage of conduction in a motor nerve may cause decreased muscle force or control, while blockage of conduction in a sensory nerve may lead to decreased sensation and/or numbness. It is believed that, in some contexts, delivery of blocking stimuli coinciding at least in part with particular activity states in a subject may allow desired effects of blocking to be produced while limiting inconvenience, discomfort, and/or other undesired effects. Blocking stimuli may be delivered during periods of reduced activity of the subject (including, but not limited to, physical activity, physiological activity, or other measures of activity, in all or a portion of the body of the subject) in order to minimize discomfort, inconvenience, or other undesired effects.

Figure 3:
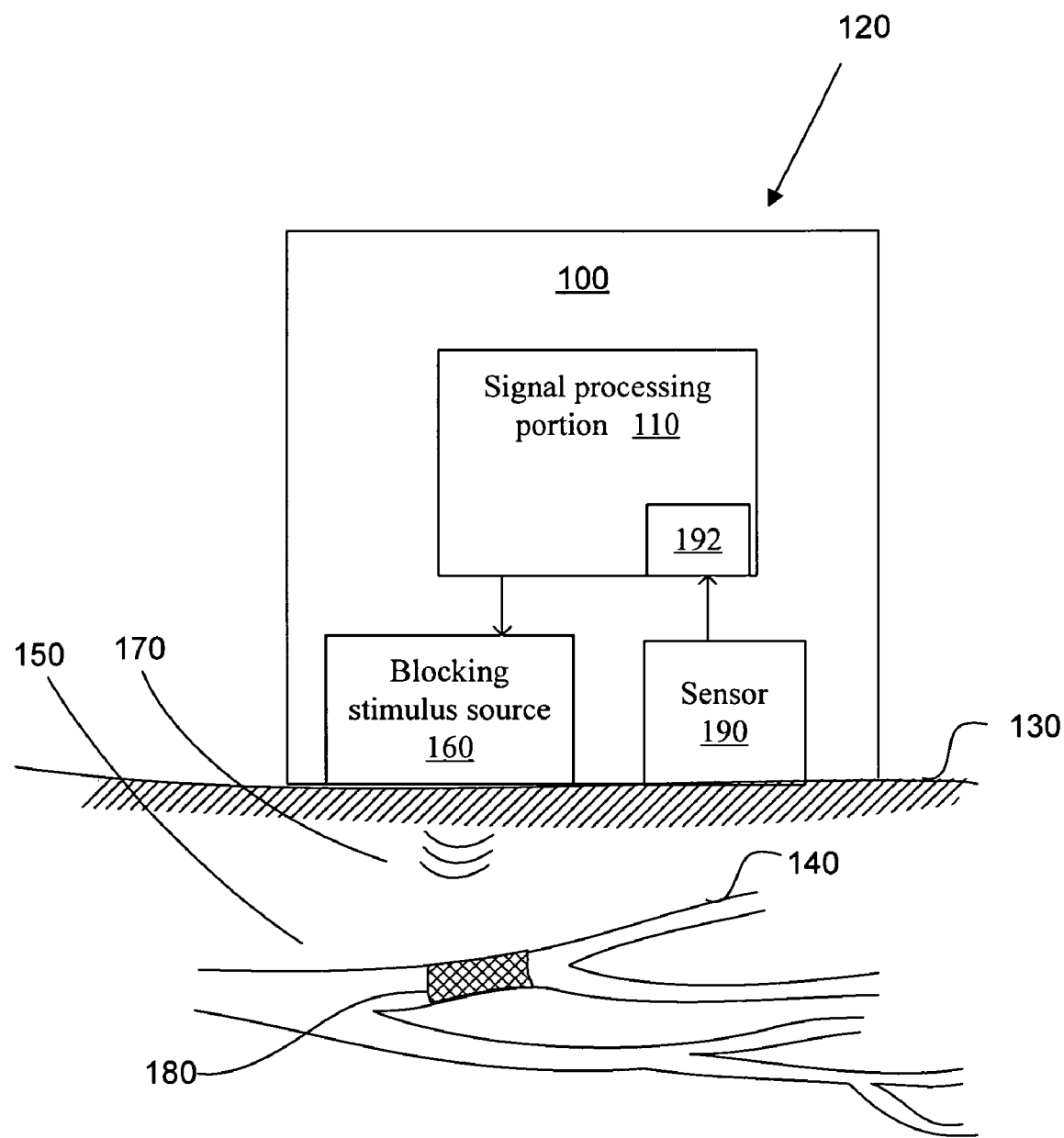
FIG. 3 is a schematic diagram of a system for producing conduction block in a peripheral neural structure.

FIG. 3 is a schematic diagram illustrating a system 100 for producing conduction block in a peripheral neural structure. A body portion of a subject is indicated generally at 120, including skin surface 130 overlying peripheral nerve 140 and surrounding tissue 150. System 100 includes blocking stimulus source 160, which is capable of generating blocking stimulus 170 to block conduction in region 180 of peripheral neural structure 140 (in this example, a peripheral nerve). Sensor 190 senses at least one parameter indicative of an activity state in the subject, which may be an overall activity level of the subject, or a level of use or activity of a body portion innervated by peripheral neural structure 140. A signal from sensor 190 is connected to input 192 of signal processing portion 110, and a signal for driving production of blocking stimulus 170 with blocking stimulus source 160 is produced by signal processing portion 110, based at least in part upon the activity state in the subject, as determined from the signal from sensor 190. Systems of the type depicted in FIG. 3 and described in greater detail subsequently may be used for modulating neural activity by blocking conduction in at least a portion of a peripheral neural structure.

An example of a method of modulating neural activity is outlined in FIG. 4. As shown at step 200, the method may include applying a blocking stimulus sufficient to produce a reversible conduction block of at least a portion of a peripheral neural structure of a subject with a cyclical application pattern. The application pattern may include a blocking period during which the blocking stimulus sufficient to produce a reversible conduction block of at least a portion of the peripheral neural structure of the subject is applied at least intermittently, the blocking period coinciding at least in part with a first activity state in the subject, and a release period during which no blocking stimulus is applied, the release period coinciding at least in part with a second activity state in the subject.

The term "activity state" refers to one of at least two possible categories of activity that are characterized by and distinguishable from each other by one or more quantifiable parameters. Activity may refer to overall activity of the subject or use or activity of a body portion innervated by the peripheral neural structure. Activity may include or be reflected by physical activity, physiological activity, or other measures or indicators of activity, as described in greater detail elsewhere herein.

In general, according to the present method, at least two activity states may be defined, with appropriate values or value ranges of the one or more quantifiable parameters associated therewith. The different activity states may differ with regard to the level of activity, or, in some cases, the nature of the activity. In some cases, the overall activity of the subject may be lower in the first activity state than in the second activity state. For example, the first activity state may be a "sleep state" and the second activity state may be a "waking state." Alternatively, the first activity state may be a "resting," "lying down" or "sitting" activity state while the second activity state may be a "moving about," "standing" or "walking" activity state.

The activity or use of a specific portion of the subject's body, rather than the overall activity of the subject, may be of interest. For example, the first and second activity states may be defined such that the use of a body portion innervated by the peripheral neural structure by the subject is lower in the first activity state than in the second activity state. If the body portion innervated by the peripheral neural structure is the subject's arm, a low use state may be obtained when the arm is resting in the subject's lap, on an arm rest or table top, or in a sling, while the subject stands or walks. Low use or activity of the subject's arm may also be obtained while the overall activity of the subject is low, e.g. the subject is lying down or sleeping. Conversely, a moderate or high use or activity state of a body portion, e.g., the subject's arm, may be obtained while the subject's overall activity level is either high or low. For example, the subject could use the arm for writing, typing, holding a book, knitting, etc. while sitting quietly with a generally low overall activity level. A subject may also have a high use or activity state of the arm in combination with an overall high activity level.

Figure 5:
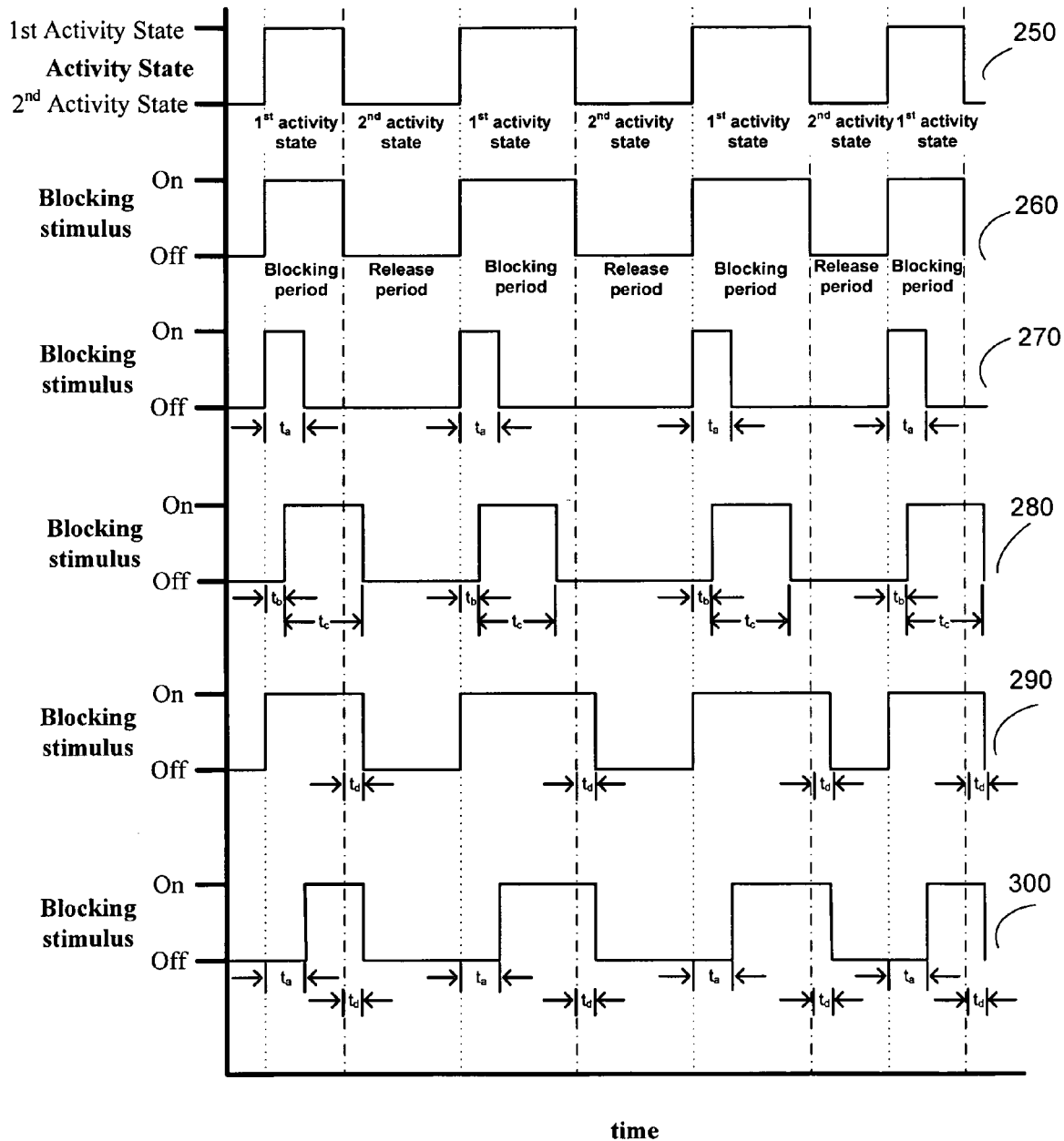
FIG. 5 is an illustration of application patterns for blocking stimuli.

Examples of representative cyclical patterns for application of blocking stimuli are illustrated in FIG. 5. A cyclical application pattern may include a blocking period during which the blocking stimulus sufficient to produce a reversible conduction block of at least a portion of the peripheral neural structure of the subject is applied at least intermittently and a release period during which no blocking stimulus is applied. The blocking period coincides with the first activity state in the subject and the release period coincides at least in part with a second activity state in the subject.

Trace 250 in FIG. 5 illustrates the activity state in a subject, which may be an overall activity state or an activity or use state of at least a portion of the body of the subject, as discussed above. In this example, the activity in the subject is classified into one of two possible activity states, a first activity state and a second activity state. Trace 260 depicts a blocking stimulus pattern that corresponds directly to the activity state, with blocking stimulus applied ("on") while the subject is in the first activity state and the blocking stimulus removed ("off") while the subject is in the second activity state. Trace 270 depicts a blocking stimulus pattern in which a blocking stimulus is applied at the onset of the first activity state and removed after a time $t_a$ after the onset of the first activity state. Trace 280 depicts a blocking stimulus pattern in which a blocking stimulus is applied at a time $t_b$ after the onset of the first activity state and removed at a time $t_c$ after was applied. In this example, the period during which the blocking stimulus is applied or "on" may extend into the second activity state in the subject. Trace 290 depicts a blocking stimulus pattern in which a blocking stimulus is applied (turned "on") at the onset of the first activity state in the subject. The blocking stimulus is removed (turned "off") at a time $t_d$ after the end of the first activity state and onset of the second activity state. Trace 300 depicts a blocking stimulus pattern in which a blocking stimulus is applied at a time $t_a$ after the onset of the first activity state, and removed at a time $t_d$ after the end of the first activity state and onset of the second activity state.

In some embodiments of the method as described herein, the cyclical application pattern may be repeated at a rate of one cycle per day. For example, the blocking stimulus may be applied for a blocking period each night while the subject is sleeping. Other rates of repetition may be used, without limitation. For example, in some applications it may be preferable to repeat the cyclical application pattern twice a day, on alternating days, every three days, once a week, and so forth.

The cyclical application pattern may be repeated for a duration or period that is expected or determined to produce a desired effect. For example, the cyclical application pattern may be repeated over a period of time sufficient to produce modulation of an immune response. In another example, the cyclical application pattern may be repeated over a period of time sufficient to produce modulation of an inflammatory response. In a further embodiment, the cyclical application pattern may be repeated over a period of time sufficient to produce modulation of a metabolic response.

For example, modulation of a metabolic response using a method or system as described herein, including the materials incorporated herein by reference, may involve the provision of total or partial blocking stimulus to TRPV1(+) neurons innervating the pancreas. Such stimulus would effectively reduce or eliminate the TRPV1(+) neural activity preventing T-cell mediated death of pancreatic beta cells.

As a further example, modulation of an immune response using a method or system as described herein may involve the provision of total or partial blocking stimulus to sensory nerves innervating an inflamed or damaged region. See, for example, Pham-Marcou et al., "Effect of neurolytic nerve block on systemic carrageenan-induced inflammatory response in mice," British Journal of Anaesthesia 95(2): 243-246, (2005), doi:10.1093/bja/aei150, Advance Access publication Apr. 29, 2005, which is incorporated herein by reference in its entirety.

Modulation of an inflammatory response using a method or system as described herein, including the materials incorporated herein by reference, may involve the provision of total or partial blocking stimulus to a sensory nerve innervating a limb, join, or digit, e.g. as described in Kane et al., "Protective effect of sensory denervation in inflammatory arthritis (evidence of regulatory neuroimmune pathways in the arthritic joint)," Ann Rheum Dis 2005; 64:325-327. doi: 10.1136/ard.2004.022277, which is incorporated herein by reference in its entirety.

Figure 6:
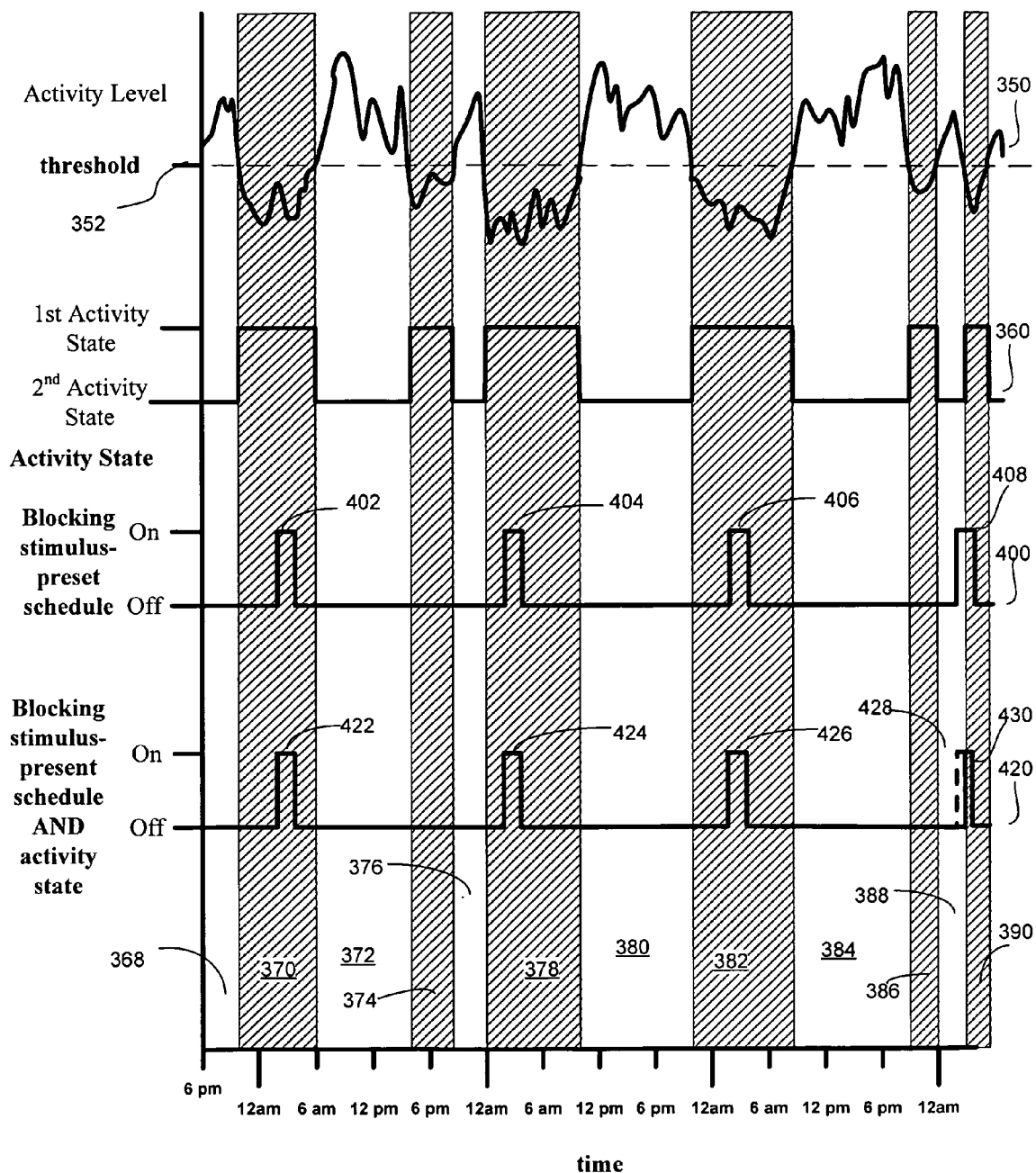
FIG. 6 is an illustration of further application patterns for blocking stimuli.

Trace 350 in FIG. 6 is an illustration of a sensed activity of the type that might be detected from a subject over the course of several days, with times marked along the x-axis. Trace 350 does not represent any specific type of signal (it could be, for example, a physiological signal such as a heart rate or respiration rate, or a physical signal such as motion detection or pressure signal). It is assumed that higher values of the signal indicate that the subject is awake and active and lower values of the signal indicate that the subject is resting. By setting an appropriate threshold value, as indicated at 352, it may be possible to distinguish between the awake/active state (during which the value of trace 350 is above the threshold value) and the resting state (during which the value of trace 350 is below the threshold value). Trace 360 indicates the activity state of the subject as thus determined. The activity state of the subject is also indicated in FIG. 6 by shaded regions that denote periods of reduced activity (e.g., sleep) and unshaded areas that denote periods of activity or wakefulness. As can be seen, the subject is usually sleeping or resting at night, as represented by shaded areas 370, 378, 382, 386, and 390, and awake or active during the day, as represented by unshaded areas 368, 372, 380, and 384, but sometimes rests during the day (shaded area 374) or is awake in the late evening (unshaded area 376) or very early the morning (unshaded area 388).

A blocking stimulus may be applied with a cyclical application pattern according to a detected signal indicative of at least one activity state in the subject, where the at least one activity state of the subject has a substantially cyclical expected pattern of occurrence. For example, if the application pattern is based on detection of a sleep state in a subject, in most cases it may reasonably be assumed that application pattern will be cyclical, since the subject's sleep pattern is substantially cyclical with a one day cycle time. However, variations in the cycle may sometimes occur, as illustrated in trace 360 of FIG. 6.

In some embodiments, a blocking stimulus may be applied with a cyclical application pattern according to a pre-set schedule. Trace 400 represents a blocking stimulus delivered according to a pre-set schedule. In this example, the blocking stimulus is turned "on" every 24 hours, from 2 am-4 am, as indicated at 402, 404, 406, and 408. As can be seen, such an application pattern will normally coincide with a sleep state in the subject (i.e., at 402, 404, 406). However, as indicated at 408, a blocking stimulus delivered according to a pre-set schedule may occasionally coincide with a waking/active state rather than a rest/sleep state.

In some embodiments the cyclical application pattern may be determined in part by a pre-set schedule and in part by a sensed activity state. Either a pre-set schedule or sensed activity state may be set as the default, with the possibility to override the default in case of conflicts. The specific configuration may be selected depending on the needs of the particular subject. In one example, as depicted in trace 420 in FIG. 6, a blocking stimulus may be applied cyclically every night based on a pre-set schedule as a default, e.g. as indicated at 422, 424 and 426. However, blocking stimulus application may be overridden if the subject is not asleep at night as expected, as determined by sensing the activity state of the subject. At 428 in FIG. 6, for example, the subject is not asleep so the blocking stimulus is not delivered at the scheduled time (indicated by dashed line). However, the blocking stimulus may be applied for the remaining portion of its scheduled delivery time if the subject returns to sleep (e.g., as shown at 430). Similarly, if the subject is asleep at the scheduled time for blocking stimulus application, as expected, but awakens during the scheduled blocking period, blocking stimulus application may be terminated earlier than scheduled, in response to the change in the activity state of the subject.

In a related embodiment, a blocking stimulus may be applied based on detection of a sleep state, operating on the assumption that sleep will occur nightly. However, if a sleep state is detected during the day (i.e., during a day-time nap) blocking stimulus application may be overridden because the sleep state is not occurring at night as expected.

Figure 7:
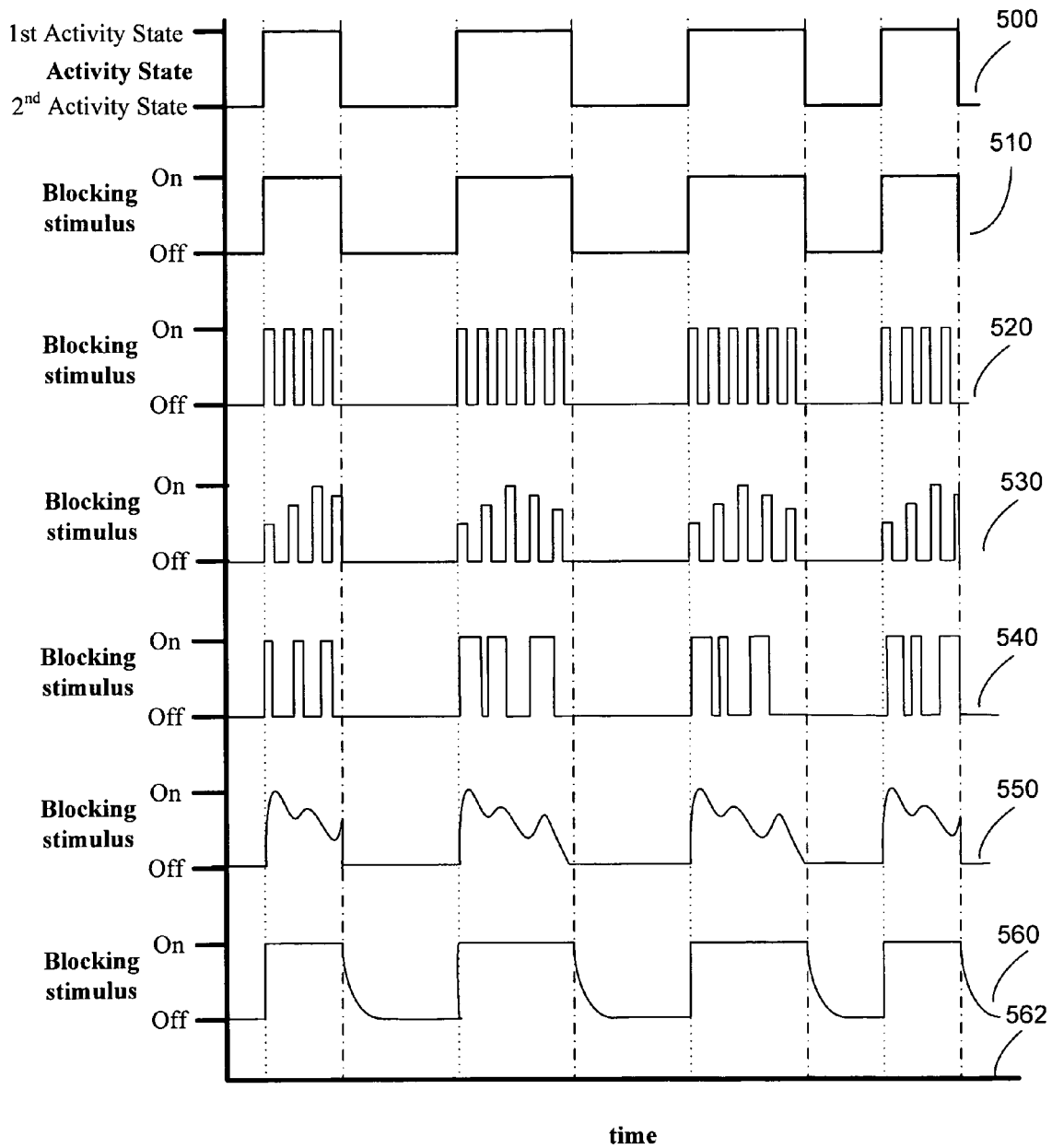
FIG. 7 is an illustration of types of blocking stimuli.

In some embodiments, a blocking stimulus sufficient to produce a reversible conduction block of at least a portion of a peripheral neural structure of a subject may be applied substantially continuously during the blocking period. See, for example, FIG. 7. Trace 500 of FIG. 7 represents the activity state of a subject as a function of time, as indicated on axis 562. Trace 510 depicts an example of a blocking stimulus that is applied substantially continuously during each blocking period, with the blocking periods corresponding to occurrences of a first activity state, as indicated in trace 500.

In other embodiments, a blocking stimulus sufficient to produce a reversible conduction block of at least a portion of a peripheral neural structure of a subject may be applied intermittently during the blocking period. For example, a blocking stimulus sufficient to produce a reversible conduction block of at least a portion of a peripheral neural structure of a subject may be applied intermittently at a fixed repetition rate during the blocking period. Traces 520 and 530 in FIG. 7 are two examples of blocking stimuli applied intermittently during the blocking period. Blocking stimuli may include different combinations of pulse duration, pulse amplitude, pulse frequency, duty cycle, etc. In trace 530, pulse amplitude varies over time during the blocking period. In trace 540 pulse duration and interval vary over time during the blocking period. In some embodiments, the blocking stimulus may be applied according to a programmed pattern during at least a portion of the blocking period. The programmed pattern may specify a blocking stimulus amplitude that varies over time during the blocking period, as depicted in trace 550. In addition, a programmed pattern may specify application of blocking stimulus pulses intermittently during the blocking period in which the amplitude of the stimulus pulses varies over time during the blocking period, as illustrated in trace 530, or in which one or both of the duration of the stimulus pulses or interval between the stimulus pulses varies over time during the blocking period, as illustrated in trace 540.

Various configurations of stimulus may be used; while for simplicity rectangular pulses have been depicted in most of the figures, the pulse may ramp up gradually when it is applied, and/or may decay gradually when removed, as depicted in Trace 560 of FIG. 7, or may have various other waveforms, as illustrated in trace 550.

A blocking stimulus sufficient to produce a reversible conduction block of at least a portion of a peripheral neural structure of a subject may be applied with a cyclical application pattern having a period of about one day. A blocking stimulus sufficient to produce a reversible conduction block of at least a portion of a peripheral neural structure of a subject may be applied with a cyclical application pattern for a fixed number of cycles, or for a fixed duration.

A blocking stimulus sufficient to produce a reversible conduction block of at least a portion of a peripheral neural structure of a subject may be sufficient to produce substantially complete blockage of conduction in the peripheral neural structure of the subject, i.e. to produce substantially complete blockage of all fibers, of all types and sizes, and at all positions, e.g. as illustrated in FIG. 2B. In some embodiments, applying a blocking stimulus sufficient to produce a reversible conduction block of at least a portion of a peripheral neural structure of a subject with a cyclical application pattern may include applying a blocking stimulus sufficient to produce blockage of a subset of nerve fibers in the peripheral neural structure of the subject, e.g. as illustrated in FIG. 2C. The blocked subset of nerve fibers may include fibers within a selected diameter range, within a selected spatial distribution within the peripheral neural structure of the subject (as shown in the example of FIG. 2C), or within selected fascicles within the peripheral neural structure of the subject.

Various methods of exciting or blocking nerve fibers selectively with respect to fiber diameter, location within a nerve or nerve bundle, or within a fascicle are described, for example, in Tarler and Mortimer ("Selective and independent activation of four motor fascicles using a four contact nerve-cuff electrode"; 2004; IEEE Trans. Neural Syst. Rehab. Eng."; Vol. 12; pp. 251-257), Vessela et al. ("Peripheral nerve magnetic stimulation: influence of tissue non-homogeneity" Bio-Medical Engineering OnLine; 23 Dec. 2003; located at: http://www.biomedical-engineering-online.com/content/2/1/19), Olree and Horch ("Differential activation and block of peripheral nerve fibers by magnetic fields"; Muscle & Nerve; 2006; pp. 189-196; Vol. 34, Wiley Periodicals), and U.S. Pat. No. 5,540,730, all of which are fully incorporated herein by reference.

Figure 8:
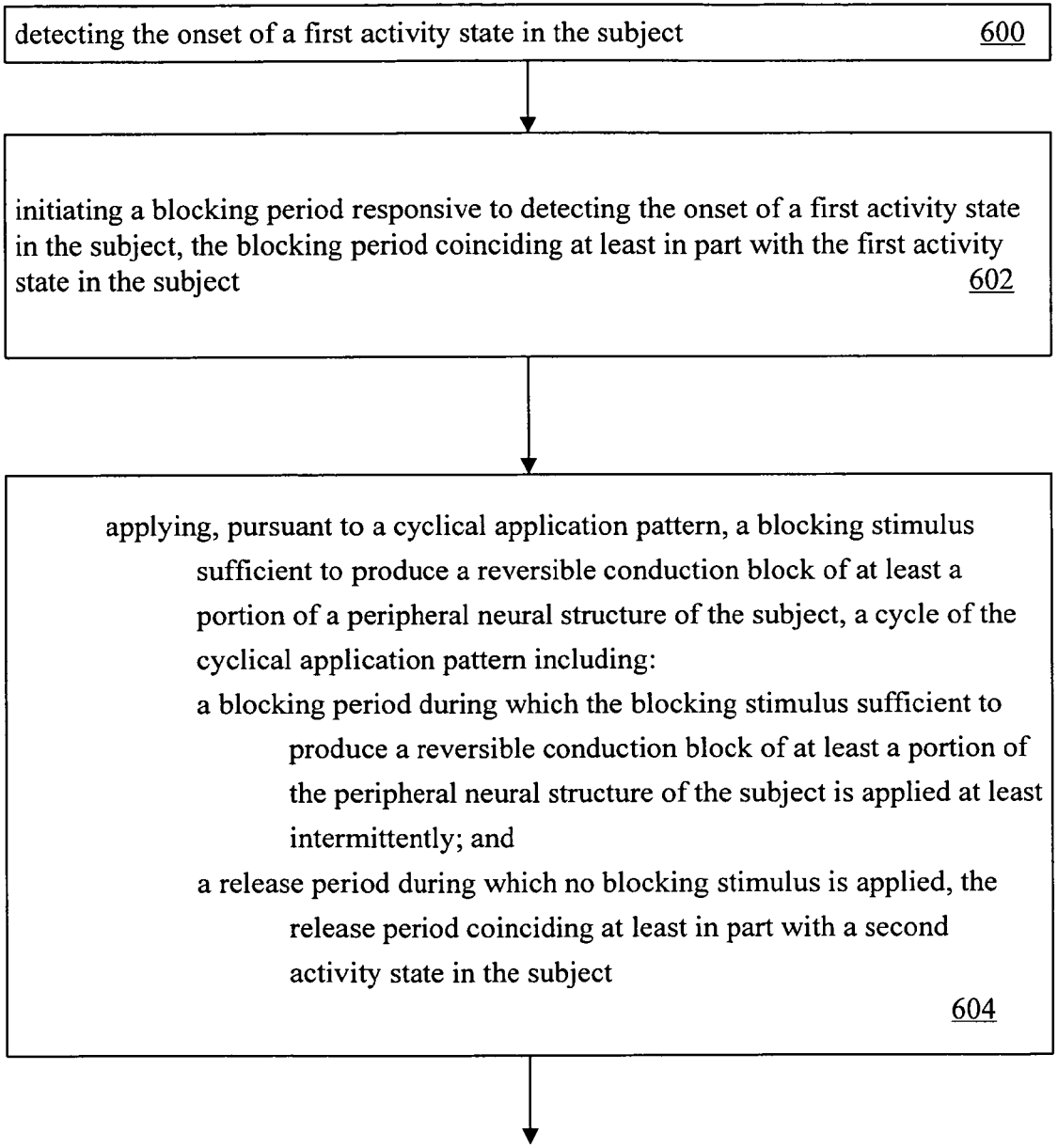
FIG. 8 is a flow diagram of a method of modulating neural activity.

In another embodiment, as shown in FIG. 8, a method of modulating neural activity may include detecting the onset of a first activity state in the subject, as shown at step 600; initiating a blocking period responsive to detecting the onset of a first activity state in the subject, the blocking period coinciding at least in part with the first activity state in the subject, as shown at step 602; and applying, pursuant to a cyclical application pattern, a blocking stimulus sufficient to produce a reversible conduction block of at least a portion of a peripheral neural structure of the subject, a cycle of the cyclical application pattern including a blocking period during which the blocking stimulus sufficient to produce a reversible conduction block of at least a portion of the peripheral neural structure of the subject is applied at least intermittently; and a release period during which no blocking stimulus is applied, the release period coinciding at least in part with a second activity state in the subject, as shown at step 604.

Initiation of the blocking period and the release period may be made dependent on various factors. In some embodiments, the method may include initiating the blocking period substantially immediately upon detecting the onset of a first activity state in the subject (for example as illustrated in FIG. 5, traces 260, 270 and 290). Alternatively, the blocking period may be initiated at a delay interval after detecting the onset of a first activity state in the subject (for example, as illustrated FIG. 5, traces 280 and 300).

The release period during which no blocking stimulus is applied may be initiated after an interval determined relative to the initiation of the blocking period, in order to provide a blocking period of fixed duration (for example, as depicted in FIG. 5, traces 270 and 280). Alternatively, the release period may be initiated responsive to detecting the onset of a second activity state in the subject. The release period may be initiated substantially immediately upon detecting the onset of the second activity state in the subject, as illustrated in FIG. 5, trace 260, or at a delay interval after detecting the onset of the second activity state in the subject, as illustrated in FIG. 5, traces 290 and 300.

The method may include initiating a release period during which no blocking stimulus is applied responsive to detecting an override signal. In general, the override signal may be indicative of any type of circumstance under which it is no longer desirable to apply the blocking stimulus, for reasons that include but are not limited to reasons of safety, comfort, or convenience. The override signal may be indicative of a condition of the body of the subject, or indicative of a condition external to the body of the subject (e.g., in the environment of the subject). In some cases the override signal may be detected from a user input device, and may indicate the desire of a user to discontinue blocking and initiate a release period.

Figure 9:
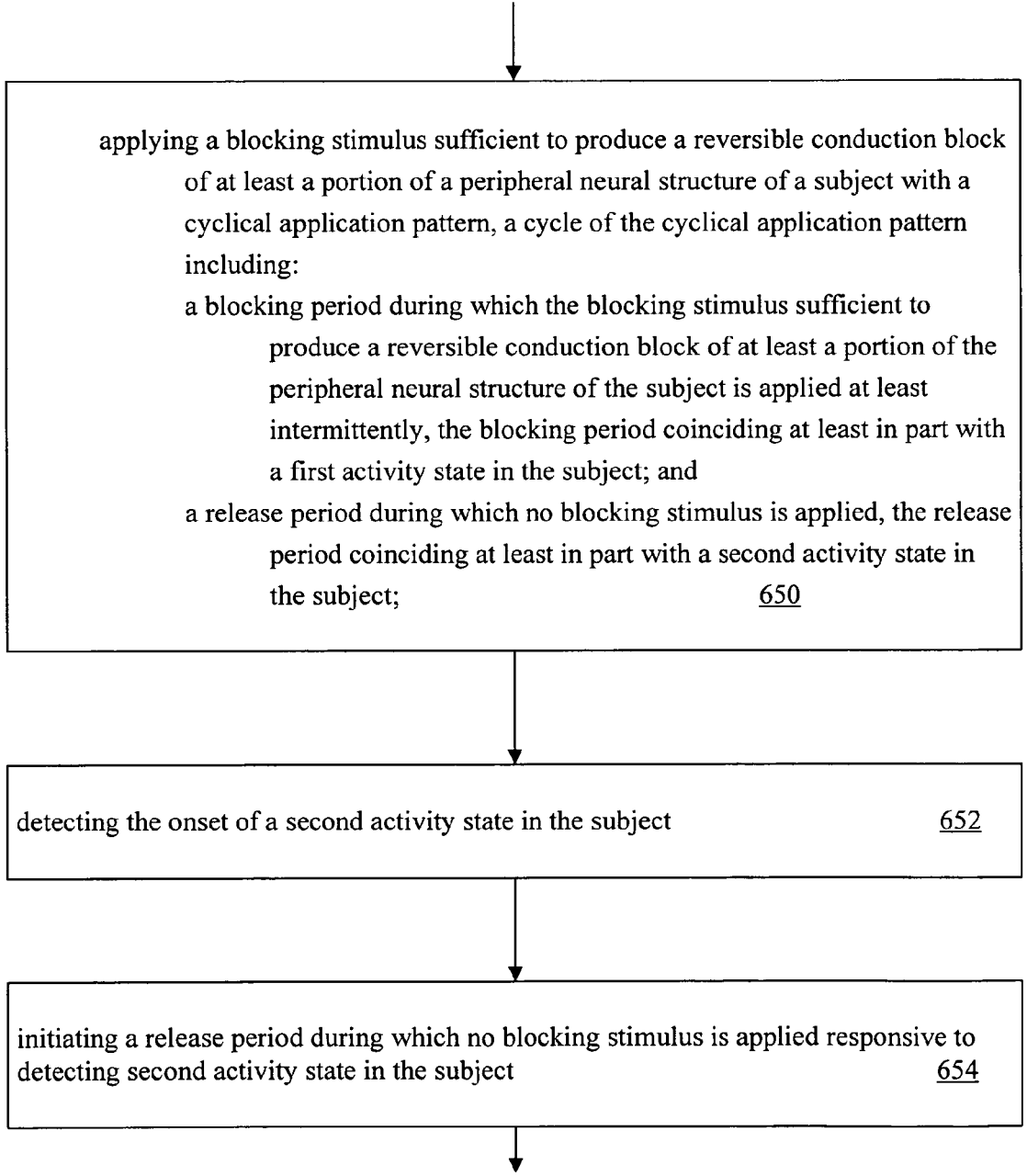
FIG. 9 is a flow diagram of a method of modulating neural activity.

In a related embodiment, as shown in FIG. 9, a method of modulating neural activity may include applying a blocking stimulus sufficient to produce a reversible conduction block of at least a portion of a peripheral neural structure of a subject with a cyclical application pattern, a cycle of the cyclical application pattern including: a blocking period during which the blocking stimulus sufficient to produce a reversible conduction block of at least a portion of the peripheral neural structure of the subject is applied at least intermittently, the blocking period coinciding at least in part with a first activity state in the subject; and a release period during which no blocking stimulus is applied, the release period coinciding at least in part with a second activity state in the subject, as indicated at step 650; detecting the onset of a second activity state in the subject, as indicated at step 652; and initiating a release period during which no blocking stimulus is applied responsive to detecting second activity state in the subject, as indicated at step 654. Traces 260, 290 and 300 of FIG. 5 are examples of blocking stimuli that fit this pattern, however, it should be noted that this pattern is not limited to cases in which the blocking period occurs at a fixed latency relative to onset of the first activity state. The method may include initiating the release period substantially immediately upon onset of a second activity state in the subject (as in plot 260 of FIG. 5), or at a delay interval after detecting the onset of a second activity state in the subject, as depicted in plots 290 and 300 of FIG. 5.

Figure 10:
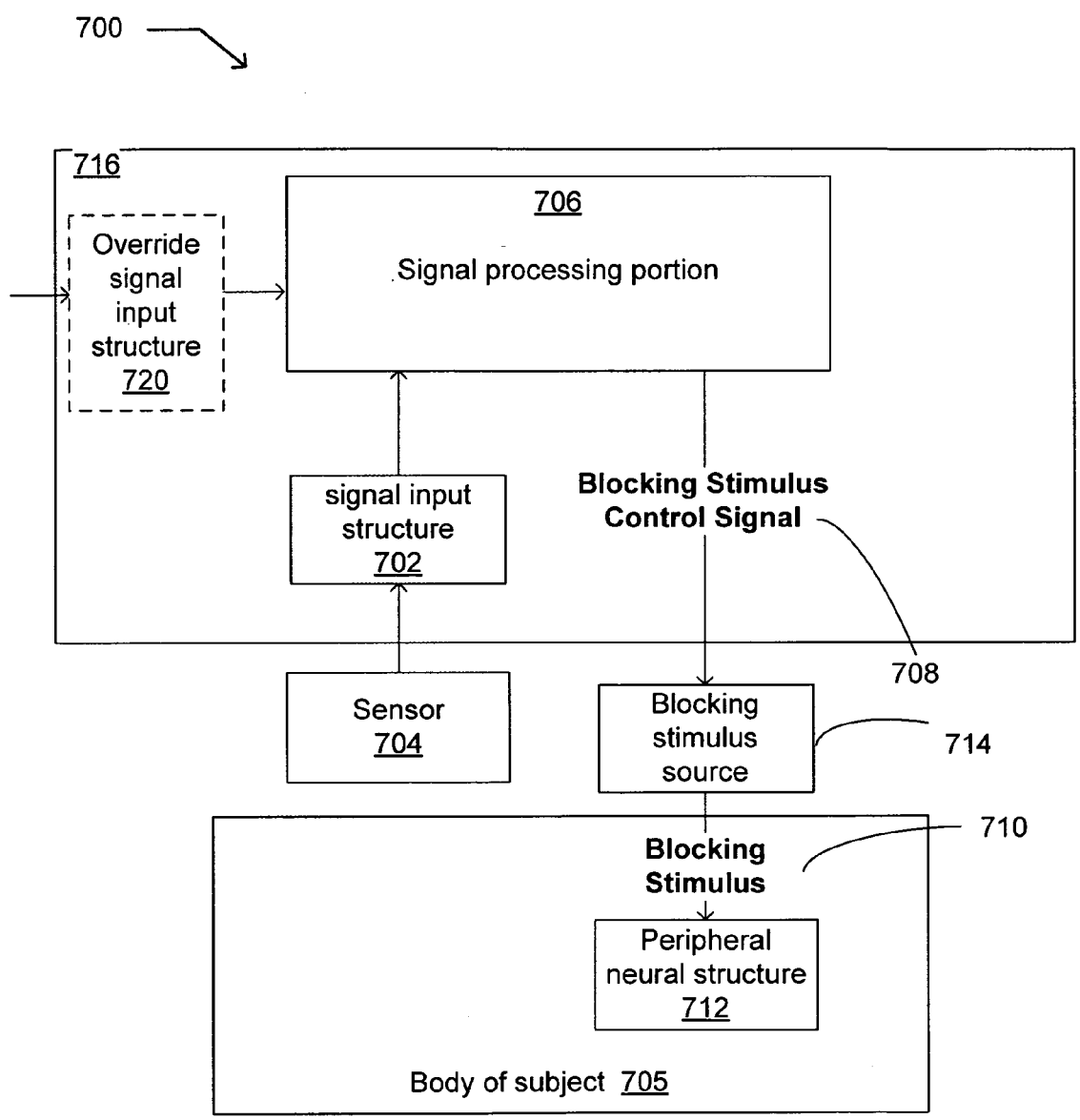
FIG. 10 is a block diagram of an example of a neural modulation system.

Methods of neural modulation as described herein may be implemented with a neural modulation system 700 as illustrated generally in FIG. 10. Basic components of neural modulation system 700 include a signal input structure 702, sensor 704, and signal processing portion 706. Signal input structure 702 may be operatively connected to sensor 704 and configured to receive a signal indicative of an activity state of at least a portion of a body of a subject 705 innervated by a peripheral neural structure. Signal input structure 702, and other signal input structures described elsewhere herein, may be of various types configured to accept or receive signals of various types. Such signal input structures are known to those of skill in the art, and may include, but are not limited to, analog or digital inputs capable of accepting or receiving electrical, optical, acoustic, electromagnetic, or other types of signals. Signals may be accepted or received at a signal input structure through direct physical contact (e.g., an electrical contact), or by reception of a signal transmitted through or across a medium (e.g., via an inductive, optical, or electromagnetic link). Sensor 704 may be operatively connected to the signal input structure 702 and configured to generate the signal indicative of an activity state of the at least a portion of the body of the subject 705 innervated by the peripheral neural structure responsive to an activity of the at least a portion of the body of the subject 705. Signal processing portion 706 may be configured to distinguish a first activity state of the at least a portion of the body of the subject innervated by the peripheral neural structure from a second activity state of the at least a portion of the body of the subject 705 innervated by the peripheral neural structure at least partially based on the signal received by the signal input structure 702 and generate a blocking stimulus control signal 708 for driving production of a blocking stimulus 710 configured to reversibly block conduction in the peripheral neural structure 712 of the subject during at least a portion of the first activity state. Blocking stimulus control signal 708 may drive production of blocking stimulus 710 by blocking stimulus source 714, which may be responsive to the blocking stimulus control signal to produce the blocking stimulus 710 configured to reversibly block conduction in the peripheral neural structure 712 of the subject during the at least a portion of the first activity state.

For example, in the system 700 depicted in the example of FIG. 10, signal processing portion 706 and signal input structure 702 may be packaged together in package 716 and sensor 704 and blocking stimulus source 714 may be packaged separately.

In some embodiments, blocking stimulus source 714 or portion thereof may be located outside the body of the subject, and the blocking stimulus may pass through the skin and underlying tissue to reach the neural structure that is to be blocked. In other embodiment, a blocking stimulus source may be positioned within the body of the subject (either permanently or temporarily). Suitable positioning of the blocking stimulus source will depend upon the type of blocking stimulus source being used and the type and location of the neural structure to be blocked.

In some embodiments, a blocking stimulus source may be implanted within the body of a subject. For example, electrical current may be delivered via a tripolar arrangement of ring electrodes in insulating cuff, as described in van den Honert et al. ("A technique for collision block of peripheral nerve: single stimulus analysis"; IEEE Transactions on biomedical engineering, May 1981; pp. 373-378; Vol. BME-28), which is incorporated herein by reference in its entirety. Electrical blocking stimuli may be delivered with other types of implantable electrodes, including ring or spiral electrodes designed to fully or partially encircle a nerve, or electrodes designed to be positioned adjacent a nerve. Implanted electrodes may be connected to a power source within or external to the body of the subject, via a wired or wireless connection (see, e.g. US 2006/0190053, which is incorporated herein by reference in its entirety.)

High frequency alternating current delivered, for example, with one or more electrodes, may be used to produce blocking of neural structures. See, for example, Kilgore and Bhadra ("Nerve conduction block utilizing high-frequency alternating current"; Medical & Biological Engineering & Computing; 2004; pp. 394-406; Vol. 42), Zhang et al. ("Simulation analysis of conduction block in Myelinated axons induced by high-frequency biphasic rectangular pulses"; IEEE Transactions on Biomedical Engineering; July 2006; pp. 1433-1436; Vol. 53, No. 7), Zhang et al. ("Mechanism of nerve conduction block induced by high-frequency biphasic electrical currents"; IEEE Transactions on Biomedical Engineering; December 2006; pp. 2445-2454; Vol. 53, No. 12.), and Tai et al. ("Simulation analysis of conduction block in unmyelinated axons induced by high-frequency biphasic rectangular electrical currents"; IEEE Transactions on Biomedical Engineering; July 2005; pp. 1323-1332; Vol. 52, No. 7), all of which are incorporated herein by reference in their entirety.

Surface electrodes placed on the skin of a subject over a neural structure may be used to stimulate or block a neural structure, e.g. as described in Bostock et al. ("Threshold tracking techniques in the study of human peripheral nerve"; Muscle & Nerve; February 1998; pp. 137-158), which is incorporated herein by reference in its entirety.

Other sources for blocking and/or excitatory stimuli include thermal sources, which may be made implanted or placed on the body surface (for neural structures located sufficiently near the body surface). For example, cooling devices such as Peltier devices or liquid heat-transfer devices may be used to block neural conduction, as described in U.S. Pat. Nos. 6,746,474; 6,364,899; and 6,248,126; which are incorporated fully herein by reference. Nerves may be activated by thermal stimulation, which may be produced by a resistive element, by low intensity pulsed infrared (IR) light, for example, as described in Wells et al. ("Biophysical mechanisms of transient optical stimulation of peripheral nerve; Biophysical Journal; October 2007; pp. 2567-2580; Volume 93) and Wells et al. ("Pulsed laser versus electrical energy for peripheral nerve stimulation"; Journal of Neuroscience Methods; 2007; Vol. 163; pp. 326-337), which are incorporated fully herein by reference, by appropriately configured Peltier devices, or by other heating elements as known to those of skill in the art.

Various chemical agents may also be used to block nerve conduction. Examples of nerve blocking agents include local anesthetics (e.g. amino esters such as Benzocaine, Chloroprocaine, Cocaine, Procaine, and Tetracaine/Amethocaine, and amino amides such as Bupivacaine, Levobupivacaine, Lidocaine/Lignocaine, Mepivacaine, Prilocaine, Ropivacaine, Articaine, and Trimecaine), tricyclic antidepressants (e.g. amitriptyline), neurotoxins (e.g. tetrodotoxin, saxitoxin), or any other agent that blocks nerve conduction. See "Local anaesthetics and nerve conduction," The Virtual Anaesthesia Textbook, (http://www.virtual-anaesthesia-textbook.com), which is incorporated herein by reference in its entirety. Further examples of chemical agents include Anticholinergics, including Muscarinic receptor antagonists (e.g. Belladonna alkaloids such as Atropine (D/L-Hyosycamine) and Scopolamine (L-Hyoscine) or Synthetic and Semisynthetic substances such as Dicyclomine, Flavoxate, Ipratropium, Oxybutynin, Pirenzepine, Tolterodine, Tropicamide) and Nicotinic receptor antagonists (e.g., Ganglionic blocking agents such as Trimethaphan; Nondepolarizing neuromuscular blocking agents such as Atracurium, Doxacurium, Mivacurium, Pancuronium, Tubocurarine, Vecuronium; or Depolarizing neuromuscular blocking agents such as Suxamethonium chloride). Chemical agents may also include Beta Blockers, including Non-selective agents (e.g., Alprenolol, Carteolol, Levobunolol, Mepindolol, Metipranolol, Nadolol, Oxprenolol, Penbutolol, Pindolol, Propranolol, Sotalol, or Timolol), β1-Selective agents (e.g., Acebutolol, Atenolol, Betaxolol, Bisoprolol[16], Esmolol, Metoprolol, or Nebivolol), Mixed α1/β-adrenergic antagonists (e.g., Carvedilol, Celiprolol, or Labetalol), or β2-Selective agents (e.g. Butaxamine). Still other chemical agents include analgesics, such as Paracetamol, NSAIDs (non-steroidal anti-inflammatory drugs), COX-2(cyclooxygenase-2) inhibitors, and Opiates and morphinomimetics such as codeine, oxycodone, hydrocodone, diamorphine, pethidine. Still other chemical agents may include Benzodiazepines, e.g., alprazolam (Xanax), bromazepam (Lexotanil or Lexotan), chlordiazepoxide (Librium), clonazepam (Klonopin), diazepam (Valium), estazolam (ProSom), flunitrazepam (Rohypnol), flurazepam (Dalmane), lorazepam (Ativan), lormetazepam (Loramet), mexazolam (Sedoxil), midazolam (Dormicum), nitrazepam (Mogadon), oxazepam (Serax), temazepam (Restoril), or triazolam (Halcion). Aside from the main neurotransmitters of the peripheral nervous system, acetylcholine and noradrenaline, other neurotransmitters exiest, jointly labeled Non-noradrenergic, non-cholinergic (NANC) transmitters, and drugs that alter their effects may also be used as chemical agents to block neural activity. Examples of such transmitters include non-peptides (e.g., adenosine triphosphate, gamma-amino butyric acid, dopamine, nitric oxide), and peptides (e.g., neuropeptide Y, vasoactive intestinal peptide, gonadotropin releasing hormone, Substance P and calcitonin gene-related peptide.)

Chemical blocking agents may be delivered locally to a neural structure, e.g. with an implantable pump, as described in U.S. Pat. No. 6,978,174, which is herein by reference in its entirety. See also U.S. Pat. No. 7,162,303, which is incorporated herein by reference in its entirety. Chemical agents may be used singly or in combination with other chemical agents. See, for example, Walsh et al. ("Reversible conduction block produced by lipid-insoluble quaternary ammonium ions in cetyltrimethylammonium bromide-treated nerves"; Am. J. Physiol; 1959; pp. 547-550; Vol. 197.), which is incorporated herein by reference in its entirety. Some chemicals or combinations of chemical may selectively block certain types of neurons. (e.g., nociceptors, as described in "Treatment blocks pain without disrupting other functions"; Physorg.com; Oct. 3, 2007 http://www.phvsorg.com/news110637008.html, which is incorporated herein by reference in its entirety), sympathetic neurons, parasympathetic neurons, or other neuron types for which a characteristic biomarker can be identified).

Some chemical agents may be delivered topically to the skin of the subject to block neural structures. Examples of such chemical agents include Dibucaine, benzocaine, cocaine, tetracaine, dyclonine, pramoxine, lidocaine, priocaine, as described in Windle ("Anesthesia, topical"; WebMD.com, printed Sep. 28, 2007, Original publication date Mar. 14, 2007), which is incorporated herein by reference in its entirety.

Ultrasonic stimuli have been shown to produce reversible conduction block in patients with in painful polyneuropathy (see Hong, "Reversible nerve conduction block in patients with polyneuropathy after ultrasound thermotherapy at therapeutic dosage."; Arch. Phys. Med. Rehabil.; February 1991; pp. 132-137; Vol. 72(2). (Abstract only), which is incorporated herein by reference in its entirety). Ultrasound may also be used in nerve stimulation, either alone or in combination with magnetic or electrical stimuli. See, for example, Norton ("Can ultrasound be used to stimulate nerve tissue?"; Bio-Medical Engineering OnLine; Published 4 Mar. 2003; http://www.biomedical-engineering-online.com/content/2/1/6) and Tsui et al., ("In Vitro Effects of Ultrasound with Different Energies on the Conduction Properties of Neural Tissue"; ScienceDirect-Ultrasonics; 2005; pp. 560-565; Vol. 43; Elsevier B. V.; located at: www.elsevier.com/locate/ultras), both of which are incorporated fully herein by reference.

Optionally, neural modulation system 700 may include override signal input structure 720, as indicated by the dashed box in FIG. 10. Override signal input structure may be configured to receive a signal indicative of a condition of the body of the subject, and the signal processing portion 706 may be configured to override generation of the blocking stimulus control signal responsive to a signal indicative of an override condition of the body of the subject on override signal input structure 720. Alternatively, override signal input structure 720 may be configured to receive a signal indicative of a condition external to the body of the subject, and signal processing portion 706 may be configured to override generation of the blocking stimulus control signal responsive to a signal indicative of an override condition external to the body of the subject on the override signal input. Alternatively, or in addition, override signal input structure 720 may be configured to receive a signal from a user input device, and the signal processing portion may be configured to override generation of the blocking stimulus control signal responsive to a signal indicative of a user override request on the override signal input. As noted previously, the override signal to be received on override signal input structure 720 indicate that it is no longer desirable to apply the blocking stimulus, for reasons of safety, comfort, or convenience, for example. The override signal may be indicative of a condition of the body of the subject, or indicative of a condition external to the body of the subject (e.g., in the environment of the subject). If the override signal is detected from a user input device, it may be the same user input device used in normal operation of the system, and the override signal input structure may be the same as the signal input structure that normally receives input from a user input device.

Sensor 704 as depicted generally in FIG. 10 may include any of a variety of different types of sensors, including, but not limited to, pressure sensors, force sensors, chemical sensors (including but not limited to sensors capable of sensing pH, gas, ions, proteins, or biomolecules), temperature sensors, electrical sensors (for sensing current, potential, charge, resistance, resistivity, capacitance, or other electrical parameters), magnetic sensors, optical sensors, motion sensors, etc. A single sensor or multiple sensors, of the same or multiple types, may be used.

In some embodiments, a physiological sensor may be used. In such embodiments, a neural modulation system may include a signal input structure configured to receive a signal indicative of an activity state of at least a portion of a body of a subject innervated by a peripheral neural structure; a physiological sensor operatively connected to the signal input structure and configured to generate the signal indicative of an activity state of the at least a portion of the body of the subject innervated by the peripheral neural structure, the physiological sensor being responsive to a physiological parameter of the at least a portion of the body of the subject; and a signal processing portion configured to distinguish a first activity state of the at least a portion of the body of the subject innervated by the peripheral neural structure from a second activity state of the at least a portion of the body of the subject innervated by the peripheral neural structure at least partially based on the signal received at the signal input structure and generate a blocking stimulus control signal for driving production of a blocking stimulus configured to reversibly block conduction in the peripheral neural structure of the subject during at least a portion of the first activity state.

The physiological sensor may be configured to generate a signal indicative of activity of the heart of the subject, activity of brain of the subject, activity of a peripheral neural system of the subject, activity of a muscle of the subject, respiration of the subject, body temperature of the subject, or other physiological signals that may be indicative of an activity state of all or a portion of the body of the subject. The detection of these and other physiological signals is known to those of skill in the art. Examples of some possible physiological signals that may indicate activity of all or a portion of a body of a subject include electroencephalographic signals (EEG), electromyographic signals (EMG), electrocardiographic signals (ECG), heart rate, blood pressure, blood oxygenation, respiration rate, respiratory volume, or body temperature. Specific activity states such as sleep may be indicated by particular chemical indicators, e.g. concentration of melatonin in body fluid or other measures (see, for example, U.S. Patent Publication 2005/0215947, which is incorporated herein by reference in its entirety).

In some embodiments, a physical activity sensor may be used. In such embodiments, a neural modulation system may include a signal input structure configured to receive a signal indicative of an activity state of at least a portion of a body of a subject innervated by a peripheral neural structure; a physical activity sensor operatively connected to the signal input structure and configured to generate the signal indicative of an activity state of the at least a portion of the body of the subject innervated by the peripheral neural structure responsive to physical activity of the at least a portion of the body of the subject; and a signal processing portion configured to distinguish a first activity state of the at least a portion of the body of the subject innervated by the peripheral neural structure from a second activity state of the at least a portion of the body of the subject innervated by the peripheral neural structure at least partially based on the signal received by the signal input structure and generate a blocking stimulus control signal for driving production of a blocking stimulus configured to reversibly block conduction in the peripheral neural structure of the subject during at least a portion of the first activity state.

The physical activity sensor may be configured to generate a signal indicative of motion or acceleration of the at least a portion of the body of the subject innervated by the peripheral neural structure. In some embodiments, the physical activity sensor may be configured to generate a signal indicative of a body position or posture of the subject. Physical activity sensors may sense various aspects of posture or movement (amplitude, frequency, direction, etc.) and may include various types of sensors, singly or in combination, including but not limited to switches, force or pressure sensors, accelerometers, gyros, mercury switch, piezoelectric devices, and other activity sensing devices as known to those of skill in the art.

Sensor 704 may be located external to the body of the subject or internal to the body of the subject.

Components of neural modulation systems as described herein may be packaged in various manners. In some cases, all components of a system may be packaged together. Such a package may be designed for use outside the body, or designed for use inside the body in an implantable system. However, in many cases it may be desirable to package certain components of the system separately.

Figure 11:
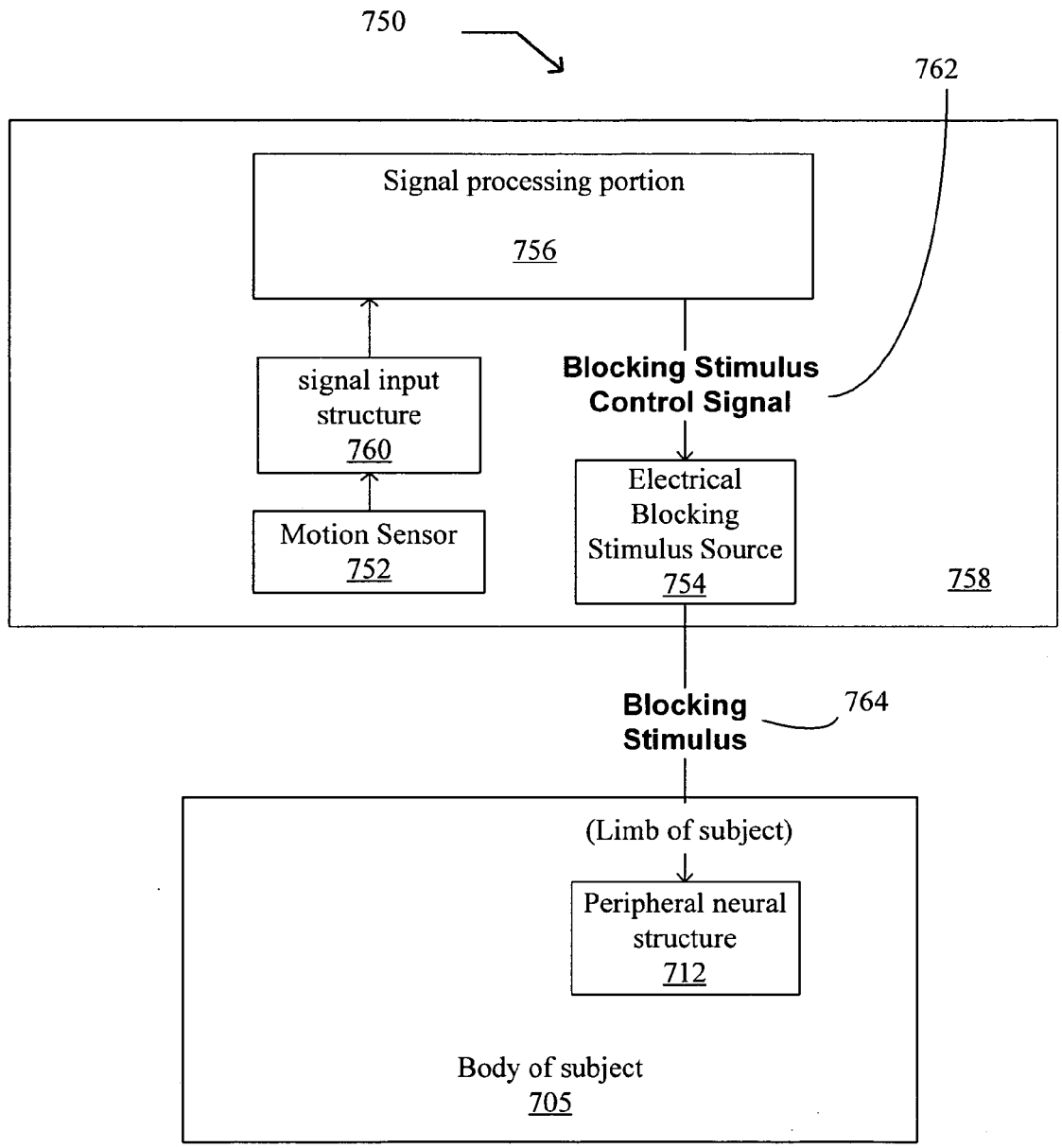
FIG. 11 is a block diagram of another example of a neural modulation system.

FIG. 11 depicts an example of a neural modulation system 750 in which a sensor (motion sensor 752) and blocking stimulus source (electrical blocking stimulus source 754) are packaged with signal processing portion 756 in package 758. Motion sensor 752 provides an input to signal processing portion 756 via signal input structure 760. Signal processing portion 756 generates blocking stimulus control signal 762 which drives production of blocking stimulus 764 by electrical blocking stimulus source 754. Package 758 may be adapted to be positioned external to the body of subject 705, and electrical blocking stimulus 764 may pass through body tissues to reach peripheral neural structure 712. Electrical blocking stimulus source may include electrodes configured to deliver an electrical field to the body of the subject sufficient to produce blocking of a nerve. Package 758 may be configured to secured to a limb (e.g., with a strap or elastic band) over a peripheral neural structure 712, so that the electrical blocking stimulus may be delivered to the peripheral neural structure. Generation of blocking stimulus control signal 762 by signal processing portion 756 may be responsive to a signal from motion sensor 752, such that a blocking stimulus may be delivered to the peripheral neural structure when the limb is not in motion, for example. The peripheral neural structure may be, for example, a sensory nerve, blockage of neural activity therein may, for example, reduce or limit pain or inflammation, e.g. of arthritis, peripheral vascular disease, etc. In related embodiments, sensor 752 may be any of various types of sensors, as described elsewhere herein.

Figure 12:
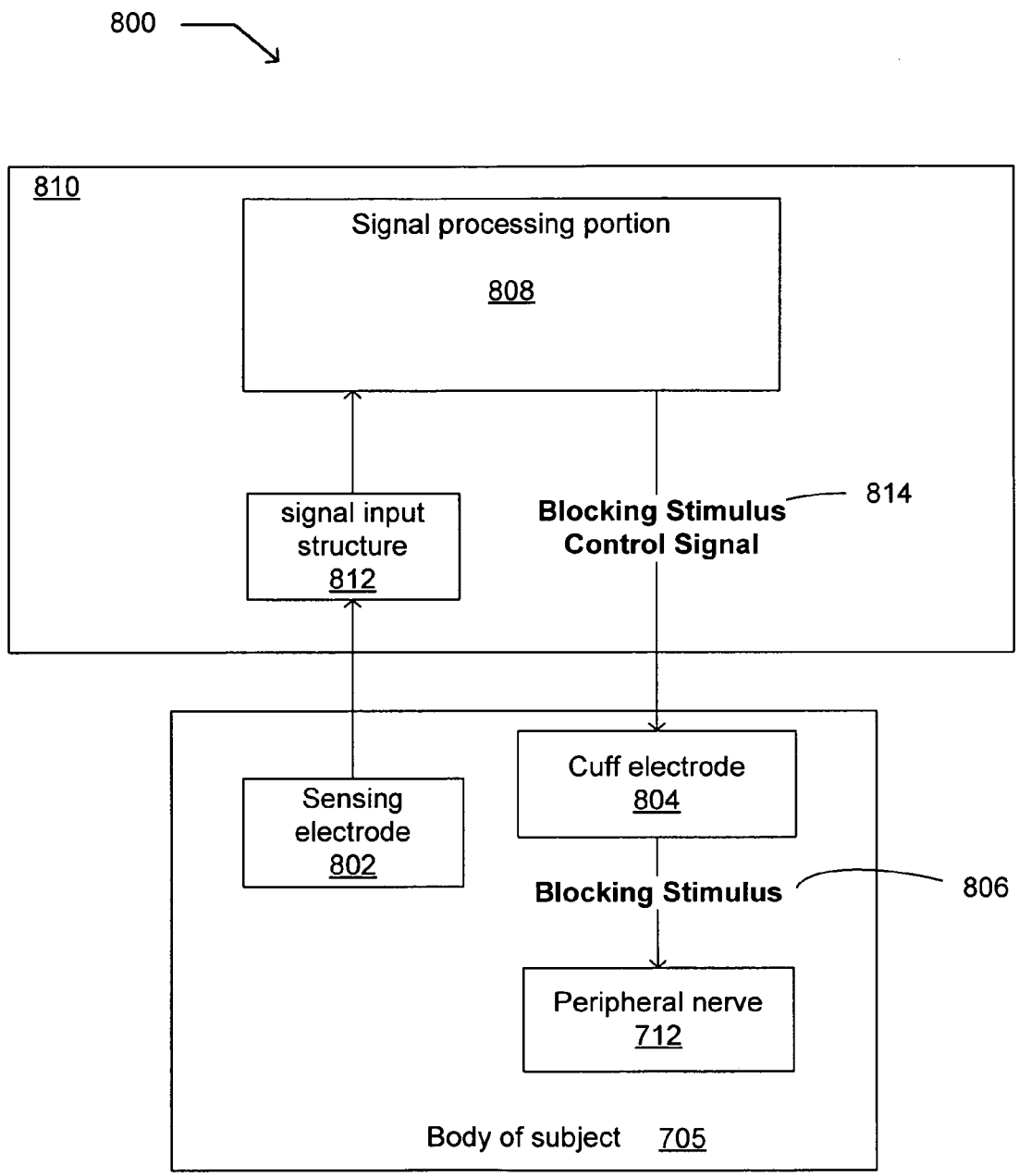
FIG. 12 is a block diagram of an example of a neural modulation system.

FIG. 12 depicts an example of a neural modulation system 800 in which an implanted sensor and implanted blocking stimulus source are used. In this example, the implanted sensor may be sensing electrode 802, and the blocking stimulus source may be cuff electrode 804. Cuff electrode 804 may include electrode contacts within an insulating cuff, for example as described in U.S. Patent Publication 2006/0190053 and U.S. Pat. No. 5,755,750, which are incorporated herein by reference in their entirety. Sensing electrode 802 and cuff electrode 804 may be implanted within the body of subject 705, such that sensing electrode 802 may sense neural or muscular activity representative of activity of at least a portion of the body of the subject, and cuff electrode 804 may deliver blocking stimulus 806 to a peripheral neural structure, peripheral nerve 712. As used herein, "implanted" means located or positioned, either temporarily or permanently, within the body of the subject. Signal processing portion 808 may be packaged separately, e.g. in package 810. Sensing electrode 802 may provide an input to signal processing portion 808 via signal input structure 812. Signal processing portion 808 may generate blocking stimulus control signal 814 for driving production of blocking stimulus 806 by cuff electrode 804. Package 810 may be implanted within the body of subject 705, or located external to body of subject 705. In either case, signals may be transmitted between signal processing portion 808 and sensing electrode 802 and cuff electrode 804 via a wire or cable, optical ink, acoustic link, radiofrequency or other electromagnetic link, or other wireless communication link, as is known to those of skill in the art. As discussed in connection with FIG. 13, blockage of neural activity may reduce or limit pain or inflammation. In one application, for example, sensing electrode 802 and cuff electrode 804 may be implanted on a sensory nerve innervating a limb, appendage, or joint (for example, a knee) that has suffered injury and/or damage, with the goal of limiting the progression of arthritis that would otherwise be associated with the injury or damage.

Figure 13:
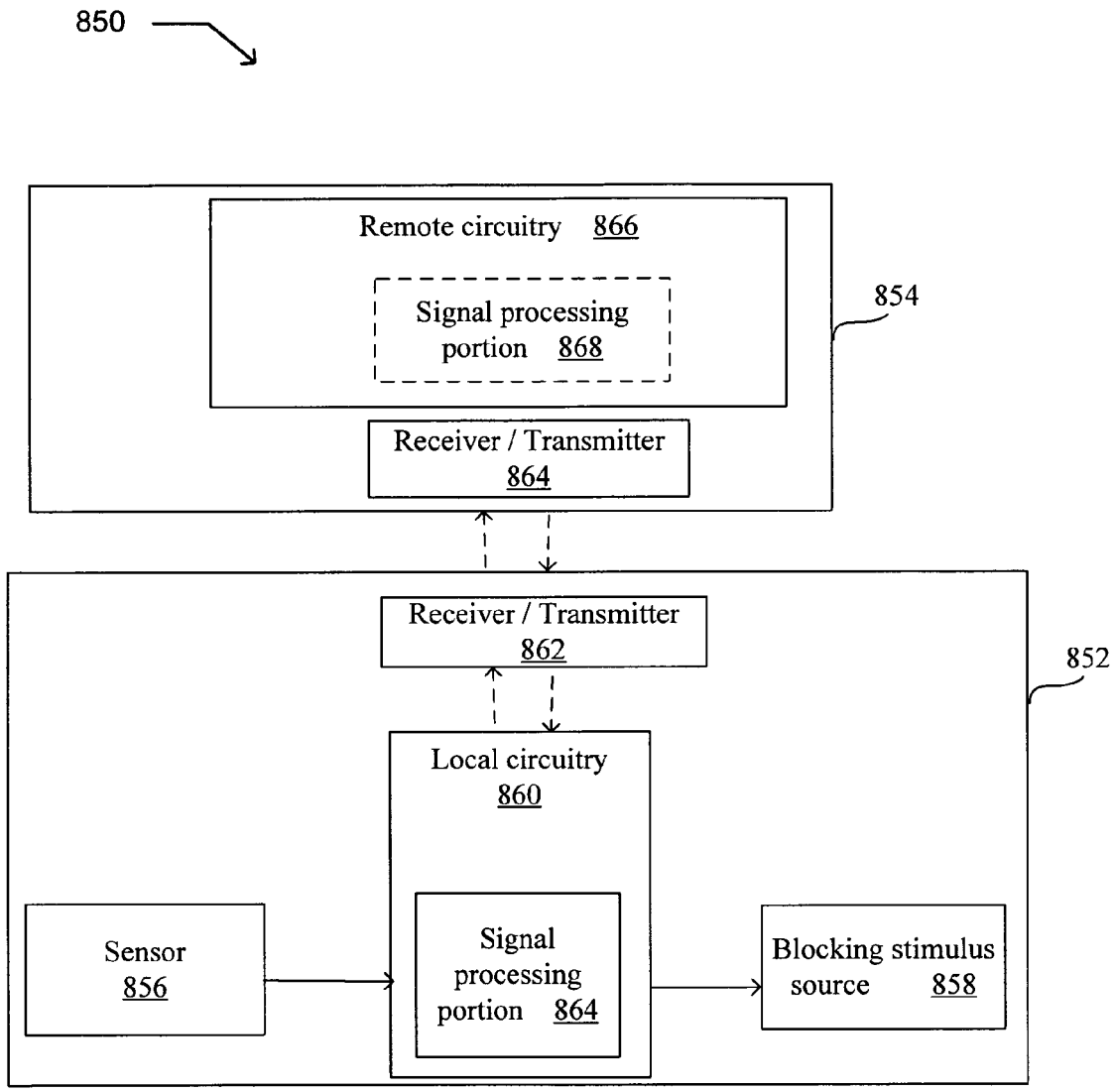
FIG. 13 is a block diagram of a further example of a neural modulation system.

FIG. 13 depicts in further detail an example of a system 850 in which components are packaged so that some can be used locally (e.g. implanted in the body or positioned on or near the body surface) while others are used remotely, which in this context may be in a separate package located relatively close by (i.e. in, on or near the body), or at a distant location such as across a room, in a separate room, or in a separate building). System 850 includes local portion 852 and remote portion 854. Local portion 852 may be implanted in the body of a subject or positioned on or near the body surface, while remote portion 854 may be located remotely from local portion 852. Local portion 852 may include sensor 856 and blocking stimulus source 858. Local portion 852 may also include local circuitry portion 860 and receiver/transmitter 862. A corresponding receiver/transmitter 864 in remote portion 854 permits the transmission of data and instructions between local portion 852 and remote portion 854. In some embodiments, power may also be transmitted between remote portion 854 and local portion 852. Alternatively, or in addition, one or both of local portion 852 and remote portion 854 may include a power source (e.g., a battery or other power source as known to those of skill in the art). Remote portion 854 may include remote circuitry 866, which may include signal processing portion 868. The signal processing portion of the system may include only signal processing portion 868 in remote portion 854, or it may include both signal processing portion 868 in remote portion 854 and signal processing circuitry 864 in local portion 852. Alternatively, in some embodiments, the signal processing portion may include signal processing circuitry 864 in local portion 852 and remote circuitry 866 may be devoted to other functions.

Components packaged separately may be operatively connected to other components by cables, a wireless link (which may be optical, electromagnetic, acoustic, etc.). Separately packaged components may be suited for use outside or inside the body. In some embodiments, some components may be positioned inside the body while other are positioned outside the body during use. In some embodiments, the signal processing portion may be configured to perform encryption of signals transmitted to separately packaged and/or remote components or device portion, e.g. a blocking stimulus control signal. Similarly, the signal processing portion may be configured to perform decryption of signals received from, e.g., a user input device, via a signal input structure or override signal input structure. Encryption/decryption may be performed by standard methods as known to those of skill in the art, for example, as used in computers, networks, mobile telephones, wireless microphones, wireless intercom systems, Bluetooth devices, and so forth. Encryption/decryption may be used in order to provide secure transmission of information, for example for protecting privacy of personal information and/or for avoiding interference between multiple devices used in the same area.

Figure 14:
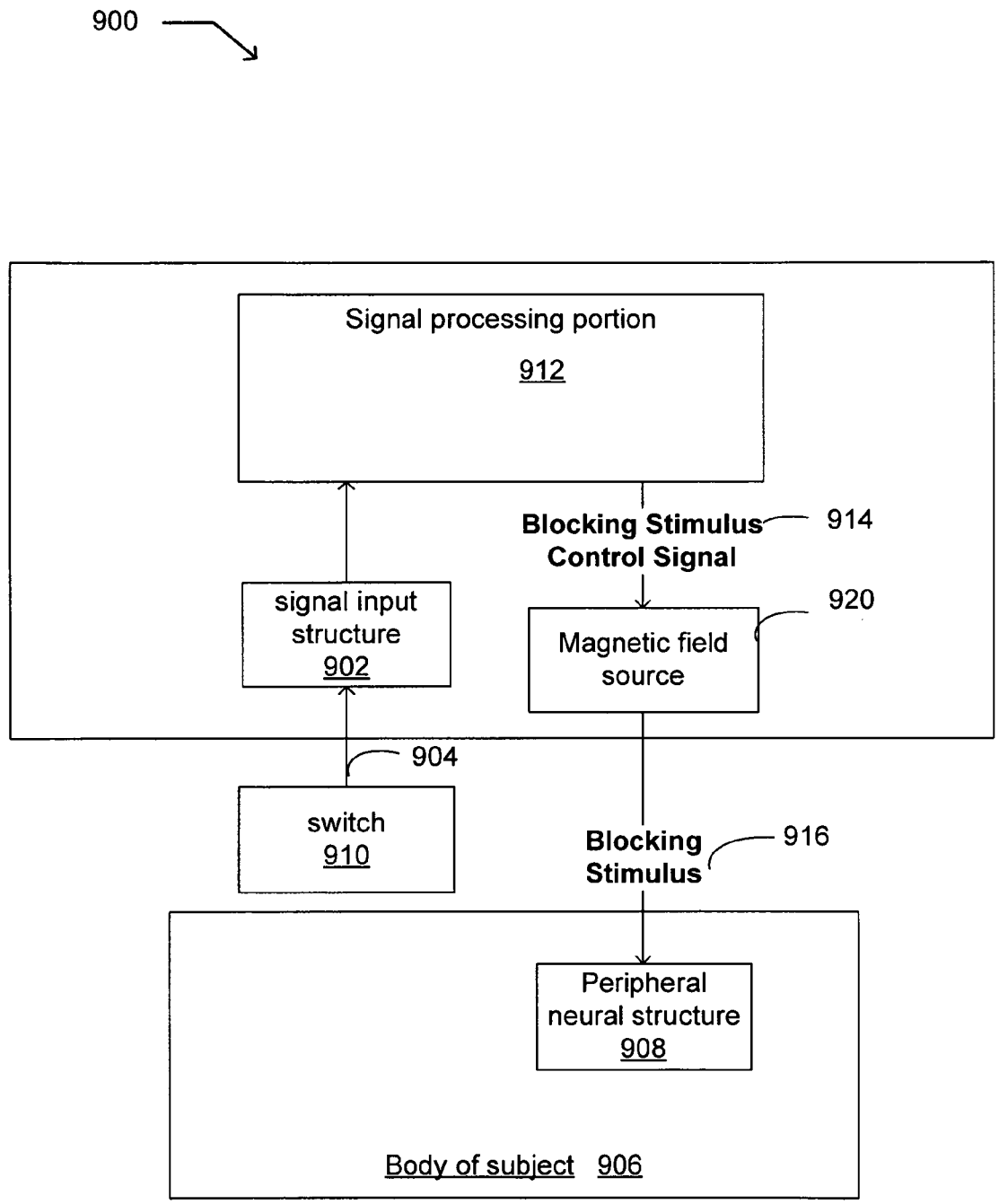
FIG. 14 is a block diagram of a further example of a neural modulation system.

In some embodiments, a user input device may be used in place of (or in addition to) a sensor in order to provide indication of an activity or use state of all or a portion of the body of the subject. Such a system is depicted in schematic form in FIG. 14. As shown in FIG. 14, neural modulation system 900 may include a signal input structure 902 configured to receive a signal 904 indicative of an activity state of at least a portion of a body of a subject 906 innervated by a peripheral neural structure 908; a user input device (switch 910) operatively connected to the signal input structure 902 and configured to generate a signal 904 responsive to a user input indicative of an activity state of at least a portion of a subject 906 innervated by the peripheral neural structure 908. For example, switch 910 may be set to the "on" setting when the subject is entering a first activity state, and set to the "off" setting when the subject is entering a second activity state. Neural modulation system 900 also includes signal processing portion 912 configured to distinguish a first activity state of the at least a portion of the body of the subject 906 innervated by the peripheral neural structure 908 from a second activity state of the at least a portion of the body of the subject 906 innervated by the peripheral neural structure 908 from the signal 904 received at the signal input structure 902 (e.g., by detecting the "on" or "off" setting of switch 910); and generate a blocking stimulus control signal 914 for driving production of a blocking stimulus 916 configured to reversibly block conduction in the peripheral neural structure 908 of the body of subject 906 during at least a portion of the first activity state. Blocking stimulus 916 is produced by a blocking stimulus source (in this example, magnetic field source 920) responsive to blocking stimulus control signal 914.

A user of the system depicted in FIG. 14 (the subject or another party, such as a medical care-giver or assistant) may use user input device (e.g., switch 910) to indicate that the subject is currently resting or inactive (e.g., sitting in a chair or lying in bed) or about to begin a period of rest or inactivity, (e.g., by changing the setting of switch, as described above). Similarly, a user of the system may also use the user input device to indicate the end of a period of rest or inactivity. The user input device may include various types of user input devices, as are known to those of skill in the art. For example, the user input device may include one or more of the following: a voice-activated or other sound-activated input device, e.g. a microphone, a user-activated switch or knob, a keyboard, a mouse or other pointing device, a touch-screen or other user activated input devices.

The foregoing are examples, and various other devices that allow the subject or other user to signal a change (or expected change) in activity state may be used in practice.

As discussed in connection with systems in which sensors are used to provide indication of an activity or use state of all or a portion of the body of the subject, the various components of the system may be packaged together or separately, located locally or remotely, inside or outside the body of the subject, as depicted in FIGS. 10-13. For example, FIG. 14 shows an example of a system in which switch 910 is packaged separately from the signal processing portion 912 and is located outside of the body of subject 906, while magnetic field source 920 is packaged with signal processing portion 912. Signal processing portion 912 and magnetic field source 920 may be in a package configured to be placed against the subject's body as the subject rests, while switch 910 may be connected to signal processing portion 912 with a cable, for example (or, alternatively, a wireless connections such as an optical or RF connection). The subject may toggle switch 910 to indicate the beginning or end of a rest period during which the blocking stimulus is to be delivered. Magnetic field source 920 may be configured to generate a magnetic field sufficient to block conduction in peripheral neural structure 908 (see, e.g. Olree and Horch ("Differential activation and block of peripheral nerve fibers by magnetic fields"; Muscle & Nerve; 2006; pp. 189-196; Vol. 34, Wiley Periodicals), which is incorporated herein by reference in its entirety. Peripheral neural structure 908 may be blocked with the goal of producing a particular beneficial effect, such as to limit the progression of an inflammatory process (e.g. in diabetes, arthritis, vascular disease).

Figure 15:
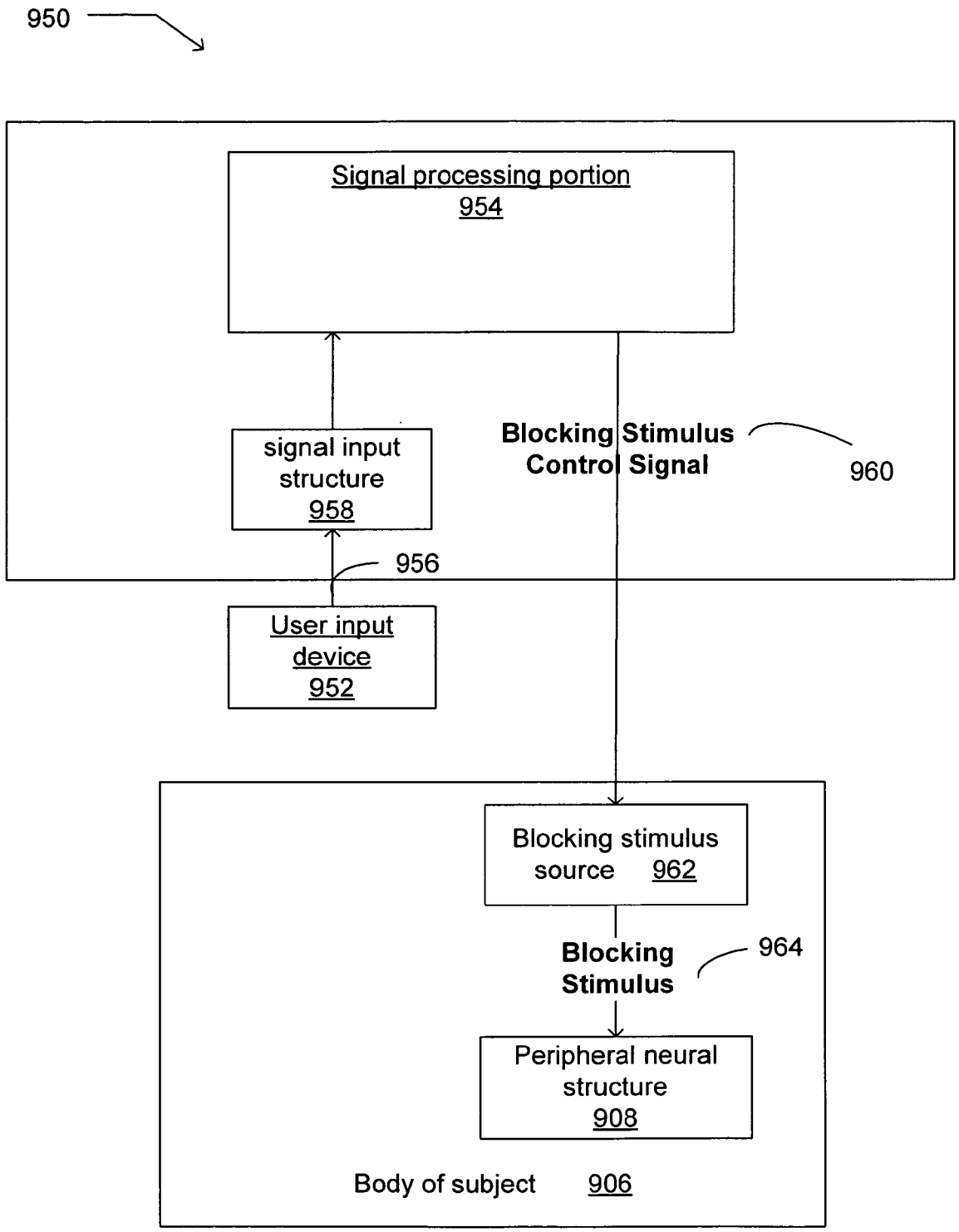
FIG. 15 is a block diagram of another example of a neural modulation system.

FIG. 15 depicts a further example of a system 950 in which user input device 952 is packaged separately from signal processing portion 954, providing signal 956 to signal input structure 958. Signal processing portion 954 generates blocking stimulus control signal 960, which is provided (e.g., transmitted) to blocking stimulus source 962, which is implanted within the body of subject 906. As discussed previously, blocking stimulus source 962 generates blocking stimulus 964 for blocking conduction in peripheral neural structure 908 in body of subject 906. Other arrangements of system components are possible, and systems as described generally herein are not limited to the specific arrangements of components depicted in the figures.

Figure 16:
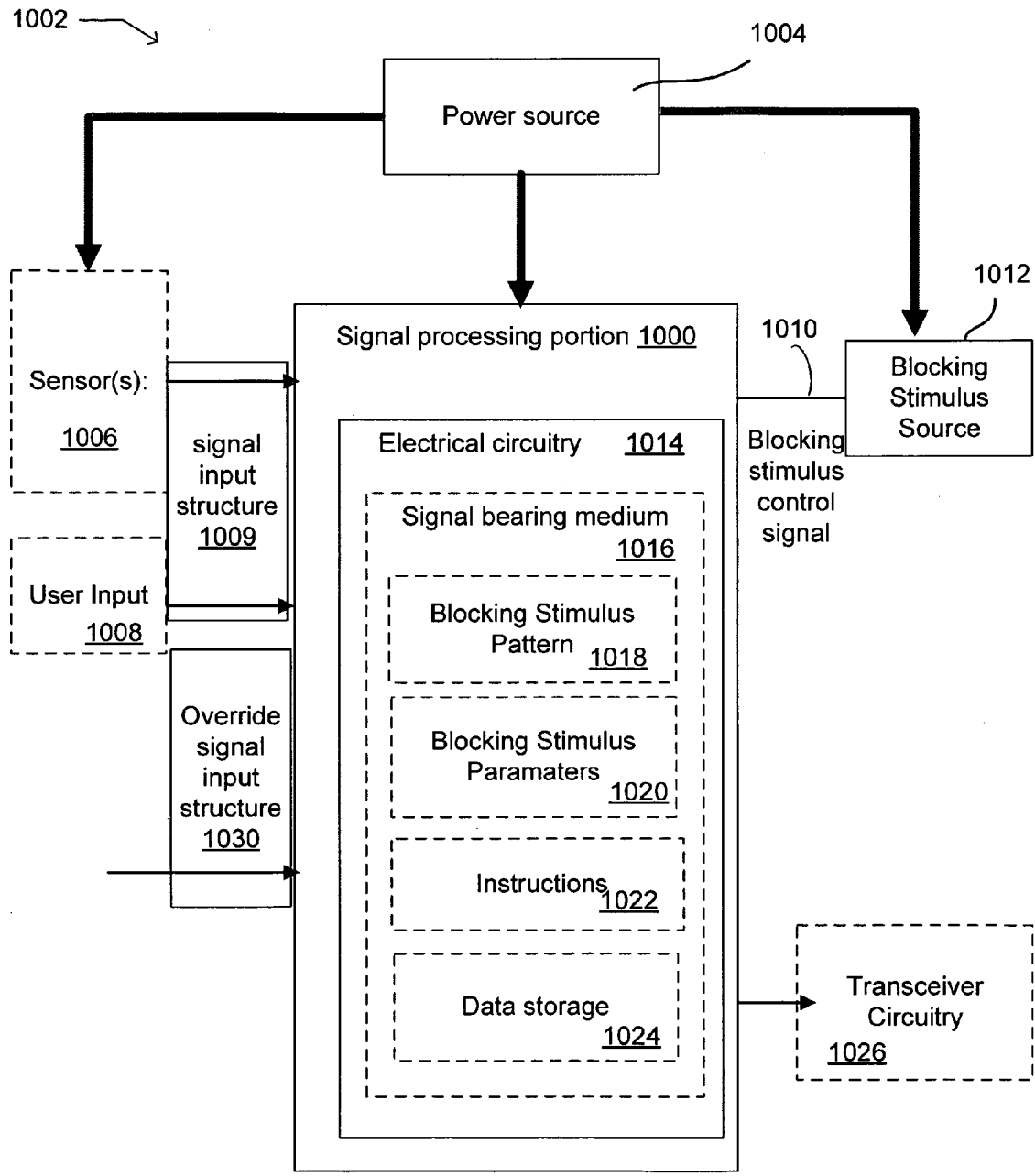
FIG. 16 is a block diagram of a signal processing portion of a neural modulation system.

A schematic diagram showing components and operation of a signal processing portion 1000 of a neural modulation system 1002 is shown in FIG. 16. The functional relationship of signal processing portion 1000 to other components of neural modulation system 1002 is also shown. As noted previously, signal processing portion 1000 and other system components may be powered by a single power source, as shown in FIG. 16 as power source 1004; or multiple power sources. Signal processing portion 1000 may receive as input signals from one or more sensors 1006 and/or one or more user input devices 1008 via signal input structure 1009, and optionally, a signal from override signal input structure 1030. Signal processing portion 1000 may generate as output blocking stimulus control signal 1010 for driving blocking stimulus source 1012 to produce a blocking stimulus.

Signal processing portion 1000 may include electrical circuitry 1014 for performing signal processing functions including but not limited to amplification, filtering, signal averaging, thresholding, variable-changing, waveform analysis, variable (e.g., time- or spatial-frequency) domain transformation, convolution, cross-spectral analysis, feature or pattern recognition or extraction, processing performed relative to data-stored-in-memory, etc., or a combination or concatenation of any or all of these, as is known to those of skill in the art of signal processing, whether such operations may be done in software, firmware or hardware or combinations of these. Electrical circuitry 1014 may also be configured to generate blocking stimulus control signal 1010 for driving blocking stimulus source 1012.

As noted previously, the blocking stimulus may be applied with a cyclical application pattern according to a detected signal indicative of at least one activity state in the subject and/or according to a pre-set schedule. Signal processing portion 1000 may include at least one signal bearing medium 1016 that may contain blocking stimulus pattern 1018, which specifies the configuration (e.g. waveform and timing of application) of a blocking stimulus. Signal bearing medium 1016 may also including blocking stimulus parameters 1020 related to generating blocking stimulus control signal 1010 according to a detected signal from sensor 1006 or user input 1008. Stimulus parameters 1020 may include constants and/or variables to be used in calculations of blocking stimulus control signal 1010 as a function of the detected signal. Signal bearing medium 1016 may include instructions 1022, which may relate to one or more of receiving or acquiring signals on signal input structure 1009, processing the signals, generating blocking stimulus control signal 1010, storing data (e.g. signals or parameters representing some or all of sensor or user input, blocking stimulus control signal, etc.) in data storage location 1024, and instructions related to transmitting and/or receiving data or instructions via transmitter/receiver circuitry 1026.

In a general sense, those of skill in the art will recognize that the various aspects described herein that can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program that at least partially carries out processes and/or devices described herein, or a microprocessor configured by a computer program that at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Operation of neural modulation devices as described herein may be performed under the control of hardware (e.g. analog or digital electronic circuitry). Circuitry for switching, signal generation, sensing, timing control etc. is well known and may be constructed by those of skill in the art of electronics. In some embodiments, control of neural modulation devices as described herein may be performed under microprocessor control. Instructions to be executed by a microprocessor may be stored in hardware, firmware, or software (e.g. as an ASIC, instructions burned into an EEPROM, instructions stored in various types of memory devices/structures) on various types of signal-bearing media. Instructions for controlling neural modulation devices as described herein may be used, for example to implement methods as outlined, e.g. in FIGS. 4, 8 and 9. Instructions carried on a signal bearing medium may form a permanent or temporary component of a system including additional device components. Signal bearing media used, e.g. as depicted in FIG. 16, may include both instructions for controlling neural modulation device, and also stored data or parameters. Data, parameters, and instructions may be stored on more than one types of media during the practice of the invention (e.g., partially in device memory, partially on a removable medium, etc.).

Figure 17:
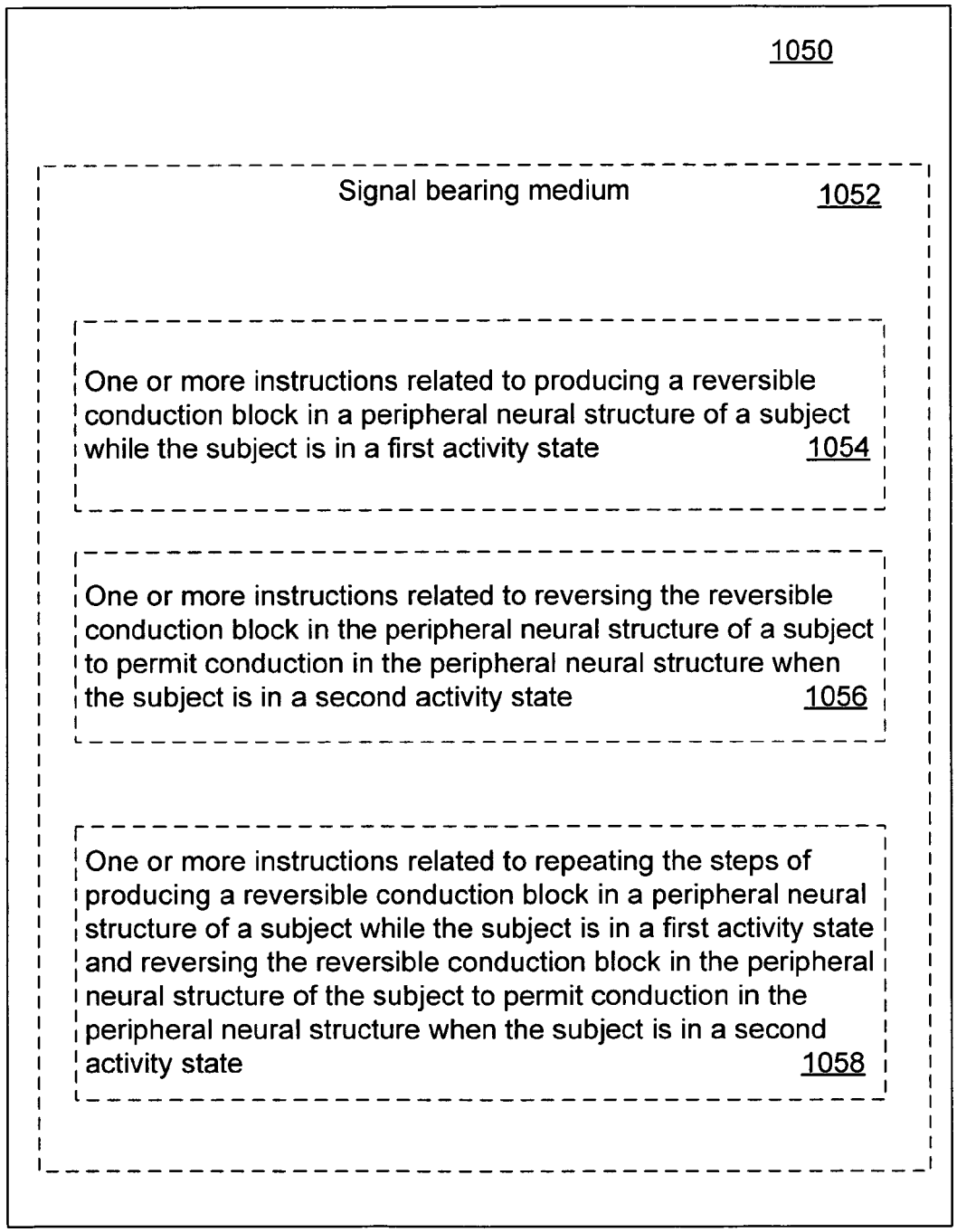
FIG. 17 is a block diagram of a system including a signal-bearing medium bearing instructions related to operation of a neural modulation system.

As illustrated in FIG. 17, in one embodiment, a system 1050 may include a signal-bearing medium 1052 bearing: one or more instructions related to producing a reversible conduction block in a peripheral neural structure of a subject while the subject is in a first activity state, as indicated at 1054; one or more instructions related to reversing the reversible conduction block in the peripheral neural structure of the subject to permit conduction in the peripheral neural structure when the subject is in a second activity state, as indicated at 1056; and one or more instructions related to repeating the steps of producing a reversible conduction block in a peripheral neural structure of a subject while the subject is in a first activity state and reversing the reversible conduction block in the peripheral neural structure of the subject to permit conduction in the peripheral neural structure when the subject is in a second activity state, as indicated at 1058. System 1050, represented in FIG. 17 as a box, may include all or part of a neural modulation system. In some embodiments, a portion of a neural modulation system may include a fixed or removable data storage device that includes signal-bearing medium 1052.

The signal bearing medium may bear one or more instructions related to repeating the steps of producing a reversible conduction block in a peripheral neural structure of a subject while the subject is in a first activity state and reversing the reversible conduction block in the peripheral neural structure of the subject to permit conduction in the peripheral neural structure when the subject is in a second activity state cyclically, wherein each cycle includes a blocking period during which a blocking stimulus sufficient to produce reversible conduction block in a peripheral neural structure of a subject is produced while the subject is in a first activity state and a release period during which no blocking stimulus is delivered.

The signal bearing medium may bear one or more instructions related to repeating the steps of producing a reversible conduction block in a peripheral neural structure of a subject while the subject is in a first activity state and reversing the reversible conduction block in the peripheral neural structure of the subject to permit conduction in the peripheral neural structure when the subject is in a second activity state cyclically at a rate of one cycle per day.

In some embodiments, the signal bearing medium may bear one or more instructions related to producing the reversible conduction block and reversing the reversible conduction block in alternation according to a pre-set schedule, e.g. to produce a blocking stimulus as depicted in trace 400 in FIG. 6. Alternatively, the signal-bearing medium may bear one or more instructions related to producing the reversible conduction block and reversing the reversible conduction block in alternation according to a detected signal indicative of at least one activity state in the subject, wherein the at least one activity state of the subject has a substantially cyclical expected pattern of occurrence, e.g., to produce a blocking stimulus as depicted in trace 360 of FIG. 6.

The signal-bearing medium may be carried by a neural modulation device. For example, the signal-bearing medium may include a non-volatile memory in the neural modulation device. The non-volatile memory may be, for example, selected from a ROM, PROM, EPROM, EEPROM, or Flash memory.

In some embodiments, the signal-bearing medium may be carried in part by a neural modulation device and in part by a remote device, for example, as depicted in FIG. 13.

In connection with embodiments in which signals sent and received by the device are encrypted or decrypted, as described elsewhere herein, the signal bearing medium may bear one or more instructions related to at least one of encrypting or decrypting an input indicative of an activity state of the subject, or one or more instructions related to at least one of encrypting or decrypting an input indicative of a user instruction.

The signal-bearing medium may include one or more of a computer-readable medium, a recordable medium, or a communications medium. A communications medium may be, for example, at least one optical fiber, at least one wire, or a wireless communications medium.

Figure 18:
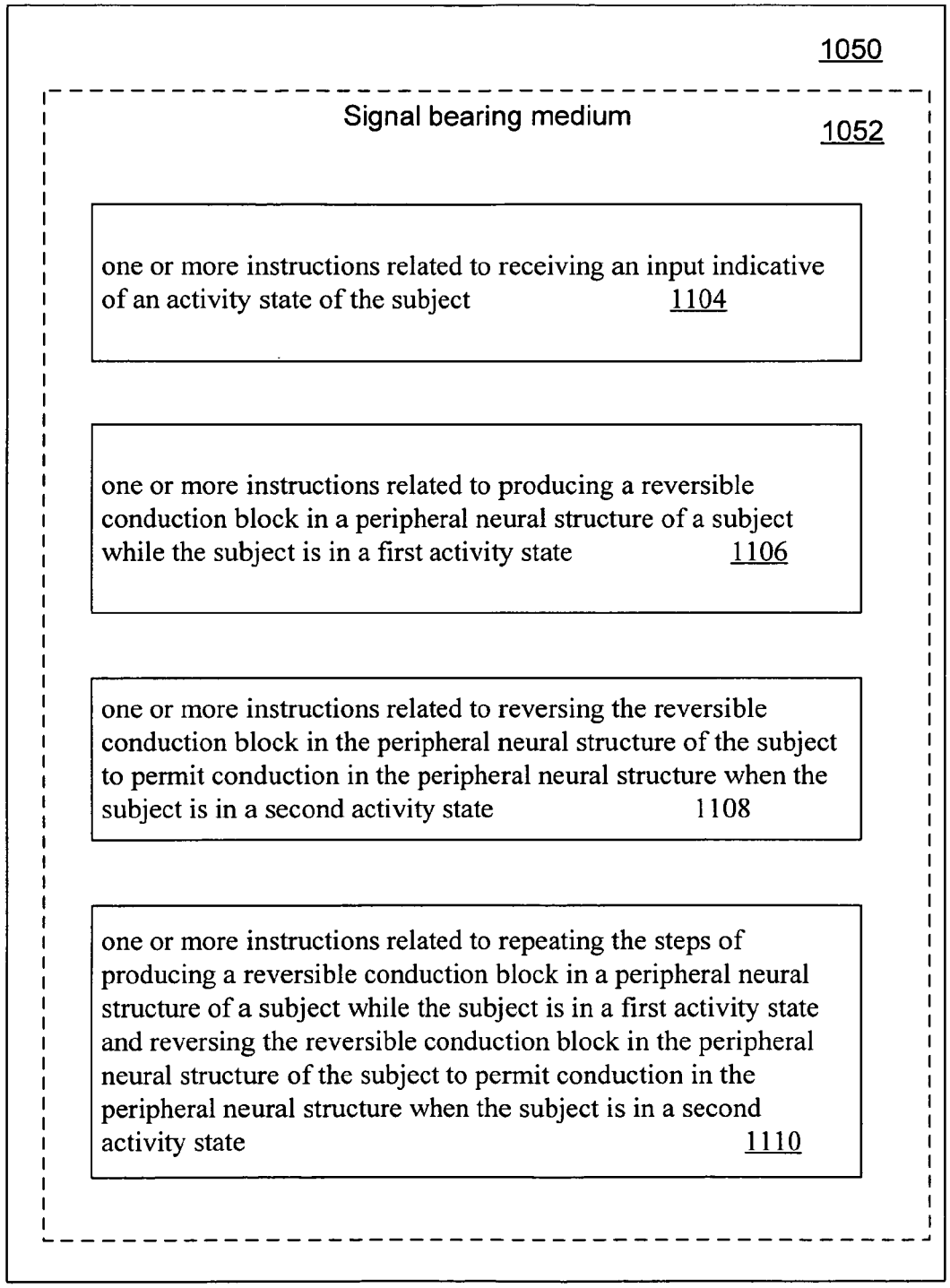
FIG. 18 is a block diagram of a system including a signal-bearing medium bearing instructions related to operation of a neural modulation system.

In a further embodiment, as illustrated in FIG. 18, a system 1050 may include a signal-bearing medium 1052 bearing one or more instructions related to receiving an input indicative of an activity state of the subject (as indicated at 1104); one or more instructions related to producing a reversible conduction block in a peripheral neural structure of a subject while the subject is in a first activity state (as indicated at 1106); one or more instructions related to reversing the reversible conduction block in the peripheral neural structure of the subject to permit conduction in the peripheral neural structure when the subject is in a second activity state (as indicated at 1108); and one or more instructions related to repeating the steps of producing a reversible conduction block in a peripheral neural structure of a subject while the subject is in a first activity state and reversing the reversible conduction block in the peripheral neural structure of the subject to permit conduction in the peripheral neural structure when the subject is in a second activity state (as indicated at 1110).

In some embodiments, the one or more instructions related to receiving an input indicative of an activity state of the subject may include one or more instructions related to receiving an input indicative of overall activity of the subject. The signal bearing medium may bear one or more instructions related to distinguishing an input indicative of a first activity state from an input indicative of a second activity state, wherein the first activity state is characterized by relatively lower overall activity of the subject than the second activity state.

In some embodiments, the one or more instructions related to receiving an input indicative of an activity state of the subject may include one or more instructions related to receiving an input indicative of use of a body portion innervated by the peripheral neural structure by the subject, rather than overall activity of the subject. The signal bearing medium may bear one or more instructions related to distinguishing an input indicative of a first activity state from an input indicative of a second activity state, wherein the first activity state is characterized by relatively lower use of the body portion innervated by the peripheral neural structure by the subject than the second activity state.

The one or more instructions related to receiving an input indicative of an activity state of the subject may include instructions related to receiving an input indicative of physiological activity of the subject, including, but not limited to an input indicative of a heart rate, a brain activity, a muscle activity, respiration, a peripheral nervous system, or a body temperature of the subject.

Alternatively, or in addition, the one or more instructions related to receiving an input indicative of an activity state of the subject may include one or more instructions related to receiving an input indicative of physical activity of the subject, for example, an input indicative of motion, body position, or posture of the subject.

Instructions related to receiving an input indicative of an activity state of the subject may include instructions related to receiving an input from of pressure sensor, force sensor, chemical sensor, temperature sensor, electrical sensor, magnetic sensor, optical sensor, motion sensor, a switch, or various other types of sensors as known to those of skill in the art and as described elsewhere herein.

Figure 19:
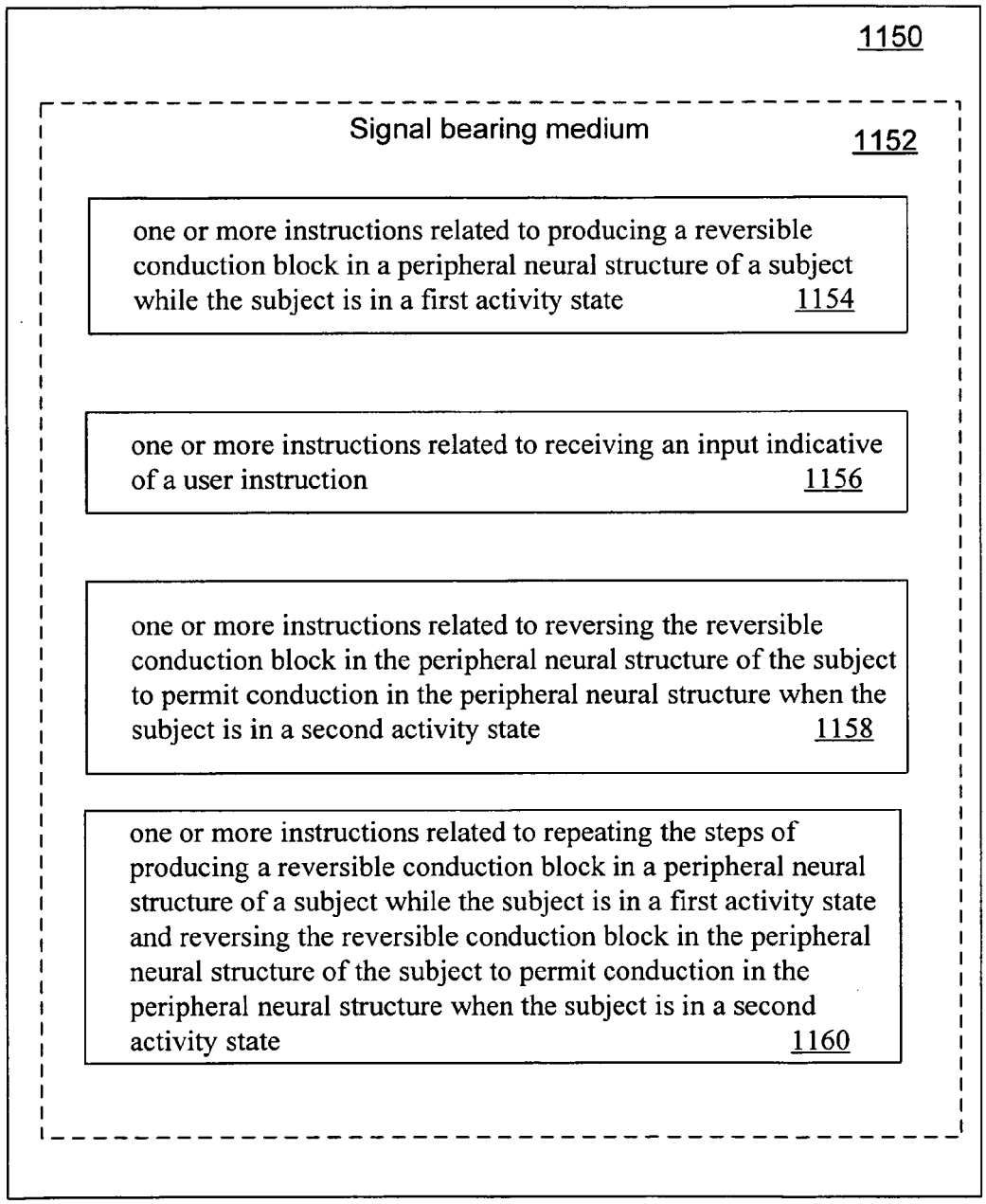
FIG. 19 is a block diagram of a system including a signal-bearing medium bearing instructions related to operation of a neural modulation system.

In another embodiment, as shown in FIG. 19, the system 1150 may include a signal-bearing medium 1152 bearing one or more instructions related to producing a reversible conduction block in a peripheral neural structure of a subject while the subject is in a first activity state (as indicated at 1154); one or more instructions related to receiving an input indicative of a user instruction (as indicated at 1156); one or more instructions related to reversing the reversible conduction block in the peripheral neural structure of the subject to permit conduction in the peripheral neural structure when the subject is in a second activity state (as indicated at 1158); and one or more instructions related to repeating the steps of producing a reversible conduction block in a peripheral neural structure of a subject while the subject is in a first activity state and reversing the reversible conduction block in the peripheral neural structure of the subject to permit conduction in the peripheral neural structure when the subject is in a second activity state (as indicated at 1160).

The one or more instructions related to receiving an input indicative of a user instruction include one or more instructions related to receiving an input from a user input device, such as a voice-activated or other sound-activated input device, e.g. a microphone, a user-activated switch or knob, a keyboard, a mouse or other pointing device, a touch-screen or other user activated input devices.

Figure 20:
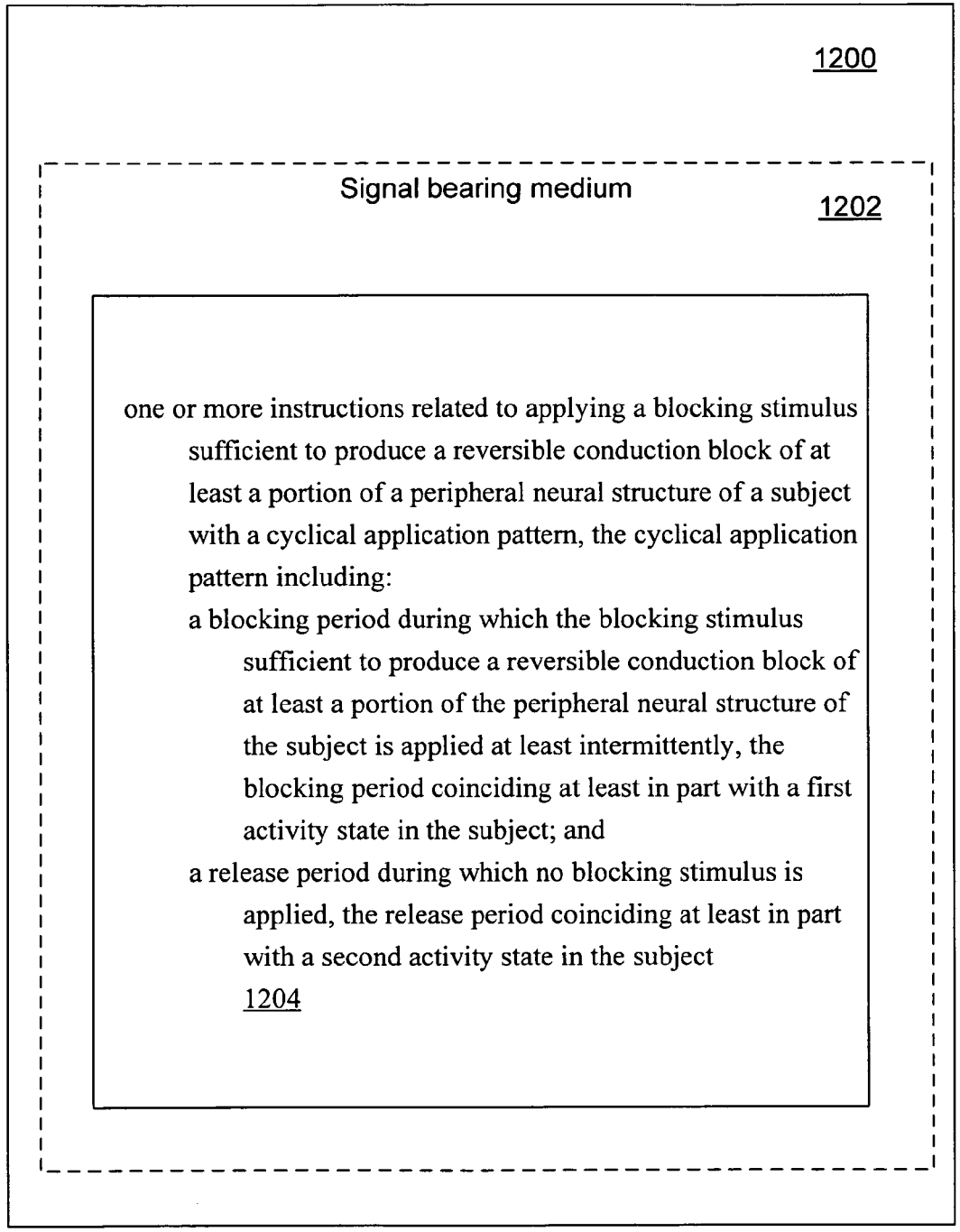
FIG. 20 is a block diagram of a system including a signal-bearing medium bearing instructions related to operation of a neural modulation system.

In still other embodiments, as illustrated in FIG. 20, a system 1200 may include a signal bearing medium 1202 bearing: one or more instructions related to applying a blocking stimulus sufficient to produce a reversible conduction block of at least a portion of a peripheral neural structure of a subject with a cyclical application pattern, a cycle of the cyclical application pattern including a blocking period during which the blocking stimulus sufficient produce a reversible conduction block of at least a portion of the peripheral neural structure of the subject is applied at least intermittently, the blocking period coinciding at least in part with a first activity state in the subject; and a release period during which no blocking stimulus is applied, the release period coinciding at least in part with a second activity state in the subject, as indicated at 1204.

The signal bearing medium may bear one or more instructions related to receiving an input indicative of an activity state of the subject, wherein the input is indicative of at least one of the first activity state and the second activity state of the subject. The one or more instructions may be related to receiving an input indicative of an overall activity state of the subject, wherein the first activity state represents a relatively lower overall activity of the subject and the second activity state represents a relatively higher overall activity of the subject. In some embodiments, the instructions may be related to receiving an input indicative of use of a body portion innervated by the peripheral neural structure by the subject, wherein the first activity state represents a relatively lower use of a body portion innervated by the peripheral neural structure by the subject and the second activity state represents a relatively higher use of a body portion innervated by the peripheral neural structure by the subject.

In some embodiments, the one or more instructions related to applying a blocking stimulus sufficient to produce a reversible conduction block of at least a portion of a peripheral neural structure of a subject with a cyclical application pattern may include one or more instructions related to applying a blocking stimulus sufficient to produce a reversible conduction block of at least a portion of a peripheral neural structure of a subject substantially continuously during the blocking period. In some embodiments, they may be related to applying a blocking stimulus sufficient to produce a reversible conduction block of at least a portion of a peripheral neural structure of a subject intermittently during the blocking period. In some embodiments, the one or more instructions may be related to applying a blocking stimulus sufficient to produce a reversible conduction block of at least a portion of a peripheral neural structure of a subject intermittently at a fixed repetition rate during the blocking period.

The one or more instructions related to applying a blocking stimulus sufficient to produce a reversible conduction block of at least a portion of a peripheral neural structure of a subject with a cyclical application pattern may include one or more instructions related to applying a blocking stimulus sufficient to produce a reversible conduction block of at least a portion of a peripheral neural structure of a subject with a cyclical application pattern having a period of about one day, or other period as described elsewhere herein.

A system may include one or more instructions related to applying a blocking stimulus sufficient to produce a reversible conduction block of at least a portion of a peripheral neural structure of a subject with a cyclical application pattern for a fixed number of cycles, or for fixed duration.

In some embodiments of systems as described herein, the signal-bearing medium may include a computer-readable medium. In some embodiments, the signal-bearing medium may include a recordable medium. In some embodiments, the signal-bearing medium may include a non-volatile memory, such as ROM, PROM, EPROM, EEPROM, or Flash memory, for example. In some embodiments, the signal-bearing medium may include a communications medium, such as at least one optical fiber or wire, or a wireless communications medium.

In a further embodiment, as shown in FIG. 21, a system 1250 may include a signal bearing medium 1252 bearing one or more instructions related to applying a blocking stimulus sufficient to produce a reversible conduction block of at least a portion of a peripheral neural structure of a subject with a cyclical application pattern, a cycle of the cyclical application pattern including a blocking period during which the blocking stimulus sufficient produce a reversible conduction block of at least a portion of the peripheral neural structure of the subject is applied at least intermittently, the blocking period coinciding at least in part with a first activity state in the subject; and a release period during which no blocking stimulus is applied, the release period coinciding at least in part with a second activity state in the subject, as indicated at 1254; one or more instructions related to detecting the onset of the first activity state in the subject, as indicated at 1256; and one or more instructions related to initiating a blocking period during which a blocking stimulus sufficient produce to reversible conduction block of at least a portion of the peripheral neural structure of the subject is applied at least intermittently responsive to detecting the onset of the first activity state in the subject, as indicated at 1258.

The instructions related to initiating a blocking period during which a blocking stimulus sufficient produce to reversible conduction block of at least a portion of the peripheral neural structure of the subject is applied at least intermittently responsive to detecting the onset of a first activity state in the subject may include one or more instructions related to initiating the blocking period substantially immediately upon detecting the onset of the first activity state in the subject, or, at a delay interval after detecting the onset of the first activity state in the subject. In some embodiments, the one or more instructions related to initiating a blocking period during which a blocking stimulus sufficient produce to reversible conduction block of at least a portion of the peripheral neural structure of the subject is applied at least intermittently responsive to detecting the onset of a first activity state in the subject include one or more instructions related to initiating a release period during which no blocking stimulus is applied after an interval determined relative to the initiation of the blocking period.

Figure 22:
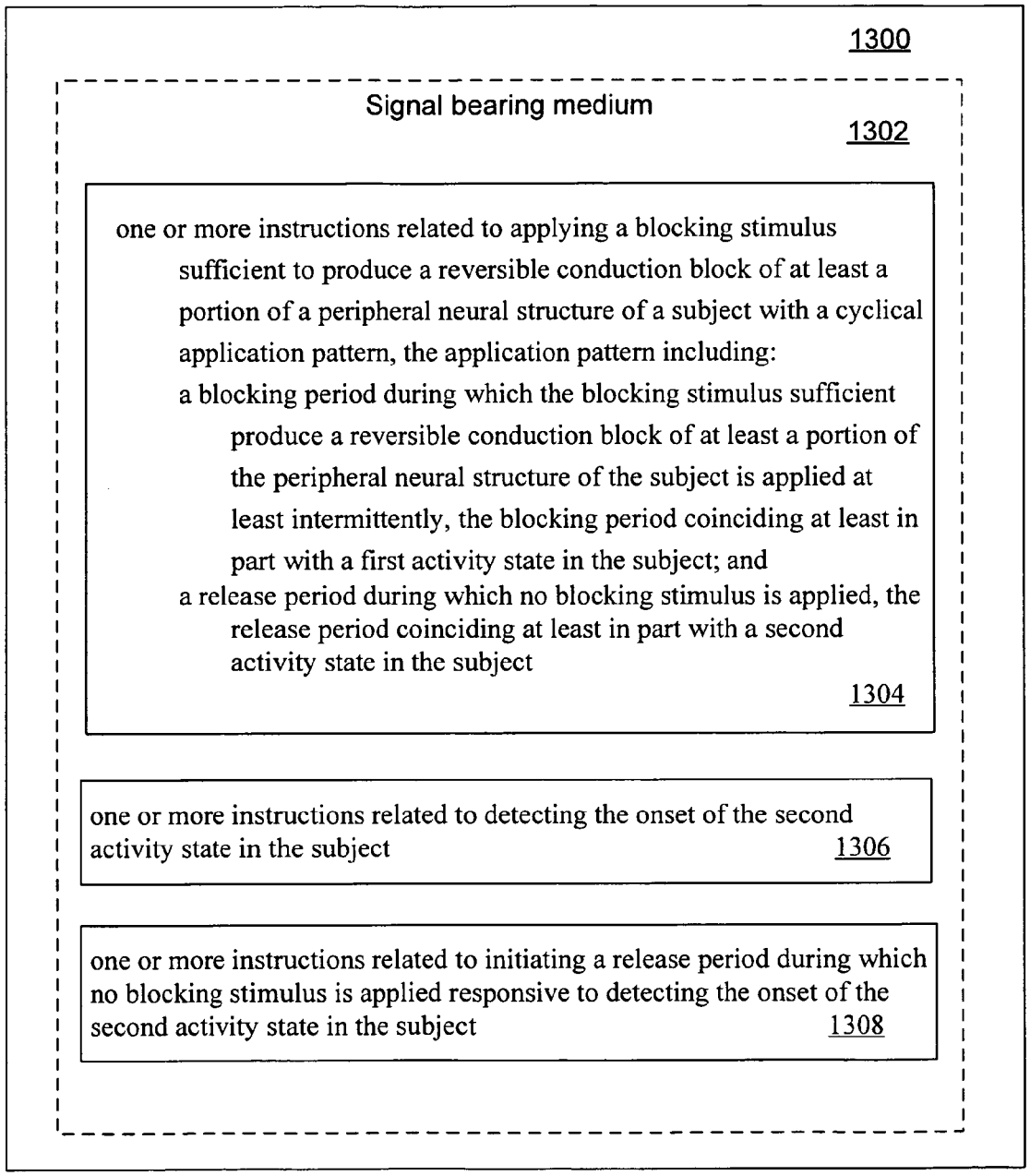
FIG. 22 is a block diagram of a system including a signal-bearing medium bearing instructions related to operation of a neural modulation system.

Another embodiment, as shown in FIG. 22, a system 1300 may include a signal bearing medium 1302 bearing: one or more instructions related to applying a blocking stimulus sufficient to produce a reversible conduction block of at least a portion of a peripheral neural structure of a subject with a cyclical application pattern, a cycle of the cyclical application pattern including a blocking period during which the blocking stimulus sufficient produce a reversible conduction block of at least a portion of the peripheral neural structure of the subject is applied at least intermittently, the blocking period coinciding at least in part with a first activity state in the subject; and a release period during which no blocking stimulus is applied, the release period coinciding at least in part with a second activity state in the subject, as indicated at 1304; one or more instructions related to detecting the onset of the second activity state in the subject, as indicated at 1306; and one or more instructions related to initiating a release period during which no blocking stimulus is applied responsive to detecting the onset of the second activity state in the subject, as indicated at 1308.

The one or more instructions related to initiating a release period during which no blocking stimulus is applied responsive to detecting the onset of the second activity state in the subject may include one or more instructions related to initiating the release period substantially immediately upon onset of the second activity state in the subject, or at a delay interval after detecting the onset of the second activity state in the subject, as described elsewhere herein.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." Those skilled in the art will recognize that "configured to" can generally encompass active-state components and/or inactive-state components and/or standby-state components, etc. unless context requires otherwise.

In some instances, one or more components may be referred to herein as "configured to." Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, the phrase "A and/or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of modulating neural activity comprising:
applying a blocking stimulus sufficient to produce a reversible conduction block of at least a portion of a peripheral neural structure of a subject with a cyclical application pattern, a cycle of the cyclical application pattern including:
a blocking period during which the blocking stimulus sufficient to produce a reversible conduction block of at least a portion of the peripheral neural structure of the subject is applied at least intermittently, the blocking period coinciding at least in part with a low activity state in the subject; and
a release period during which no blocking stimulus is applied, the release period coinciding at least in part with a higher activity state in the subject.

2. The method of claim 1, wherein applying a blocking stimulus sufficient to produce a reversible conduction block of at least a portion of a peripheral neural structure of a subject with a cyclical application pattern includes applying a blocking stimulus sufficient to produce a reversible conduction block of at least a portion of a peripheral neural structure of a subject substantially continuously during the blocking period.

3. The method of claim 1, wherein applying a blocking stimulus sufficient to produce a reversible conduction block of at least a portion of a peripheral neural structure of a subject with a cyclical application pattern includes applying a blocking stimulus sufficient to produce a reversible conduction block of at least a portion of a peripheral neural structure of a subject intermittently during the blocking period.

4. The method of claim 1, wherein applying a blocking stimulus sufficient to produce a reversible conduction block of at least a portion of a peripheral neural structure of a subject with a cyclical application pattern includes applying a blocking stimulus sufficient to produce a reversible conduction block of at least a portion of a peripheral neural structure of a subject with a cyclical application pattern having a period of about one day.

5. The method of claim 1, wherein applying a blocking stimulus sufficient to produce a reversible conduction block of at least a portion of a peripheral neural structure of a subject with a cyclical application pattern includes applying a blocking stimulus sufficient to produce substantially complete blockage of conduction in the peripheral neural structure of the subject.

6. The method of claim 1, wherein applying a blocking stimulus sufficient to produce a reversible conduction block of at least a portion of a peripheral neural structure of a subject with a cyclical application pattern includes applying a blocking stimulus sufficient to produce blockage of a subset of nerve fibers in the peripheral neural structure of the subject.

7. The method of claim 6, wherein applying a blocking stimulus sufficient to produce a reversible conduction block of at least a portion of a peripheral neural structure of a subject with a cyclical application pattern includes applying a blocking stimulus sufficient to produce blockage of a subset of nerve fibers within at least one of a selected diameter range in the peripheral neural structure of the subject, a selected spatial distribution within the peripheral neural structure of the subject, or at least one selected fascicle within the peripheral neural structure of the subject.

8. The method of claim 1, wherein the activity of the subject is at least one of an overall activity of the subject or the use of a body portion innervated by the peripheral neural structure by the subject.

9. The method of claim 1, wherein the cyclical application pattern is repeated over a period of time sufficient to produce modulation of at least one of an immune response, a metabolic response, or an inflammatory response in at least a region innervated by the peripheral neural structure.

10. The method of claim 1, wherein applying a blocking stimulus sufficient to produce a reversible conduction block of at least a portion of a peripheral neural structure of a subject with a cyclical application pattern includes applying a blocking stimulus sufficient to produce a reversible conduction block of at least a portion of a peripheral neural structure of a subject with a cyclical application pattern for at least one of a fixed number of cycles or a fixed duration.

11. The method of claim 1, including: detecting the onset of the a low activity state in the subject; and initiating the blocking period responsive to detecting the onset of a low activity state in the subject.

12. The method of claim 1, including: detecting the onset of the higher activity state in the subject; and initiating the release period during which no blocking stimulus is applied responsive to detecting the higher activity state in the subject.

13. A neural modulation system comprising:
a sensor configured to generate a signal indicative of an activity state of at least a portion of a body of a subject innervated by a peripheral neural structure,
responsive to an activity of the at least a portion of the body of the subject; a signal input structure operatively connected to the sensor and configured to receive the signal indicative of the activity state of at least the portion of the body of the subject innervated by the peripheral neural structure;
and
a signal processing portion configured to:
distinguish a low activity state of the at least a portion of the body of the subject innervated by the peripheral neural structure from a higher activity state of the at least a portion of the body of the subject innervated by the peripheral neural structure, at least partially based on the signal received by the signal input structure; and
generate a blocking stimulus control signal for driving production of a blocking stimulus configured to reversibly block conduction of action potentials in the peripheral neural structure of the subject during at least a portion of the low activity state.

14. The neural modulation system of claim 13, further comprising a blocking stimulus source responsive to the blocking stimulus control signal to produce the blocking stimulus configured to reversibly block conduction in the peripheral neural structure of the subject during the at least a portion of the low activity state.

15. The neural modulation system of claim 13, wherein the signal processing portion is configured to perform at least one of encryption or decryption of at least one of the blocking stimulus control signal and the signal received by the signal input structure.

16. The neural modulation system of claim 13, wherein the sensor includes at least one of a pressure sensor, a force sensor, a chemical sensor, a temperature sensor, an electrical sensor, a magnetic sensor, an optical sensor, or a motion sensor.

17. The neural modulation system of claim 13, including an override signal input structure configured to receive an override signal, wherein the signal processing portion is configured to override generation of the blocking stimulus control signal responsive to an override signal indicative of at least one of an override condition of the body of the subject, an override condition external to the body of the subject, or a user override request on the override signal input structure.

18. The neural modulation system of claim 13, wherein the sensor is a physiological sensor responsive to a physiological parameter of the at least a portion of the body of the subject.

19. The neural modulation system of claim 18, wherein the physiological sensor is configured to generate a signal indicative of at least one of activity of a heart of the subject, activity of a brain of the subject, activity of a peripheral nervous system of the subject, activity of a muscle of the subject, respiration of the subject, or a body temperature of the subject.

20. The neural modulation system of claim 18, wherein the physiological sensor is configured to generate a signal indicative of activity of a heart of the subject.

21. The neural modulation system of claim 18, wherein the physiological sensor is configured to generate a signal indicative of activity of a brain of the subject.

22. The neural modulation system of claim 18, wherein the physiological sensor is configured to generate a signal indicative of activity of a peripheral neural system of the subject.

23. The neural modulation system of claim 18, wherein the physiological sensor is configured to generate a signal indicative of activity of a muscle of the subject.

24. The neural modulation system of claim 18, wherein the physiological sensor is configured to generate a signal indicative of respiration of the subject.

25. The neural modulation system of claim 18, wherein the physiological sensor is configured to generate a signal indicative of a body temperature of the subject.

26. The neural modulation system of claim 18, further comprising a blocking stimulus source responsive to the blocking stimulus control signal to produce the blocking stimulus configured to reversibly block conduction in the peripheral neural structure of the subject during the at least a portion of the low activity state.

27. The neural modulation system of claim 13, wherein the sensor is a physical activity sensor responsive to physical activity of the at least a portion of the body of the subject.

28. The neural modulation system of claim 27, wherein the physical activity sensor is configured to generate a signal indicative of at least one of motion of the at least a portion of the body of the subject innervated by the peripheral neural structure, acceleration of the at least a portion of the body of the subject innervated by the peripheral neural structure, body position of the subject, or posture of the subject.

29. The neural modulation system of claim 13, including an override signal input structure configured to receive a signal indicative of a condition of the body of the subject, wherein the signal processing portion is configured to override generation of the blocking stimulus control signal responsive to a signal indicative of an override condition of the body of the subject on the override signal input structure.

30. The neural modulation system of claim 13, including an override signal input structure configured to receive a signal indicative of a condition external to the body of the subject, wherein the signal processing portion is configured to override generation of the blocking stimulus control signal responsive to a signal indicative of an override condition external to the body of the subject on the override signal input structure.

31. The neural modulation system of claim 13, including an override signal input structure configured to receive from a user input device, wherein the signal processing portion is configured to override generation of the blocking stimulus control signal responsive to a signal indicative of a user override request on the override signal input structure.

32. The neural modulation system of claim 31, wherein the signal processing portion is configured to perform at least one of encryption or decryption of at least one of the blocking stimulus control signal, the signal received by the signal input structure, or the signal indicative of a user override request on the override signal input structure.

33. A neural modulation system comprising:
a signal input structure configured to receive a signal indicative of an activity state of at least a portion of a body of a subject innervated by a peripheral neural structure;
a user input device operatively connected to the signal input structure and configured to generate a signal responsive to a user input indicative of an activity state of at least a portion of a body of a subject innervated by the peripheral neural structure; and
a signal processing portion configured to:
distinguish a low activity state of the at least a portion of the body of the subject innervated by the peripheral neural structure from a higher activity state of the at least a portion of the body of the subject innervated by the peripheral neural structure from the signal received at the signal input structure; and
generate a blocking stimulus configured to reversibly block conduction in the peripheral neural structure of the subject during at least a portion of the low activity state.

34. The neural modulation system of claim 33, wherein the user input device includes at least one of a voice-activated input device or a user-activated switch.

35. A system comprising: a computer-readable medium bearing:
one or more instructions related to producing a reversible conduction block in a peripheral neural structure of at least a portion of a body of a subject while the at least a portion of a body of a subject is in a low activity state;
one or more instructions related to reversing the reversible conduction block in the peripheral neural structure of the at least a portion of a body of a subject to permit conduction in the peripheral neural structure when the at least a portion of the body of the subject is in a higher activity state; and one or more instructions related to repeating the steps of producing a reversible conduction block in the peripheral neural structure of the at least a portion of the body of the subject while the at least a portion of the body of the subject is in a low activity state and reversing the reversible conduction block in the peripheral neural structure of the at least a portion of a body of a subject to permit conduction in the peripheral neural structure when the at least a portion of the body of the subject is in a higher activity state.

36. The system of claim 35, wherein the signal bearing medium bears one or more instructions related to repeating the steps of producing a reversible conduction block in a peripheral neural structure of a subject while the subject is in a low activity state and reversing the reversible conduction block in the peripheral neural structure of the subject to permit conduction in the peripheral neural structure when the subject is in a higher activity state cyclically, wherein each cycle includes a blocking period during which a blocking stimulus sufficient to produce reversible conduction block in a peripheral neural structure of a subject is produced while the subject is in a low activity state and a release period during which no blocking stimulus is delivered.

37. The system of claim 35, wherein the computer-readable medium includes at least one of a non-volatile memory, a recordable medium, a communications medium, an optical fiber, a wire, a wireless communications medium.

38. The system of claim 35, wherein the computer-readable medium bears one or more instructions related to receiving an input indicative of the activity state of at least a portion of the body of the subject.

39. The system of claim 38, wherein the computer-readable medium bears one or more instructions related to at least one of encrypting or decrypting the input indicative of an activity state of the subject.

40. The system of claim 38, wherein the one or more instructions related to receiving an input indicative of the activity state of the subject include one or more instructions related to receiving an input indicative of at least one of overall activity of the subject or use of a body portion innervated by the peripheral neural structure by the subject.

41. The system of claim 38, wherein the one or more instructions related to receiving an input indicative of the activity state of at least a portion of the body of the subject include one or more instructions related to at least one of receiving an input indicative of physiological activity of the subject, receiving an input indicative of a heart rate of the subject, receiving an input indicative of a brain activity of the subject, receiving an input indicative of a muscle activity of the subject, receiving an input indicative of respiration of the subject, receiving an input indicative of a peripheral nervous system activity of the subject, or receiving an input indicative of a body temperature of the subject.

42. The system of claim 38, wherein the one or more instructions related to receiving an input indicative of the activity state of at least a portion of the body of the subject include one or more instructions related to at least one of receiving an input indicative of physical activity of the subject, receiving an input indicative of motion of the subject, receiving an input indicative of a body position of the subject, or receiving an input indicative of posture of the subject.

43. The system of claim 38, wherein the one or more instructions related to receiving an input indicative of the activity state of at least a portion of the body of the subject include one or more instructions related to at least one of receiving an input from a pressure sensor, receiving an input from a force sensor, receiving an input from a chemical sensor, receiving an input from a temperature sensor, receiving an input from an electrical sensor, receiving an input from a magnetic sensor, receiving an input from an optical sensor, receiving an input from a motion sensor, or receiving an input from a switch.

44. The system of claim 35, wherein the computer-readable medium bears one or more instructions related to receiving an input indicative of a user instruction.

45. The system of claim 44, wherein the one or more instructions related to receiving an input indicative of a user instruction include one or more instructions related to at least one of receiving an input from a user input device, receiving an input from a voice-activated input device, or receiving an input from a user-activated switch.

46. A system comprising:
a computer-readable medium bearing:
one or more instructions related to applying a blocking stimulus sufficient to produce a reversible conduction block of at least a portion of a peripheral neural structure of a subject with a cyclical application pattern, a cycle of the cyclical application pattern including: a blocking period during which the blocking stimulus sufficient produce a reversible conduction block of at least a portion of the peripheral neural structure of the subject is applied at least intermittently, the blocking period coinciding at least in part with a low activity state in the subject; and
a release period during which no blocking stimulus is applied, the release period coinciding at least in part with a higher activity state in the subject.

47. The system of claim 46, wherein the computer-readable medium bears:
one or more instructions related to receiving an input indicative of an activity state of the subject, wherein the input is indicative of at least one of the low activity state and the higher activity state of the subject.

48. The system of claim 46, wherein the one or more instructions related to applying a blocking stimulus sufficient to produce a reversible conduction block of at least a portion of a peripheral neural structure of a subject with a cyclical application pattern include one or more instructions related to applying a blocking stimulus sufficient to produce a reversible conduction block of at least a portion of a peripheral neural structure of a subject substantially continuously during the blocking period.

49. The system of claim 46, wherein the one or more instructions related to applying a blocking stimulus sufficient to produce a reversible conduction block of at least a portion of a peripheral neural structure of a subject with a cyclical application pattern include one or more instructions related to applying a blocking stimulus sufficient to produce a reversible conduction block of at least a portion of a peripheral neural structure of a subject intermittently during the blocking period.

50. The system of claim 46, wherein the computer-readable medium includes at least one of a recordable medium, a non-volatile memory, a communications medium, an optical fiber, a wire, a wireless communications medium.

51. The system of claim 46, wherein the computer-readable medium bears:
one or more instructions related to detecting the onset of the low activity state in the subject; and
one or more instructions related to initiating a blocking period during which a blocking stimulus sufficient produce to reversible conduction block of at least a portion of the peripheral neural structure of the subject is applied at least intermittently responsive to detecting the onset of the low activity state in the subject.

52. The system of claim 51, wherein the one or more instructions related to initiating a blocking period during which a blocking stimulus sufficient produce to reversible conduction block of at least a portion of the peripheral neural structure of the subject is applied at least intermittently responsive to detecting the onset of a low activity state in the subject include one or more instructions related to initiating the blocking period substantially immediately upon detecting the onset of the low activity state in the subject.

53. The system of claim 46, wherein the computer-readable medium bears:
one or more instructions related to detecting the onset of the higher activity state in the subject; and
one or more instructions related to initiating a release period during which no blocking stimulus is applied responsive to detecting the onset of the higher activity state in the subject.

* * * * *

UNITED STATES PATENT AND TRADEMARK OFFICE
CERTIFICATE OF CORRECTION

PATENT NO. : 8,180,446 B2
APPLICATION NO. : 11/999721
DATED : May 15, 2012
INVENTOR(S) : Ralph G. Dacey, Jr. et al.

Page 1 of 1

It is certified that error appears in the above-identified patent and that said Letters Patent is hereby corrected as shown below:

Column 16, Line 39: amend the following
Please add "incorporated" after "is" and before "herein"

Claim 11, Column 32, Line 24: ENTER tab was inadvertently not pressed.
Amend by pressing the ENTER tab after "including:" and before "detecting"

Claim 11, Column 32, Line 25: ENTER tab was inadvertently not pressed.
Amend by pressing the ENTER tab after "and" and before "initiating"

Claim 12, Column 32, Line 28: ENTER tab was inadvertently not pressed.
Amend by pressing the ENTER tab after "including:" and before "detecting"

Claim 12, Column 32, Line 29: ENTER tab was inadvertently not pressed.
Amend by pressing the ENTER tab after "and" and before "initiating"

Claim 13, Column 32, Line 35: ENTER tab was inadvertently pressed.
Amend by deleting the ENTER tab.

Claim 13, Column 32, Line 37: ENTER tab was inadvertently not pressed.
Amend by pressing the ENTER tab after "subject;" and before "a"

Claim 35, Column 34, Line 39: ENTER tab was inadvertently not pressed.
Amend by pressing the ENTER tab after "comprising:"

Claim 35, Column 34, Line 50: ENTER tab was inadvertently not pressed.
Amend by pressing the ENTER tab after "and" and before "one"

Claim 46, Column 36, Line 2: ENTER tab was inadvertently not pressed.
Amend by pressing the ENTER tab after "including:" and before "a"

Signed and Sealed this
Eighteenth Day of September, 2012

David J. Kappos
*Director of the United States Patent and Trademark Office*